US010570464B2

(12) United States Patent
Andini et al.

(10) Patent No.: US 10,570,464 B2
(45) Date of Patent: Feb. 25, 2020

(54) BACTERIAL PATHOGEN IDENTIFICATION BY HIGH RESOLUTION MELTING ANALYSIS

(71) Applicant: The Board of Trustees of the Leland Stanford Junior University, Stanford, CA (US)

(72) Inventors: Nadya Andini, Fremont, CA (US); Samuel S. Yang, Burlingame, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 85 days.

(21) Appl. No.: 15/589,392

(22) Filed: May 8, 2017

(65) Prior Publication Data

US 2017/0321257 A1 Nov. 9, 2017

Related U.S. Application Data

(60) Provisional application No. 62/333,374, filed on May 9, 2016.

(51) Int. Cl.
| | |
|---|---|
| *C12P 19/34* | (2006.01) |
| *C12Q 1/689* | (2018.01) |
| *C12Q 1/6816* | (2018.01) |
| *G16B 30/00* | (2019.01) |
| *G16B 40/00* | (2019.01) |
| *C12Q 1/6851* | (2018.01) |
| *G16B 30/10* | (2019.01) |
| *G16B 40/20* | (2019.01) |
| *G16B 40/30* | (2019.01) |
| *G06N 7/00* | (2006.01) |
| *G06N 20/00* | (2019.01) |

(52) U.S. Cl.
CPC .......... *C12Q 1/689* (2013.01); *C12Q 1/6816* (2013.01); *C12Q 1/6851* (2013.01); *G16B 30/00* (2019.02); *G16B 30/10* (2019.02); *G16B 40/00* (2019.02); *C12Q 2600/156* (2013.01); *G06N 7/005* (2013.01); *G06N 20/00* (2019.01); *G16B 40/20* (2019.02); *G16B 40/30* (2019.02)

(58) Field of Classification Search
CPC .......... C12Q 1/6851; C12Q 2563/159; C12Q 1/6816; C12Q 1/689; C12Q 2600/156; G16B 30/00; G16B 40/00
See application file for complete search history.

(56) References Cited

U.S. PATENT DOCUMENTS

| | | | | |
|---|---|---|---|---|
| 2003/0157509 A1* | 8/2003 | Mirzabekov | ......... | C12Q 1/6837 435/6.11 |
| 2006/0099618 A1 | 5/2006 | Jannes et al. | | |
| 2015/0307923 A1 | 10/2015 | Fredricks et al. | | |
| 2016/0040216 A1 | 2/2016 | Akins et al. | | |
| 2017/0029906 A1 | 2/2017 | Divakar et al. | | |

FOREIGN PATENT DOCUMENTS

| | | |
|---|---|---|
| EP | 1713937 B1 | 8/2016 |
| WO | 2005045074 A2 | 5/2005 |

OTHER PUBLICATIONS

Gurtler et al., Journal of Microbiology Methods, 90, 167-181, May (Year: 2012).*
Cheng et al., Clinical Chemistry, 52(11):1997-2994, (Year: 2006).*
Park et al., Journal of Clinical Microbiology, 38 (11): 4080-4085, Nov. (Year: 2000).*
Athamanolap et al., Plos One, 9(10), e109094, pp. 1-10, Oct. (Year: 2014).*
Fraley et al., Nucleic Acids Research, 41(18), e175, pp. 1-13, Aug. (Year: 2013).*
Gutierrez-Aguirre et al., Plant Pathology, Techniques and Protocols, Methods in Molecular Biology, vol. 1302, Springer Science + Business Media, New York, pp. 331-347, (Year: 2015).*
Wittwer et al. (2003) High-resolution genotyping by amplicon melting analysis using LCGreen. Clinical Chemistry 49:853-860.
Tong et al. (2012) Microbiological applications of high-resolution melting analysis. J. Clin. Microbiol. 50:3418-3421.
Fraley et al. (2013) Universal digital high-resolution melt: a novel approach to broad-based profiling of heterogeneous biological samples. Nucleic Acids Res. 41:e175.
Athamanolap et al. (2014) Trainable high resolution melt curve machine learning classifier for large-scale reliable genotyping of sequence variants. PloS One 9:e109094.
Hardick et al. (2012) Identification of bacterial pathogens in ascitic fluids from patients with suspected spontaneous bacterial peritonitis by use of broad-range PCR (16S PCR) coupled with high-resolution melt analysis. J. Clin. Microbiol. 50:2428-2432.
Jeng et al. (2012) Application of a 16S rRNA PCR-high-resolution melt analysis assay for rapid detection of *Salmonella bacteremia*. J. Clin. Microbiol. 50:1122-1124.
Masek et al. (2014) Sensitive detection and serovar differentiation of typhoidal and nontyphoidal *Salmonella enterica* species using 16S rRNA Gene PCR coupled with high-resolution melt analysis. J. Mol. Diagn. 16:261-266.
Niimi et al. (2015) Melting Temperature Mapping Method: A Novel Method for Rapid Identification of Unknown Pathogenic Microorganisms within Three Hours of Sample Collection. Scientific reports 5, 12543.
Won et al. (2010) Rapid identification of bacterial pathogens in positive blood culture bottles by use of a broad-based PCR assay coupled with high-resolution melt analysis. J. Clin. Microbiol. 48:3410-3413.

(Continued)

*Primary Examiner* — Cynthia B Wilder
(74) *Attorney, Agent, or Firm* — Jenny L. Buchbinder; Bozicevic, Field & Francis LLP

(57) ABSTRACT

Methods and oligonucleotide reagents for identification of bacteria by high resolution melting (HRM) analysis are described. In particular, the invention relates to HRM analysis of hypervariable bacterial genomic DNA of the internal transcribed spacer (ITS) region for fingerprinting eubacterial pathogens.

29 Claims, 57 Drawing Sheets

Specification includes a Sequence Listing.

(56) References Cited

OTHER PUBLICATIONS

Yang et al. (2009) Rapid identification of biothreat and other clinically relevant bacterial species by use of universal PCR coupled with high-resolution melting analysis. J. Clin. Microbiol. 2009 47:2252-2255.

Lilliebridge et al. (2011) The utility of high-resolution melting analysis of SNP nucleated PCR amplicons—an MLST based *Staphylococcus aureus* typing scheme. PloS one 6:e19749.

Fraley et al. (2016) Nested Machine Learning Facilitates Increased Sequence Content for Large-Scale Automated High Resolution Melt Genotyping. Scientific reports 6:19218.

Reja et al. (2010) ScreenClust: Advanced statistical software for supervised and unsupervised high resolution melting (HRM) analysis. Methods 50:S10-14.

Gurtler et al. (1996) New approaches to typing and identification of bacteria using the 16S-23S rDNA spacer region. Microbiology 142 ( Pt 1):3-16.

Mandviwala et al. (2010) High-throughput identification and quantification of Candida species using high resolution derivative melt analysis of panfungal amplicons. J. Mol. Diagn. 12:91-101.

Somogyvari et al. (2012) Detection of invasive fungal pathogens by real-time PCR and high-resolution melting analysis. In Vivo 26:979-983.

Frayley et al. (2013) Universal digital high-resolution melt: a novel approach to broad-based profiling of heterogeneous biological samples. Nucleic Acids Research 41:e175.

Jeng et al. (2012) Comparative analysis of two broad-range PCR assays for pathogen detection in positive-blood-culture bottles: PCR-high-resolution melting analysis versus PCR-mass spectrometry. J. Clin. Microbiol. 50(10)3287-3292.

Gago et al. (2014) Ribosomic DNA intergenic spacer 1 region is useful when identifying *Candida parapsilosis* spp. complex based on high-resolution melting analysis. Med Mycol. 52(5):472-481.

Aghaei et al. (2014) First report on natural Leishmania infection of Phlebotomus sergenti due Leishmania tropica by high resolution melting curve method in South-eastern Iran. Asian Pac. J. Trop. Med. 7(2):93-96.

Gutierrez et al. (2013) Bartonellae in domestic and stray cats from Israel: comparison of bacterial cultures and high-resolution melt real-time PCR as diagnostic methods. Vector Borne Zoonotic Dis. 13(12):857-864.

Zackay et al. (2013) Polymorphism in the HASPB repeat region of East African Leishmania donovani strains. PLoS Negl. Trop. Dis. 7(1):e2031.

Bousslimi et al. (2012) Natural infection of North African gundi (*Ctenodactylus gundi*) by Leishmania tropica in the focus of cutaneous leishmaniasis, Southeast Tunisia. Am J Trop Med Hyg. 86(6):962-965.

Granados-Cifuentes et al. (2011) The use of high-resolution melting analysis for genotyping Symbiodinium strains: a sensitive and fast approach. Mol Ecol Resour. 11(2):394-399.

Areekit et al. (2009) High resolution melting real-time PCR for rapid discrimination between Brugia malayi and Brugia pahangi. J. Med. Assoc. Thai. 92 Suppl 3:S24-28.

Perera et al. (2015) Rapid identification of Helicoverpa armigera and Helicoverpa zea (Lepidoptera: Noctuidae) using ribosomal RNA internal transcribed spacer 1. J. Insect Sci. 15. pii:155.

Talmi-Frank et al. (2010) Detection and identification of old world Leishmania by high resolution melt analysis. PLoS Negl. Trop. Dis. 12:4(1):e581.

\* cited by examiner

FIG. 2C

```
ITS_Short  CCTTACCTTAAAGAAGCGTACTTTGCAGTGCTTCACACAGATTGTCTGATAGAAAGTGAAA
ITS_Long   CCTTACCTTAAAGAAGCGTACTTTGCAGTGCTTCACACAGATTGTCTGATGAAAATGAGCA
           ************************************************ **  ** *

ITS_Short  AGCAAGGCGTCTTGCGA-----------------------------------------
ITS_Long   GTAAAACCTCTACAGGCTTGTAGCTCAGGTGGTTAGAGCGCACCCCTGATAAGGGTGAGG
           *  *

ITS_Short  ------------------------AGCAGACTGACACGTCCCCTTCG-----------
ITS_Long   TCGGTGGTTCAAGTCCACTCAGGCCTACCGCAAATTTGCACGCAAATTTGAAGAGGTTTA
                                   *  *   ***  *   **  *

ITS_Short  ----------TCTAGA----GGCCCAGGACACGCCCTTTCAGGGGGTAACA
ITS_Long   ACTACATGTTATGGGCTATAGCTCAGTGGTAGAGCGCCTGCTTTGCACGCAGGAGGTC
              * *                      ** **  * **** **

ITS_Short  GGGGTTCGAATCCCCTAGGGACGCCACTTGCTGGTTTGTGAGTGAAAGTCACCTGCCTT-
ITS_Long   TGCGGGTTCGAATCCCGCATAGCTC--CACCATCTCTGTAGTGATTAAATAAAAAAT---
            *  ***** *   * **  *        *   * *  **** *     *

ITS_Short  AATATCTCAAAACTCATCTTCGGGTGATGTTTGAGATATTTGCTCTTTTAAAATCTGGAT
ITS_Long   --ACTTCAGAGTGTACCTGCAAGGTTCACTGCGAAGTTTTTGCTCTCTTTTAAAATCTGGAT
             *     *  *  ***   *   **    *    * **  ***** *************

ITS_Short  CAAGCTGAAAATTGAAACAACACTGAACAACGAGAGTTGTTCGTGAGTCTCTCAAATTTCGC
ITS_Long   CAAGCTGAAAATTGAAACAACACTGAACAACGAGAGTTGTTCGTGAGTCTCTCAAATTTCGC
           ************************************************************

ITS_Short  AACACGATGAATCGCAAGAAACATCTTCGGGTTGTGAGG
ITS_Long   AACACGATGAATCGCAAGAAACATCTTCGGGTTGTGAGG
           ***************************************
```

Brucella ovis

FIG. 24

Burkholderia cepacia

BACTERIAL PATHOGEN IDENTIFICATION BY HIGH RESOLUTION MELTING ANALYSIS

CROSS-REFERENCE TO RELATED APPLICATION

This application claims benefit under 35 U.S.C. § 119(e) of provisional application 62/333,374, filed May 9, 2016, which application is hereby incorporated by reference in its entirety.

STATEMENT REGARDING FEDERALLY SPONSORED RESEARCH OR DEVELOPMENT

This invention was made with Government support under contract TR001085 awarded by the National Institutes of Health. The Government has certain rights in the invention.

TECHNICAL FIELD

The present invention pertains generally to molecular diagnostics and bacterial pathogen identification. In particular, the invention relates to high resolution melting (HRM) analysis of hypervariable bacterial genomic DNA of the internal transcribed spacer (ITS) region for fingerprinting eubacterial pathogens.

BACKGROUND

Etiologic diagnosis of acute febrile illnesses should be broad and unbiased. These illnesses, often present with vague symptoms, are caused by a myriad of potential pathogens, some emerging or unanticipated, all of which vary by geographic region. Unfortunately, accurate diagnosis of the causative pathogen(s) can be compromised by diagnostic assays biased to target a pre-determined set of microorganisms. Broad differential diagnostics to rapidly identify unknown pathogen(s) within the acute-care timescale would enable early fine-tuning of antibiotic stewardship according to local susceptibility profiles and reduce patient morbidity and mortality.

SUMMARY

The present invention relates to a method for identification of eubacterial pathogens based on HRM analysis of hypervariable ITS bacterial genomic DNA.

In one aspect, the invention includes a method for identifying bacteria in a biological sample from a subject, the method comprising: a) providing a biological sample from the subject; b) isolating bacterial DNA from the biological sample; c) amplifying at least a portion of an internal transcribed spacer (ITS) region of the bacterial DNA using at least one set of primers capable of specifically hybridizing to the ITS region, whereby an amplicon is produced; d) performing high resolution melt (HRM) analysis of the amplicon; and e) identifying the species of the bacteria by comparing an HRM curve for the amplicon to a matching reference HRM curve for genomic ITS DNA from a known bacterial species. The method may further comprise culturing the bacteria from the biological sample prior to amplification of the bacterial nucleic acids.

Bacteria in the biological sample can be distinguished from other known bacterial species with ITS regions having different lengths, copy number, or sequences based on comparing the HRM curve of the amplicon to reference HRM curves for genomic ITS DNA from known bacterial species. In particular, the melt curve shape and melting temperature ($T_m$) of the amplicon is compared to reference HRM curves and $T_m$ values for ITS DNA from known bacteria to identify the bacteria in the biological sample.

In certain embodiments, the amplicon comprises a portion or the entire ITS region of the bacterial genomic DNA.

In certain embodiments, the method further comprises performing HRM analysis of another phylogenetic locus (e.g. 16S rRNA, 23S rRNA, and rpo loci) in the bacterial DNA. For example, HRM analysis may be performed on one or more additional phylogenetic loci to assist in identification or to confirm identification of the bacterial species.

Amplification may be performed using polymerase chain reaction (PCR) techniques, such as, but not limited to, real-time PCR, droplet digital PCR (ddPCR), hot-start PCR, solid phase PCR, and touchdown PCR. In one embodiment, amplification is performed on bacterial DNA from a single cell, and the resulting amplicon is subjected to HRM analysis by the methods described herein. Alternatively, amplification can be performed by techniques other than PCR, such as ligase chain reaction or isothermal amplification.

In certain embodiments, amplification is performed with at least one set of primers selected from the group consisting of: a) a forward primer comprising the nucleotide sequence of SEQ ID NO:1 and a reverse primer comprising the sequence of SEQ ID NO:2; b) a forward primer comprising at least 10 contiguous nucleotides of the nucleotide sequence of SEQ ID NO:1 and a reverse primer comprising at least 10 contiguous nucleotides of the nucleotide sequence of SEQ ID NO:2; c) a forward primer comprising a nucleotide sequence having at least 95% identity to the sequence of SEQ ID NO:1 and a reverse primer comprising a nucleotide sequence having at least 95% identity to the sequence of SEQ ID NO:2, wherein the primer is capable of hybridizing to and amplifying bacterial ITS DNA; d) a forward primer and a reverse primer comprising at least one nucleotide sequence that differs from the corresponding nucleotide sequence of the forward primer or reverse primer of the primer set of (a) in that the primer has up to three nucleotide changes compared to the corresponding sequence, wherein the primer is capable of hybridizing to and amplifying bacterial ITS DNA; and e) a forward primer and a reverse primer comprising nucleotide sequences that are complements of the corresponding nucleotide sequences of the forward primer and reverse primer of a primer set selected from the group consisting of (a)-(d).

In certain embodiments, the method further comprises fractionating the biological sample prior to performing steps (b)-(e). In one embodiment, fractionating comprises partitioning the biological sample into separate picoliter-scale volumes.

The biological sample may be any sample of bodily fluid or tissue infected with bacteria, such as, but not limited to, blood, cerebrospinal fluid (CSF), saliva, mucus, lymph fluid, lavage fluid, skin, or soft tissue. The biological sample may be infected with a single species or more than one species of bacteria. If the biological sample is infected with more than one species of bacteria, the method may further comprise isolating one species of bacteria from the biological sample by diluting the biological sample and removing a portion of the biological sample containing only one species of bacteria, and performing steps (b)-(e) on said portion of the biological sample containing only the one species of bacteria. In one embodiment, the method further comprises separately amplifying bacterial DNA from each of the species by droplet digital PCR and performing steps (d) and (e) on the amplicons from each of the species separately.

In certain embodiments, the method further comprises examining the bacteria by microscopy or sequencing the bacterial DNA.

In certain embodiments, the method further comprises adding a dye that fluoresces when bound to double-stranded DNA. In one embodiment, the method comprises performing amplification of the bacterial ITS DNA in the presence of an intercalating dye. In another embodiment, the method comprises contacting the amplicon with an intercalating dye prior to performing HRM analysis. The intercalating dye may be a fluorescent dye, such as, but not limited to, SYBR® GREEN I fluorescent dye (N',N'-dimethyl-N-[4-[(E)-(3-methyl-1,3-benzothiazol-2-ylidene)methyl]-1-phenylquinolin-1-ium-2-yl]-N-propylpropane-1,3-diamine (Thermo Fisher Scientific, Waltham, Mass.)), LCGREEN® fluorescent dye (Idaho Technology, Inc., Salt Lake City, Utah), LCGREEN® PLUS fluorescent dye (Idaho Technology, Inc., Salt Lake City, Utah), RESOLIGHT® fluorescent dye (Roche Diagnostics, Mannheim, Germany), EVAGREEN® fluorescent dye (Biotium, Inc., Hayward, Calif.), CHROMOFY™ fluorescent dye (TATAA Biocenter, Gdteborg, Sweden) and SYTO™ 9 fluorescent dye (Thermo Fisher Scientific, Waltham, Mass.).

In certain embodiments, HRM analysis is performed in the temperature range from about 50° C. to about 95° C. In one embodiment, the method further comprises adding a low temperature calibrator reference DNA prior to performing the HRM analysis.

In another embodiment, the method further comprises storing the HRM curve for the amplicon in a HRM reference curve database.

HRM curves produced as described herein may be stored in a database.

In another aspect, the invention includes an isolated oligonucleotide not more than 40 nucleotides in length comprising: a) a nucleotide sequence comprising at least 10 contiguous nucleotides from a nucleotide sequence selected from the group consisting of SEQ ID NO:1 and SEQ ID NO:2; b) a nucleotide sequence having at least 95% identity to a nucleotide sequence selected from the group consisting of SEQ ID NO:1 and SEQ ID NO:2, wherein the oligonucleotide is capable of hybridizing to and amplifying bacterial ITS DNA; c) a nucleotide sequence that differs from a nucleotide sequence selected from the group consisting of SEQ ID NO:1 and SEQ ID NO:2 by up to three nucleotide changes, wherein the oligonucleotide is capable of hybridizing to and amplifying bacterial ITS DNA; or d) complements of (a)-(c). In one embodiment, the oligonucleotide comprises a nucleotide sequence selected from the group consisting of SEQ ID NO:1 and SEQ ID NO:2. In another embodiment, the oligonucleotide further comprises a detectable label.

In another aspect, the invention includes a kit for identifying bacteria in a biological sample, the kit comprising: written instructions for identifying the bacteria by HRM analysis; and at least one set of primers capable of specifically hybridizing to and amplifying at least a portion of an internal transcribed spacer (ITS) region of bacterial DNA. In one embodiment, the kit comprises at least one set of primers capable of amplifying the entire ITS region. The kit may further comprise reagents for performing PCR (e.g., a polymerase, nucleotides, and buffers) or HRM analysis (e.g., intercalating dye, low temperature calibrator reference DNA).

In certain embodiments the kit comprises at least one set of primers selected from the group consisting of: a) a forward primer comprising the nucleotide sequence of SEQ ID NO:1 and a reverse primer comprising the sequence of SEQ ID NO:2; b) a forward primer comprising at least 10 contiguous nucleotides of the nucleotide sequence of SEQ ID NO:1 and a reverse primer comprising at least 10 contiguous nucleotides of the nucleotide sequence of SEQ ID NO:2; c) a forward primer comprising a nucleotide sequence having at least 95% identity to the sequence of SEQ ID NO:1 and a reverse primer comprising a nucleotide sequence having at least 95% identity to the sequence of SEQ ID NO:2, wherein the primer is capable of hybridizing to and amplifying bacterial ITS DNA; d) a forward primer and a reverse primer comprising at least one nucleotide sequence that differs from the corresponding nucleotide sequence of the forward primer or reverse primer of the primer set of (a) in that the primer has up to three nucleotide changes compared to the corresponding sequence, wherein the primer is capable of hybridizing to and amplifying bacterial ITS DNA; and e) a forward primer and a reverse primer comprising nucleotide sequences that are complements of the corresponding nucleotide sequences of the forward primer and reverse primer of a primer set selected from the group consisting of (a)-(d). In one embodiment, the kit comprises at least one set of primers comprising a forward primer comprising the sequence of SEQ ID NO:1 and a reverse primer comprising the sequence of SEQ ID NO:2.

In certain embodiments, the kit further comprises an intercalating dye. The intercalating dye may be a fluorescent dye, such as, but not limited to, SYBR® GREEN I fluorescent dye (N',N'-dimethyl-N-[4-[(E)-(3-methyl-1,3-benzothiazol-2-ylidene)methyl]-1-phenylquinolin-1-ium-2-yl]-N-propylpropane-1,3-diamine (Thermo Fisher Scientific, Waltham, Mass.)), LCGREEN® fluorescent dye (Idaho Technology, Inc., Salt Lake City, Utah), LCGREEN® PLUS fluorescent dye (Idaho Technology, Inc., Salt Lake City, Utah), RESOLIGHT® fluorescent dye (Roche Diagnostics, Mannheim, Germany), EVAGREEN® fluorescent dye (Biotium, Inc., Hayward, Calif.), CHROMOFY™ fluorescent dye (TATAA Biocenter, Gdteborg, Sweden), and SYTO™ 9 fluorescent dye (Thermo Fisher Scientific, Waltham, Mass.).

In another aspect, the invention includes a high resolution melt (HRM) system for identifying bacteria comprising: a) at least one set of primers capable of specifically hybridizing to and amplifying at least a portion of an internal transcribed spacer (ITS) region of bacterial DNA; b) an intercalating dye; c) a PCR chamber, wherein the PCR chamber is configured to perform PCR amplification of the bacterial DNA with the at least one set of primers; and d) an HRM chamber, wherein the HRM chamber is configured to perform HRM analysis of the amplified bacterial DNA.

In one embodiment, the HRM system comprises at least one set of primers capable of amplifying the entire ITS region.

In certain embodiments, the HRM system comprises at least one set of primers selected from the group consisting of: a) a forward primer comprising the nucleotide sequence of SEQ ID NO:1 and a reverse primer comprising the sequence of SEQ ID NO:2; b) a forward primer comprising at least 10 contiguous nucleotides of the nucleotide sequence of SEQ ID NO:1 and a reverse primer comprising at least 10 contiguous nucleotides of the nucleotide sequence of SEQ ID NO:2; c) a forward primer comprising a nucleotide sequence having at least 95% identity to the sequence of SEQ ID NO:1 and a reverse primer comprising a nucleotide sequence having at least 95% identity to the sequence of SEQ ID NO:2, wherein the primer is capable of hybridizing to and amplifying bacterial ITS DNA; d) a forward primer and a reverse primer comprising at least one nucleotide sequence that differs from the corresponding nucleotide sequence of the forward primer or reverse primer of the primer set of (a) in that the primer has up to three nucleotide changes compared to the corresponding sequence, wherein the primer is capable of hybridizing to and amplifying bacterial ITS DNA; and e) a forward primer and a reverse primer comprising nucleotide sequences that are complements of the corresponding nucleotide sequences of the forward primer and reverse primer of a primer set selected from the group consisting of (a)-(d). In one embodiment, the HRM system comprises at least one set of primers comprising a forward primer comprising the sequence of SEQ ID NO:1 and a reverse primer comprising the sequence of SEQ ID NO:2.

In another embodiment, the HRM system further comprises: a) a storage component for storing HRM data, wherein the storage component has instructions for identifying the bacteria by HRM analysis stored therein; b) a computer processor for processing data, wherein the computer processor is coupled to the storage component and configured to execute the instructions stored in the storage component in order to receive HRM data and analyze HRM data according to a machine learning algorithm (e.g., Naive Bayes); and c) a display component for displaying information regarding the identification of the bacteria.

In certain embodiments, the intercalating dye is a fluorescent dye, such as, but not limited to SYBR® GREEN I fluorescent dye (N',N'-dimethyl-N-[4-[(E)-(3-methyl-1,3-benzothiazol-2-ylidene)methyl]-1-phenylquinolin-1-ium-2-yl]-N-propylpropane-1,3-diamine (Thermo Fisher Scientific, Waltham, Mass.)), L-GREEN LCGREEN® fluorescent dye (Idaho Technology, Inc., Salt Lake City, Utah), LCGREEN® PLUS fluorescent dye (Idaho Technology, Inc., Salt Lake City, Utah), RESOLIGHT® fluorescent dye (Roche Diagnostics, Mannheim, Germany), EVAGREEN® fluorescent dye (Biotium, Inc., Hayward, Calif.), CHROMOFY™ fluorescent dye (TATAA Biocenter, Gdteborg, Sweden), and SYTO™ 9 fluorescent dye (Thermo Fisher Scientific, Waltham, Mass.).

In another embodiment, the invention includes a kit for identifying bacteria in a biological sample, the kit comprising an HRM system, as described herein, and written instructions for identifying the bacteria by HRM analysis.

These and other embodiments of the subject invention will readily occur to those of skill in the art in view of the disclosure herein.

BRIEF DESCRIPTION OF THE FIGURES

FIGS. 2A-2F show that ITS provides high information profiles inclusive to the species level. FIG. 2A shows representative 16S and ITS melt curves of seven (7) species of the *Bacillus* genus. FIG. 2B shows 16S and ITS composite melt curves of all 89 bacterial organisms in our library. FIG. 2C shows ITS melt curves of *B. anthracis* and *B. mycoides*. FIG. 2D shows ITS melt curves of *Pseudomonas aeruginosa* and *P. putida* compared to the their undistinguishable 16S counterparts. FIG. 2E shows ITS melt curves of two (2) strains of *B. anthracis* and 2 strains of *Y. pestis*. FIG. 2F shows ITS melt curves of five (5) strains of *S. pneumoniae* for the strain inclusivity test.

FIGS. 3A-3E show heteroduplex analysis of *E. coli* ITS. FIG. 3A shows a Clustal Omega Multiple Sequence Alignment of *E. coli* ATCC 25922 (GenBank Accession number CP009072) ITS short (361 bp, SEQ ID NO:5) and ITS long (453 bp, SEQ ID NO:6) sequences. FIG. 3A (left) shows ITS homoduplex-heteroduplex profiles obtained after 20 (1), 25 (2), 30 (3), 35 (4) and 40 (5) number of PCR cycles. Slow migrating bands were visible starting from cycle number 25, suggesting the heteroduplex nature of the bands. Expected homoduplex bands were at 540 bp (361 bp ITS short+179 bp of 3' of 16S and 38 bp of 5' 23S), and 632 bp (453 bp+179 bp). Lane M contains 100-bp DNA marker. FIG. 3B (right) shows an agarose gel electrophoresis showing *E. coli* ITS PCR products treated (2) and not-treated (1) with mung bean nuclease, an enzyme that recognizes and cleaves single stranded DNA, even when it is located in double-stranded DNA products. The loss of the higher molecular weight bands confirms the heteroduplex nature of the bands, leaving the true homoduplexes. Lane M contains 100-bp DNA marker. FIG. 3C-3E show that ITS HRM analysis on 20 colonies resulted in 2 distinct melt curve groups, ITS short (FIG. 3C) and ITS long (FIG. 3D). FIG. 3E shows a composite. The dark gray curve is the melt curve from mixing one representative colony from each group compared to *E. coli* genomic DNA.

Figures 12, 13:
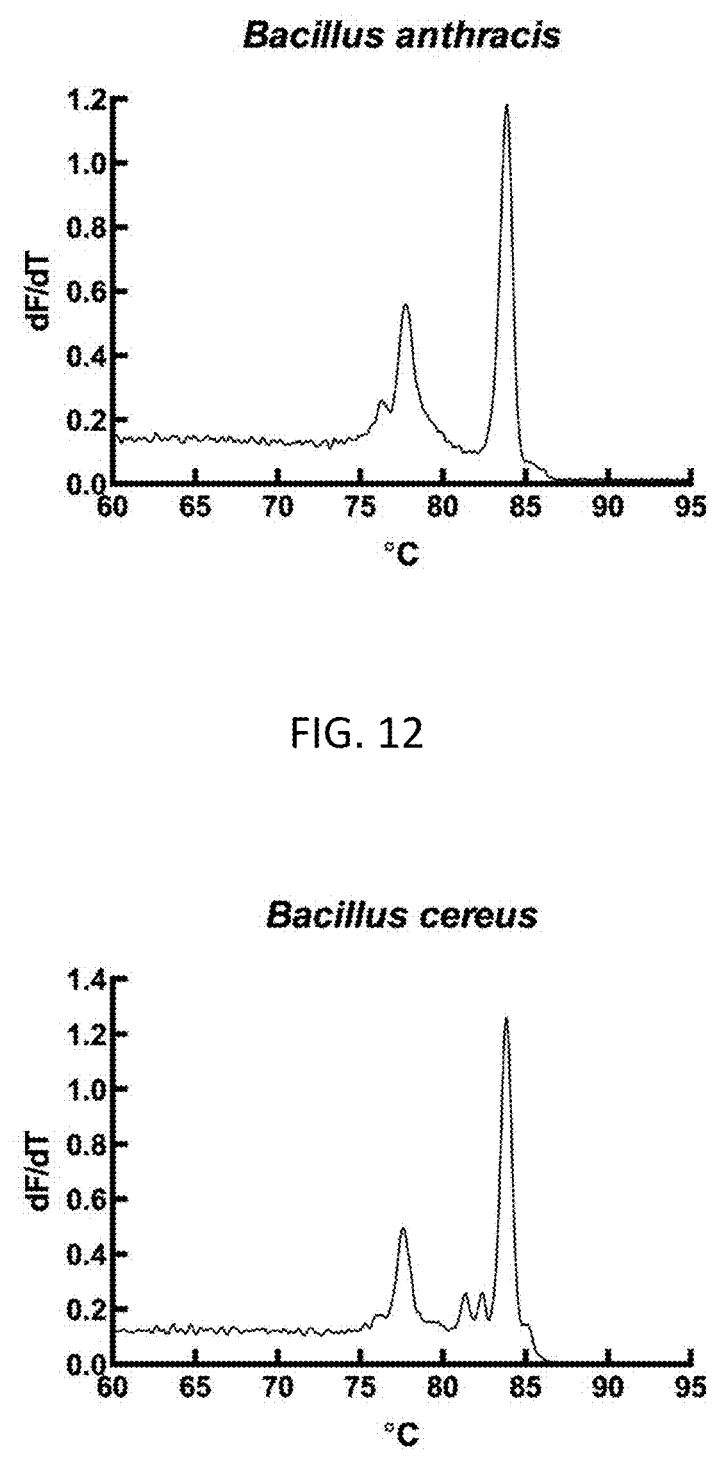

FIG. 12 shows an HRM curve for the ITS region of *Bacillus anthracis*.

FIG. 13 shows an HRM curve for the ITS region of *Bacillus cereus*.

Figures 24, 25:
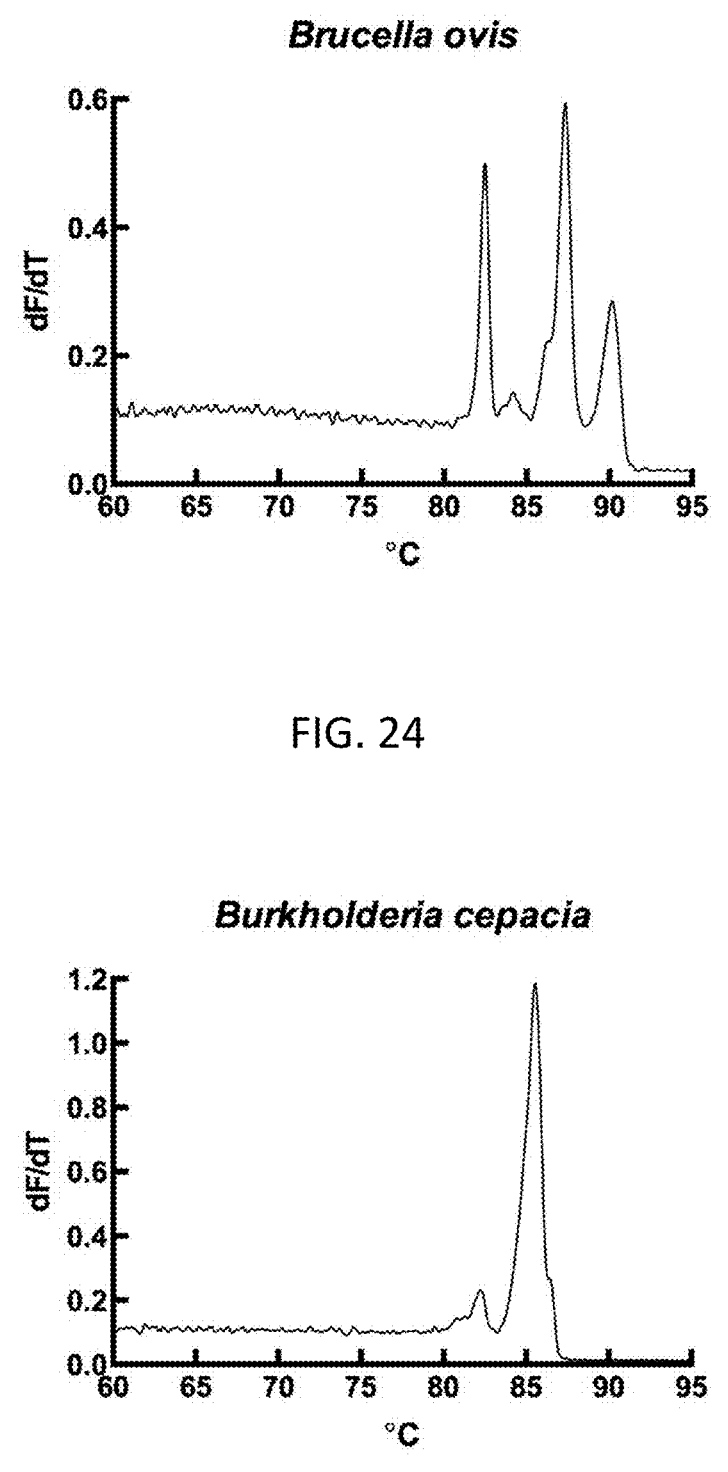

FIG. 24 shows an HRM curve for the ITS region of *Brucella ovis*.

FIG. 25 shows an HRM curve for the ITS region of *Burkholderia cepacia*.

Figures 26, 27:
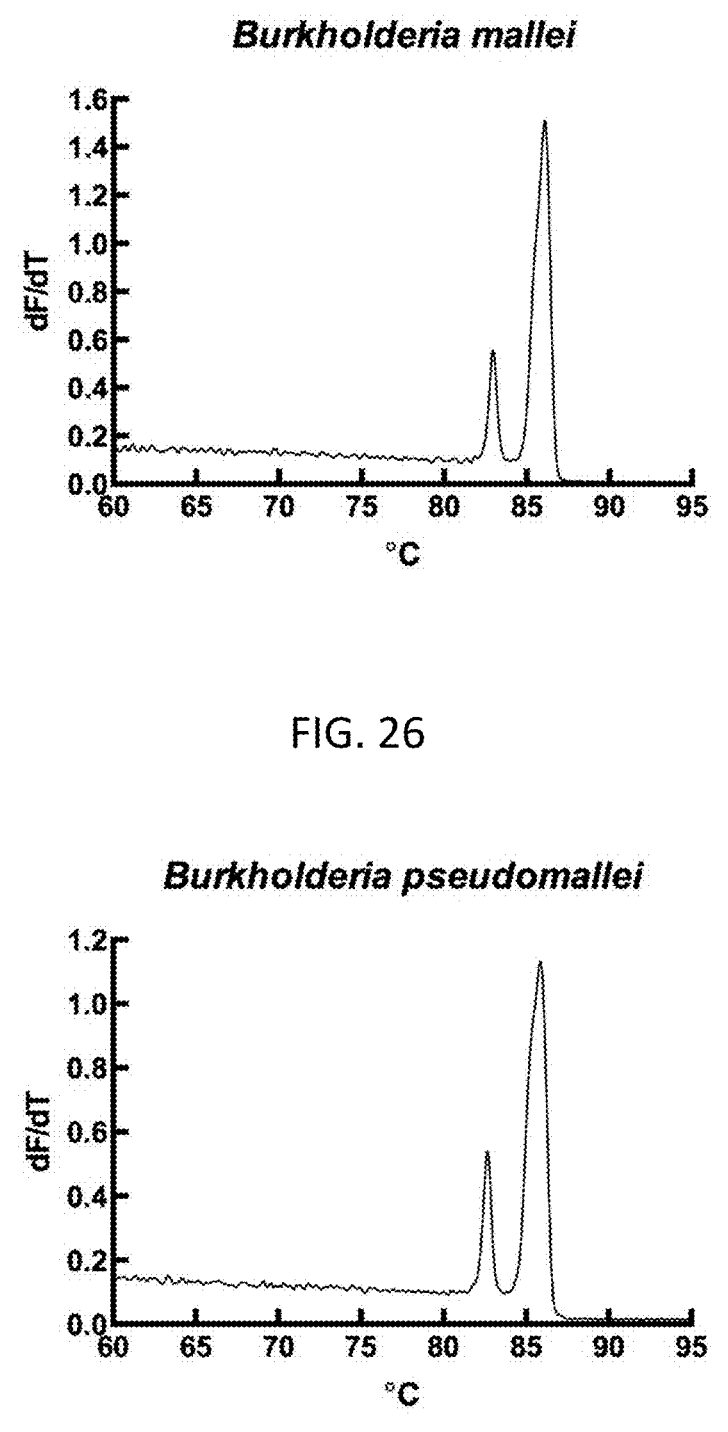

FIG. 26 shows an HRM curve for the ITS region of *Burkholderia mallei*.

FIG. 27 shows an HRM curve for the ITS region of *Burkholderia pseudomallei*.

FIG. 92 shows an HRM curve for the ITS region of *Yersinia pseudotuberculosis*.

DETAILED DESCRIPTION OF THE INVENTION

Figure 1:
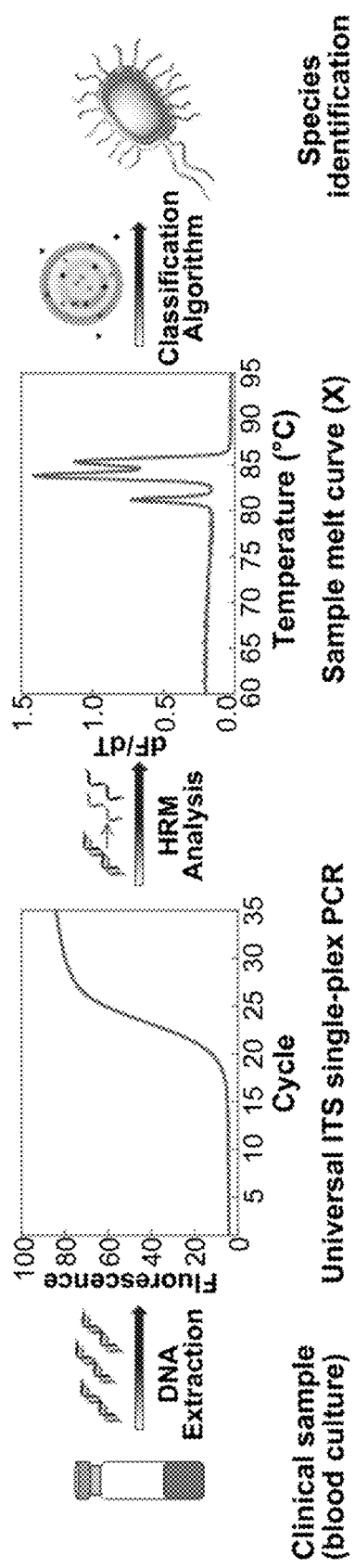
FIG. 1 shows the workflow of our ITS HRM assay. ITS PCR HRM analysis is performed on DNA extracted from clinical samples such as positive blood culture and CSF samples. Our novel classification algorithm then identifies the bacterial pathogens by matching the unknown melt curve against a reference database.

The practice of the present invention will employ, unless otherwise indicated, conventional methods of microbiology, chemistry, biochemistry, molecular biology and recombinant DNA techniques, and immunology, within the skill of the art. Such techniques are explained fully in the literature. See, e.g., *PCR Technology: Current Innovations* (T. Nolan and S. A. Bustin eds., CRC Press, 3$^{rd}$ edition, 2013); *A-Z of Quantitative PCR* (IUL Biotechnology, No. 5, S. A. Bustin ed., International University Line, 2004); Principles and Practice of Clinical Bacteriology (S. Gillespie and P. M. Hawkey eds., Wiley; 2$^{nd}$ edition, 2006); *Diagnostic Bacteriology Protocols* (Methods in Molecular Biology, L. O'Connor ed., Humana Press, 2$^{nd}$ edition, 2006); J. F. Macfaddin *Biochemical Tests for Identification of Medical Bacteria* (Lippincott Williams & Wilkins, 3$_{rd}$ edition, 2000); *Handbook of Experimental Immunology*, Vols. I-IV (D. M. Weir and C. C. Blackwell eds., Blackwell Scientific Publications); A. L. Lehninger, *Biochemistry* (Worth Publishers, Inc., current addition); Sambrook, et al., *Molecular Cloning: A Laboratory Manual* (3$^{rd}$ Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

1. DEFINITIONS

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "an amplicon" includes a mixture of two or more such amplicons, and the like.

"Substantially purified" generally refers to isolation of a substance (compound, polynucleotide, oligonucleotide, protein, or polypeptide) such that the substance comprises the majority percent of the sample in which it resides. Typically in a sample, a substantially purified component comprises 50%, preferably 80%-85%, more preferably 90-95% of the sample. Techniques for purifying polynucleotides oligonucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide or oligonucleotide is a nucleic acid molecule devoid, in whole or part, of sequences normally associated with it in nature; or a sequence, as it exists in nature, but having heterologous sequences in association therewith; or a molecule disassociated from the chromosome.

"Homology" refers to the percent identity between two polynucleotide or two polypeptide molecules. Two nucleic acid, or two polypeptide sequences are "substantially homologous" to each other when the sequences exhibit at least about 50% sequence identity, preferably at least about 75% sequence identity, more preferably at least about 80%-85% sequence identity, more preferably at least about 90% sequence identity, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; *Nucleic Acid Hybridization*, supra.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

As used herein, a "solid support" refers to a solid surface such as a magnetic bead, latex bead, microtiter plate well, glass plate, nylon, agarose, acrylamide, and the like.

As used herein, the term "target nucleic acid region" or "target nucleic acid" denotes a nucleic acid molecule with a "target sequence" to be amplified. The target nucleic acid may be either single-stranded or double-stranded and may include other sequences besides the target sequence, which may not be amplified. The term "target sequence" refers to the particular nucleotide sequence of the target nucleic acid which is to be amplified. The target sequence may include a probe-hybridizing region contained within the target molecule with which a probe will form a stable hybrid under desired conditions. The "target sequence" may also include the complexing sequences to which the oligonucleotide primers complex and are extended using the target sequence as a template. Where the target nucleic acid is originally single-stranded, the term "target sequence" also refers to the sequence complementary to the "target sequence" as present in the target nucleic acid. If the "target nucleic acid" is originally double-stranded, the term "target sequence" refers to both the plus (+) and minus (−) strands (or sense and antisense strands).

The term "primer" or "oligonucleotide primer" as used herein, refers to an oligonucleotide that hybridizes to the template strand of a nucleic acid and initiates synthesis of a nucleic acid strand complementary to the template strand when placed under conditions in which synthesis of a primer extension product is induced, i.e., in the presence of nucleotides and a polymerization-inducing agent such as a DNA or RNA polymerase and at suitable temperature, pH, metal concentration, and salt concentration. The primer is preferably single-stranded for maximum efficiency in amplification, but may alternatively be double-stranded. If double-stranded, the primer can first be treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA or RNA synthesis. Typically, bacterial nucleic acids are amplified using at least one set of oligonucleotide primers comprising at least one forward primer and at least one reverse primer capable of hybridizing to regions of a bacterial nucleic acid flanking the portion of the bacterial nucleic acid (e.g., ITS region) to be amplified.

The term "amplicon" refers to the amplified nucleic acid product of a PCR reaction or other nucleic acid amplification process (e.g., ligase chain reaction (LCR, isoothermal amplification), nucleic acid sequence based amplification (NASBA), transcription-mediated amplification (TMA), Q-beta amplification, strand displacement amplification, or target mediated amplification).

As used herein, the term "probe" or "oligonucleotide probe" refers to a polynucleotide, as defined above, that contains a nucleic acid sequence complementary to a nucleic acid sequence present in the target nucleic acid analyte. The polynucleotide regions of probes may be composed of DNA, and/or RNA, and/or synthetic nucleotide analogs. Probes may be labeled in order to detect the target sequence. Such a label may be present at the 5' end, at the 3' end, at both the 5' and 3' ends, and/or internally. The "oligonucleotide probe" may contain at least one fluorescer and at least one quencher. Quenching of fluorophore fluorescence may be eliminated by exonuclease cleavage of the fluorophore from the oligonucleotide (e.g., TaqMan assay) or by hybridization of the oligonucleotide probe to the nucleic acid target sequence (e.g., molecular beacons). Additionally, the oligonucleotide probe will typically be derived from a sequence that lies between the sense and the antisense primers when used to detect an amplicon.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

It will be appreciated that the hybridizing sequences need not have perfect complementarity to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

The "melting temperature" or "$T_m$" of double-stranded DNA is defined as the temperature at which half of the helical structure of DNA is lost due to heating or other dissociation of the hydrogen bonding between base pairs, for example, by acid or alkali treatment, or the like. The $T_m$ of a DNA molecule depends on its length and on its base composition. DNA molecules rich in GC base pairs have a higher $T_m$ than those having an abundance of AT base pairs. Separated complementary strands of DNA spontaneously reassociate or anneal to form duplex DNA when the temperature is lowered below the $T_m$.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, cells, muscles, joints, organs, biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, semiconductor nanoparticles, dyes, metal ions, metal sols, ligands (e.g., biotin, strepavidin or haptens) and the like. The term "fluorescer" refers to a substance or a portion thereof which is capable of exhibiting fluorescence in the detectable range. Particular examples of labels which may be used in the practice of the invention include, but are not limited to, SYBR® GREEN dye, SYBR® GOLD dye, a CAL FLUOR® dye such as CAL FLUOR® GOLD 540 dye, CAL FLUOR® ORANGE 560 dye, CAL FLUOR® RED 590 dye, CAL FLUOR® RED 610 dye, and CAL FLUOR® RED 635 dye, a QUASAR® dye such as QUASAR® 570 dye, QUASAR® 670 dye, and QUASAR® 705 dye, an ALEXA FLUOR® such as ALEXA FLUOR® 350 dye, ALEXA FLUOR® 488 dye, ALEXA FLUOR® 546 dye, ALEXA FLUOR® 555 dye, ALEXA FLUOR® 594 dye, ALEXA FLUOR® 647 dye, and ALEXA FLUOR® 784 dye, a cyanine dye such as CY®3 dye, CY®3.5 dye, CY®5 dye, CY®5.5 dye, and CY®7 dye, fluorescein, 2', 4', 5', 7'-tetrachloro-4-7-dichlorofluorescein (TET), carboxyfluorescein (FAM), 6-carboxy-4',5'-dichloro-2',7'-dimethoxyfluorescein (JOE), hexachlorofluorescein (HEX), rhodamine, carboxy-X-rhodamine (ROX), tetramethyl rhodamine (TAMRA), FITC, dansyl, umbelliferone, dimethyl acridinium ester (DMAE), Texas red, luminol, NADPH, horseradish peroxidase (HRP), and α-β-galactosidase.

The term "subject" includes both vertebrates and invertebrates, including, without limitation, mammals, including human and non-human mammals such as non-human primates, including chimpanzees and other apes and monkey species; laboratory animals such as mice, rats, rabbits, hamsters, guinea pigs, and chinchillas; domestic animals such as dogs and cats; farm animals such as sheep, goats, pigs, horses and cows; and birds such as domestic, wild and game birds, including chickens, turkeys and other gallinaceous birds, ducks, geese, and the like. The term does not denote a particular age. Thus, both adult and newborn individuals are intended to be covered.

2. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of an HRM-based method for identification of bacteria that provides reliable genomic fingerprinting of eubacterial species. The inventors have shown that HRM analysis of the bacterial hypervariable internal transcribed spacer (ITS) region is useful for distinguishing bacterial species (Example 1). HRM analysis is performed by first amplifying the ITS region of the bacterial genome followed by monitoring thermal DNA melting (i.e., separation of two strands of DNA with heat) of the resulting amplicon with a high resolution instrument. The ITS region exhibits heterogeneity in terms of length, copy number, and sequence in different bacterial species as well as in different alleles of a given species. As a result, ITS amplicons from different bacterial species have complex and distinguishable HRM curve shapes, which allows rapid detection of bacteria by HRM analysis with interspecies and, in some cases, intraspecies discrimination. HRM analysis can be used for diagnosing local infections as well as widespread or systemic infection in patients. The ability to rapidly identify bacterial pathogens by HRM analysis should enable early treatment with appropriate antibiotics and reduce patient morbidity and mortality.

DNA melting can be monitored with a dye that fluoresces in the presence of double-stranded DNA. Fluorescence intensity of the dye decreases with increasing temperature as the DNA denatures into single strands. The dye is typically an intercalating dye that is added before carrying out DNA amplification. The dye preferably saturates the amplicon product, but does not inhibit the DNA amplification reaction. Exemplary dyes that can be used in HRM analysis include, but are not limited to, SYBR® GREEN I fluorescent dye (N',N'-dimethyl-N-[4-[(E)-(3-methyl-1,3-benzothiazol-2-ylidene)methyl]-1-phenylquinolin-1-ium-2-yl]-N-propylpropane-1,3-diamine (Thermo Fisher Scientific, Waltham, Mass.)), LCGREEN® fluorescent dye (Idaho Technology, Inc., Salt Lake City, Utah), LCGREEN® PLUS fluorescent dye (Idaho Technology, Inc., Salt Lake City, Utah), RESOLIGHT® fluorescent dye (Roche Diagnostics, Mannheim, Germany), EVAGREEN® fluorescent dye (Biotium, Inc., Hayward, Calif.), CHROMOFY™ fluorescent dye (TATAA Biocenter, Gdteborg, Sweden), and SYTO™ 9 fluorescent dye (Thermo Fisher Scientific, Waltham, Mass.). For a description of devices and methods for performing HRM analysis, see, e.g., Reed et al. (2007) Pharmacogenomics 8(6):597-608, Druml et al. (2014) Food Chem. 158:245-254; Er et al. (2012) Clin. Chim. Acta 414:197-201; Tong et al. (2012) J. Clin. Microbiol. 50(11):3418-3421, Wittwer et al. (2009) Hum. Mutat. 30(6):857-859, Vossen et al. (2009) Hum. Mutat. 30(6):860-866, and Erali et al. (2008) Exp. Mol. Pathol. 85(1):50-58; herein incorporated by reference in their entireties.

The melting profile of an ITS amplicon depends on the GC content, length, sequence and copy number variation of the bacterial ITS region. Differences among bacteria in sequence and copy number variation within the ITS region alter the formation of heteroduplexes resulting in changes in the shape of the melting curve and melting temperature ($T_m$). Thus, HRM analysis can be used to identify bacteria in a biological sample by comparing the melt curve of an amplicon of genomic ITS DNA from the bacteria to reference melt curves for amplicons of genomic ITS DNA from known bacterial species, wherein different bacterial species are distinguished by differences in melt curve shape and melting temperature ($T_m$), and the bacteria is identified by finding a matching reference HRM curve.

HRM analysis is useful for detecting bacteria in biological samples such as blood samples, including without limitation, in whole blood, serum and plasma. Bacteria can also be detected in other fluid or tissue samples including, but not limited to, saliva, cerebrospinal fluid (CSF), mucus, lymph fluid, or lavage fluid, and tissue samples obtained from skin and soft tissue. In particular, fluid or tissue samples may be obtained from infected organs such as organs of the respiratory system, reproductive system, nervous system, muscular system, integumentary system, lymphatic system, excretory system, endocrine system, digestive system, cardiovascular system, and skeletal system. In addition, bacteria can be specifically detected and identified from samples taken from the site of a localized infection, for example, at the site of a wound caused by a traumatic injury or surgery. If desired, bacteria from a biological sample may be cultured prior to amplification of the bacterial nucleic acids.

An amplification method such as PCR, ligase chain reaction (LCR), or isothermal amplification can be used to amplify the ITS region from bacterial genomic DNA. These methods use oligonucleotide primers capable of amplifying at least a portion or the entire ITS region of a bacterial genome. Typically, primer oligonucleotides are in the range of between 10-100 nucleotides in length, such as 15-60, 20-40 and so on, more typically in the range of between 15-25 nucleotides long, and any length between the stated ranges. In certain embodiments, a primer oligonucleotide comprises a sequence selected from the group consisting of SEQ ID NO:1 and SEQ ID NO:2; or a fragment thereof comprising at least about 6 contiguous nucleotides, preferably at least about 8 contiguous nucleotides, more preferably at least about 10-12 contiguous nucleotides, and even more preferably at least about 13-16 contiguous nucleotides; or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto. Changes to the nucleotide sequences of SEQ ID NO:1 and SEQ ID NO:2 may be introduced corresponding to genetic variations in particular bacterial strains of interest. In certain embodiments, up to three nucleotide changes, including 1 nucleotide change, 2 nucleotide changes, or three nucleotide changes, may be made in a sequence selected from the group consisting of SEQ ID NO:1 and SEQ ID NO:2, wherein the oligonucleotide primer is capable of hybridizing to and amplifying a bacterial ITS target DNA sequence.

Oligonucleotides may be coupled to labels for detection. There are several means known for derivatizing oligonucleotides with reactive functionalities which permit the addition of a label. For example, several approaches are available for biotinylating oligonucleotides so that radioactive, fluorescent, chemiluminescent, enzymatic, or electron dense labels can be attached via avidin. See, e.g., Broken et al., *Nucl. Acids Res*. (1978) 5:363-384 which discloses the use of ferritin-avidin-biotin labels; and Chollet et al., *Nucl. Acids Res*. (1985) 13:1529-1541 which discloses biotinylation of the 5' termini of oligonucleotides via an aminoalkylphosphoramide linker arm. Several methods are also available for synthesizing amino-derivatized oligonucleotides which are readily labeled by fluorescent or other types of compounds derivatized by amino-reactive groups, such as isothiocyanate, N-hydroxysuccinimide, or the like, see, e.g., Connolly, *Nucl. Acids Res*. (1987) 15:3131-3139, Gibson et al. *Nucl. Acids Res*. (1987) 15:6455-6467 and U.S. Pat. No. 4,605,735 to Miyoshi et al. Methods are also available for synthesizing sulfhydryl-derivatized oligonucleotides, which can be reacted with thiol-specific labels, see, e.g., U.S. Pat. No. 4,757,141 to Fung et al., Connolly et al., *Nucl. Acids Res*. (1985) 13:4485-4502 and Spoat et al. *Nucl. Acids Res*. (1987) 15:4837-4848. A comprehensive review of methodologies for labeling DNA fragments is provided in Matthews et al., *Anal. Biochem*. (1988) 169:1-25.

For example, oligonucleotides may be fluorescently labeled by linking a fluorescent molecule to the non-ligating terminus of the molecule. Guidance for selecting appropriate fluorescent labels can be found in Smith et al., *Meth. Enzymol*. (1987) 155:260-301; Karger et al., *Nucl. Acids*

Res. (1991) 19:4955-4962; Guo et al. (2012) *Anal. Bioanal. Chem.* 402(10):3115-3125; and *Molecular Probes Handbook, A Guide to Fluorescent Probes and Labeling Technologies,* 11th edition, Johnson and Spence eds., 2010 (Molecular Probes/Life Technologies). Fluorescent labels include fluorescein and derivatives thereof, such as disclosed in U.S. Pat. No. 4,318,846 and Lee et al., *Cytometry* (1989) 10:151-164. Dyes for use in the present invention include 3-phenyl-7-isocyanatocoumarin, acridines, such as 9-isothiocyanatoacridine and acridine orange, pyrenes, benzoxadiazoles, and stilbenes, such as disclosed in U.S. Pat. No. 4,174,384. Additional dyes include SYBR® GREEN dye, SYBR® GOLD dye, YAKIMA YELLOW® dye, Texas Red, 3-(ε-carboxypentyl)-3'-ethyl-5,5'-dimethyloxa-carbocyanine (CYA); 6-carboxy fluorescein (FAM); CAL FLUOR® ORANGE 560 dye, CAL FLUOR® RED 610 dye, QUASAR® BLUE 670 dye; 5,6-carboxyrhodamine-110 (R110); 6-carboxyrhodamine-6G (R6G); N',N',N',N'-tetramethyl-6-carboxyrhodamine (TAMRA); 6-carboxy-X-rhodamine (ROX); 2', 4', 5', 7',-tetrachloro-4-7-dichlorofluorescein (TET); 2', 7'-dimethoxy-4', 5'-6 carboxyrhodamine (JOE); 6-carboxy-2',4,4',5',7,7'-hexachlorofluorescein (HEX); DRAGONFLY ORANGE™ dye; ATTO-TEC dye; BODIPY® boron-dipyrromethene dye; ALEXA® dye; VIC dye, CY®3 dye, and CY®5 dye. These dyes are commercially available from various suppliers such as Life Technologies (Carlsbad, Calif.), Biosearch Technologies (Novato, Calif.), and Integrated DNA Technolgies (Coralville, Iowa). Fluorescent labels include fluorescein and derivatives thereof, such as disclosed in U.S. Pat. No. 4,318,846 and Lee et al., *Cytometry* (1989) 10:151-164, and 6-FAM, JOE, TAMRA, ROX, HEX-1, HEX-2, ZOE, TET-1 or NAN-2, and the like.

As explained above, the primers are used in polymerase chain reaction (PCR)-based techniques, to produce an amplicon of the bacterial ITS region. PCR is a technique for amplifying a desired target nucleic acid sequence contained in a nucleic acid molecule or mixture of molecules. In PCR, a pair of primers is employed in excess to hybridize to the complementary strands of the target nucleic acid. The primers are each extended by a polymerase using the target nucleic acid as a template. The extension products become target sequences themselves after dissociation from the original target strand. New primers are then hybridized and extended by a polymerase, and the cycle is repeated to geometrically increase the number of target sequence molecules. The PCR method for amplifying target nucleic acid sequences in a sample is well known in the art and has been described in, e.g., Innis et al. (eds.) *PCR Protocols* (Academic Press, NY 1990); Taylor (1991) *Polymerase chain reaction: basic principles and automation, in PCR: A Practical Approach,* McPherson et al. (eds.) IRL Press, Oxford; Saiki et al. (1986) *Nature* 324:163; as well as in U.S. Pat. Nos. 4,683,195, 4,683,202 and 4,889,818, all incorporated herein by reference in their entireties.

In particular, PCR uses relatively short oligonucleotide primers which flank the target nucleotide sequence to be amplified, oriented such that their 3' ends face each other, each primer extending toward the other. The polynucleotide sample is extracted and denatured, preferably by heat, and hybridized with first and second primers that are present in molar excess. Polymerization is catalyzed in the presence of the four deoxyribonucleotide triphosphates (dNTPs—dATP, dGTP, dCTP and dTTP) using a primer- and template-dependent polynucleotide polymerizing agent, such as any enzyme capable of producing primer extension products, for example, *E. coli* DNA polymerase I, Klenow fragment of DNA polymerase I, T4 DNA polymerase, thermostable DNA polymerases isolated from *Thermus aquaticus* (Taq), available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs). This results in two "long products" which contain the respective primers at their 5' ends covalently linked to the newly synthesized complements of the original strands. The reaction mixture is then returned to polymerizing conditions, e.g., by lowering the temperature, inactivating a denaturing agent, or adding more polymerase, and a second cycle is initiated. The second cycle provides the two original strands, the two long products from the first cycle, two new long products replicated from the original strands, and two "short products" replicated from the long products. The short products have the sequence of the target sequence with a primer at each end. On each additional cycle, an additional two long products are produced, and a number of short products equal to the number of long and short products remaining at the end of the previous cycle. Thus, the number of short products containing the target sequence grows exponentially with each cycle. Preferably, PCR is carried out with a commercially available thermal cycler that incorporates high resolution melting analysis (e.g., the Rotor-Gene Q thermal cycler from Qiagen (Germantown, Md.), Light-Scanner from BioFire Diagnostics Inc. (Salt Lake City, Utah), and LightCycler 480 from Hoffmann-La Roche (Basel, Switzerland)).

The Ligase Chain Reaction (LCR) is an alternate method for nucleic acid amplification. In LCR, probe pairs are used which include two primary (first and second) and two secondary (third and fourth) probes, all of which are employed in molar excess to the target. The first probe hybridizes to a first segment of the target strand, and the second probe hybridizes to a second segment of the target strand, the first and second segments being contiguous so that the primary probes abut one another in 5' phosphate-3' hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. If the target is initially double stranded, the secondary probes also will hybridize to the target complement in the first instance. Once the ligated strand of primary probes is separated from the target strand, it will hybridize with the third and fourth probes which can be ligated to form a complementary, secondary ligated product. It is important to realize that the ligated products are functionally equivalent to either the target or its complement. By repeated cycles of hybridization and ligation, amplification of the target sequence is achieved. This technique is described more completely in EPA 320,308 to K. Backman published Jun. 16, 1989 and EPA 439,182 to K. Backman et al., published Jul. 31, 1991, both of which are incorporated herein by reference.

In some instances, amplification may be carried out under isothermal conditions, e.g., by means of isothermal amplification. Methods of isothermal amplification generally make use of enzymatic means of separating DNA strands to facilitate amplification at constant temperature, such as, e.g., strand-displacing polymerase or a helicase, thus negating the need for thermocycling to denature DNA. Any convenient and appropriate means of isothermal amplification may be employed in the subject methods including but are not limited to: loop-mediated isothermal amplification (LAMP), strand displacement amplification (SDA), helicase-dependent amplification (HDA), nicking enzyme amplification reaction (NEAR), and the like. LAMP generally utilizes a plurality of primers, e.g., 4-6 primers, which may recognize a plurality of distinct regions, e.g., 6-8 distinct regions, of target DNA. Synthesis is generally initiated by a strand-displacing DNA polymerase with two of the primers forming loop structures to facilitate subsequent rounds of amplification. LAMP is rapid and sensitive. In addition, the magnesium pyrophosphate produced during the LAMP amplification reaction may, in some instances be visualized without the use of specialized equipment, e.g., by eye. SDA generally involves the use of a strand-displacing DNA polymerase (e.g., Bst DNA polymerase, Large (Klenow) Fragment polymerase, Klenow Fragment (3'-5' exo-), and the like) to initiate at nicks created by a strand-limited restriction endonuclease or nicking enzyme at a site contained in a primer. In SDA, the nicking site is generally regenerated with each polymerase displacement step, resulting in exponential amplification. HDA generally employs: a helicase which unwinds double-stranded DNA unwinding to separate strands; primers, e.g., two primers, that may anneal to the unwound DNA; and a strand-displacing DNA polymerase for extension. NEAR generally involves a strand-displacing DNA polymerase that initiates elongation at nicks, e.g., created by a nicking enzyme. NEAR is rapid and sensitive, quickly producing many short nucleic acids from a target sequence.

In some cases, a biological sample may contain more than one species of bacteria in need of identification. HRM analysis can be performed on DNA from each bacterial species separately by isolating individual species of bacteria from the biological sample. This can be accomplished by diluting the biological sample and isolating a single species of bacteria in a small volume (i.e., portion of biological sample) before performing amplification and HRM analysis. A biological sample can be fractionated, for example, using microfluidic droplet technology to allow compartmentalization of amplification reactions of ITS DNA from different bacteria or even individual bacterial cells and subsequent HRM analysis. For a description of microfluidic droplet technology and its applications to PCR (e.g., microfluidic droplet PCR or droplet digital PCR (ddPCR)) and HRM analysis, see, e.g., Zhu et al. (2012) Anal. Bioanal. Chem. 403(8):2127-2143, Chong et al. (2015) Lab Chip 16(1):35-58, Basova et al. (2015) Analyst 140(1):22-38, Athamanolap et al. (2013) J. Lab Autom. 19(3):304-312, Taira et al. (2013) Clin. Chim. Acta 424:39-46, and Song et al. (2015) Clin. Chem. 61(11):1354-1362; herein incorporated by reference in their entireties.

HRM analysis may be performed on one or more other phylogenetic loci in addition to the ITS region to assist in identification or to confirm identification of a bacterial species. For example, further HRM analysis may be performed on the 16S rRNA, 23S rRNA, or rpo loci in the bacterial DNA, or any combination thereof.

HRM analysis can be combined with any other method known in the art for identifying and classifying bacteria. For example, the use of microscopy and distinguishing clinical characteristics may aid in diagnosis. Bacterial DNA may be sequenced to confirm the identification of the bacterial species and pinpoint the source of the infection to a specific bacterial strain.

As is readily apparent, the design of assays for detection and identification of bacteria, as described herein, is subject to a great deal of variation. The above descriptions are merely provided as guidance, and one of skill in the art can readily modify the described protocols, using techniques well known in the art.

The above-described reagents including the primers, intercalating dyes, and/or other reagents for performing amplification of bacterial ITS genomic DNA, such as by PCR or LCR, and HRM analysis of the resulting ITS amplicon can be provided in kits, with suitable instructions and other necessary reagents for detection and identification of bacteria as described herein. The kit will normally contain in separate containers the primers and dyes, reference or calibration standards (e.g., low temperature calibrator reference DNA), and other reagents that are required. Instructions (e.g., written, CD-ROM, DVD, flash drive, etc.) for carrying out HRM analysis of bacteria usually will be included in the kit. The kit can also contain, depending on the particular assay used, other packaged reagents and materials (i.e., wash buffers, and the like). HRM analysis of bacteria, such as described herein, can be conducted using these kits.

In certain embodiments, the kit comprises at least one set of primers wherein the primers are not more than about 40 nucleotides in length, wherein the set of primers is selected from the group consisting of: a) a forward primer comprising the nucleotide sequence of SEQ ID NO:1 and a reverse primer comprising the sequence of SEQ ID NO:2; b) a forward primer comprising at least 10 contiguous nucleotides of the nucleotide sequence of SEQ ID NO:1 and a reverse primer comprising at least 10 contiguous nucleotides of the nucleotide sequence of SEQ ID NO:2; c) a forward primer comprising a nucleotide sequence having at least 95% identity to the sequence of SEQ ID NO:1 and a reverse primer comprising a nucleotide sequence having at least 95% identity to the sequence of SEQ ID NO:2, wherein the primer is capable of hybridizing to and amplifying bacterial ITS DNA; d) a forward primer and a reverse primer comprising at least one nucleotide sequence that differs from the corresponding nucleotide sequence of the forward primer or reverse primer of the primer set of (a) in that the primer has up to three nucleotide changes compared to the corresponding sequence, wherein the primer is capable of hybridizing to and amplifying bacterial ITS DNA; and e) a forward primer and a reverse primer comprising nucleotide sequences that are complements of the corresponding nucleotide sequences of the forward primer and reverse primer of a primer set selected from the group consisting of (a)-(d). In one embodiment, the kit comprises a forward primer comprising the nucleotide sequence of SEQ ID NO:1 and a reverse primer comprising the sequence of SEQ ID NO:2. In another embodiment, the kit further comprises an intercalating dye selected from the group consisting of SYBR® GREEN I fluorescent dye (N',N'-dimethyl-N-[4-[(E)-(3-methyl-1,3-benzothiazol-2-ylidene)methyl]-1-phenylquinolin-1-ium-2-yl]-N-propylpropane-1,3-diamine (Thermo Fisher Scientific, Waltham, Mass.)), LCGREEN® fluorescent dye (Idaho Technology, Inc., Salt Lake City, Utah), LCGREEN® PLUS fluorescent dye (Idaho Technology, Inc., Salt Lake City, Utah), RESOLIGHT® fluorescent dye (Roche Diagnostics, Mannheim, Germany), EVAGREEN® fluorescent dye (Biotium, Inc., Hayward, Calif.), CHROMOFY™ fluorescent dye (TATAA Biocenter, Goteborg, Sweden), and SYTO™ 9 fluorescent dye (Thermo Fisher Scientific, Waltham, Mass.).

In another aspect, the invention includes a database comprising reference HRM curves for known bacterial species. The HRM curves for known bacterial species may be divided into a variety of categories or classifications.

Figure 4:
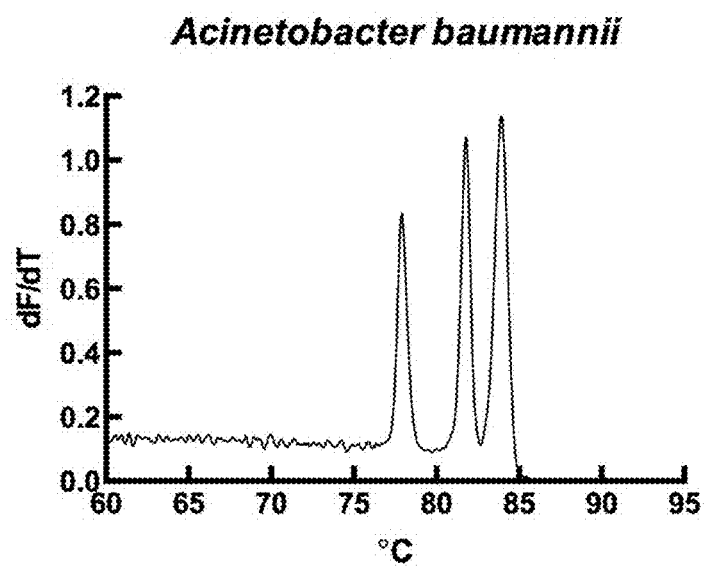
FIG. 4 shows an HRM curve for the ITS region of *Acinetobacter baumannii*.
Figure 5:
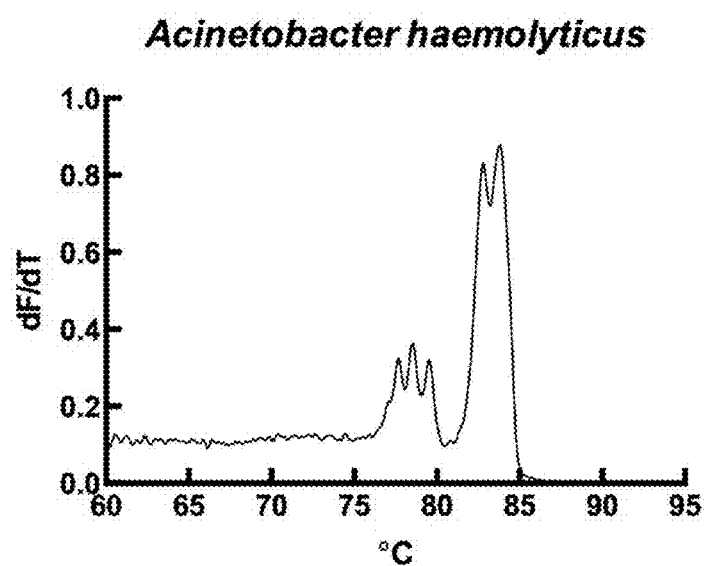
FIG. 5 shows an HRM curve for the ITS region of *Acinetobacter haemolyticus*.
Figure 6:
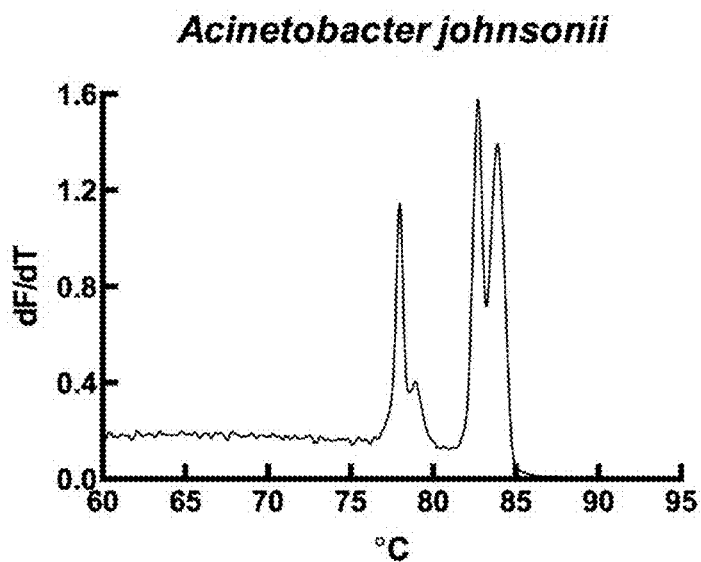
FIG. 6 shows an HRM curve for the ITS region of *Acinetobacter johnsonii*.
Figure 7:
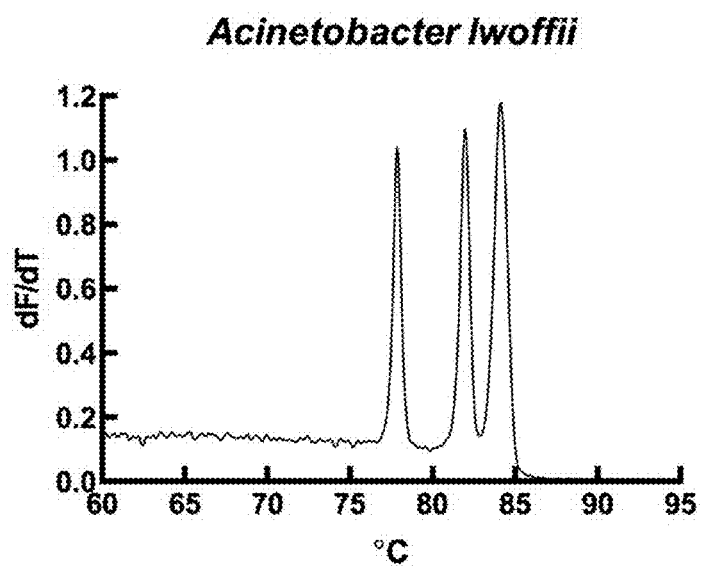
FIG. 7 shows an HRM curve for the ITS region of *Acinetobacter lwoffii*.
Figure 8:
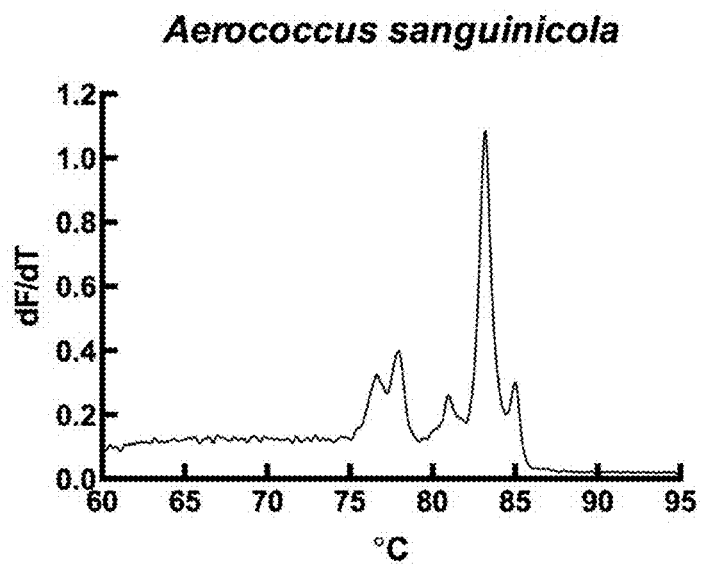
FIG. 8 shows an HRM curve for the ITS region of *Aerococcus sanguinicola*.
Figure 9:
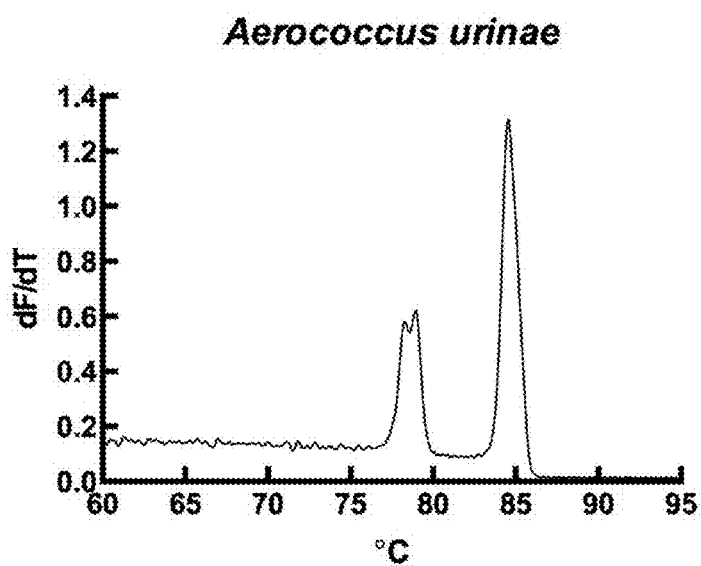
FIG. 9 shows an HRM curve for the ITS region of *Aerococcus urinae*.
Figure 10:
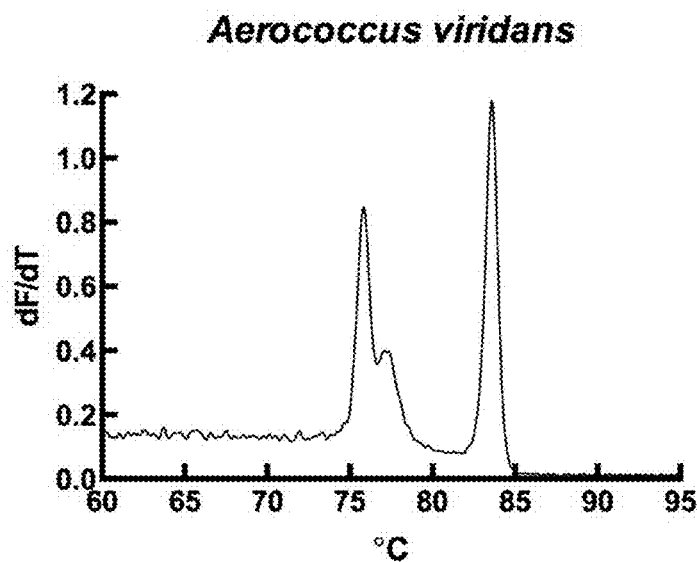
FIG. 10 shows an HRM curve for the ITS region of *Aerococcus viridans*.
Figure 11:
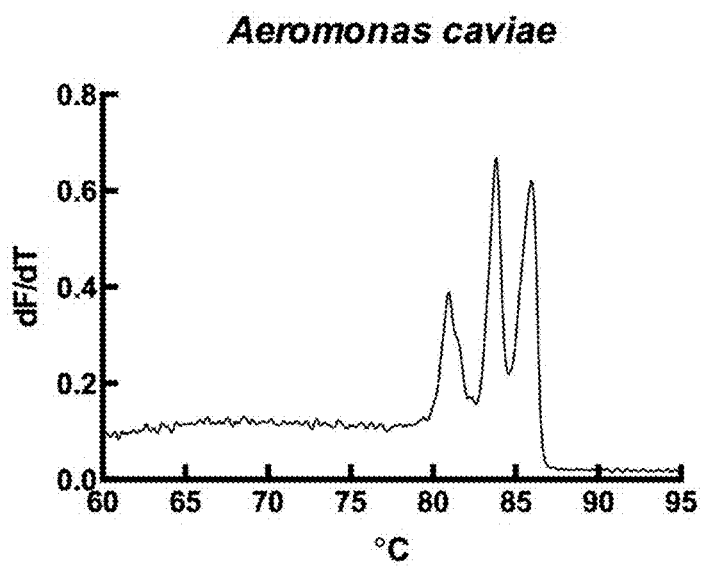
FIG. 11 shows an HRM curve for the ITS region of *Aeromonas caviae*.
Figure 14:
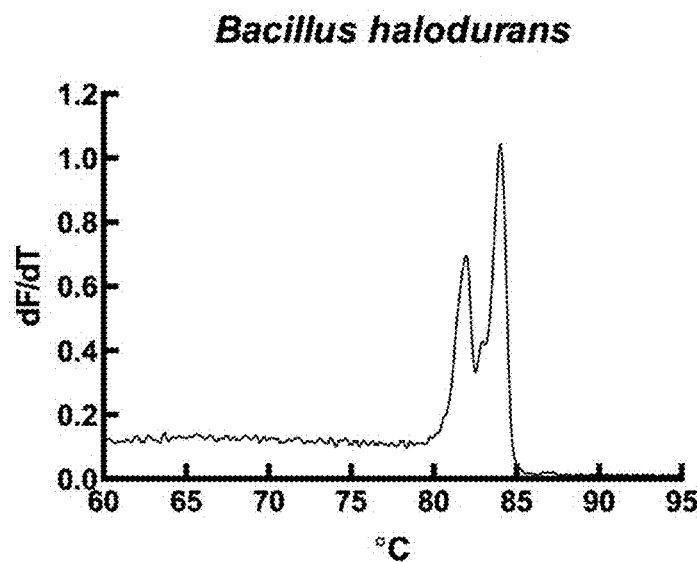
FIG. 14 shows an HRM curve for the ITS region of *Bacillus halodurans*.
Figure 15:
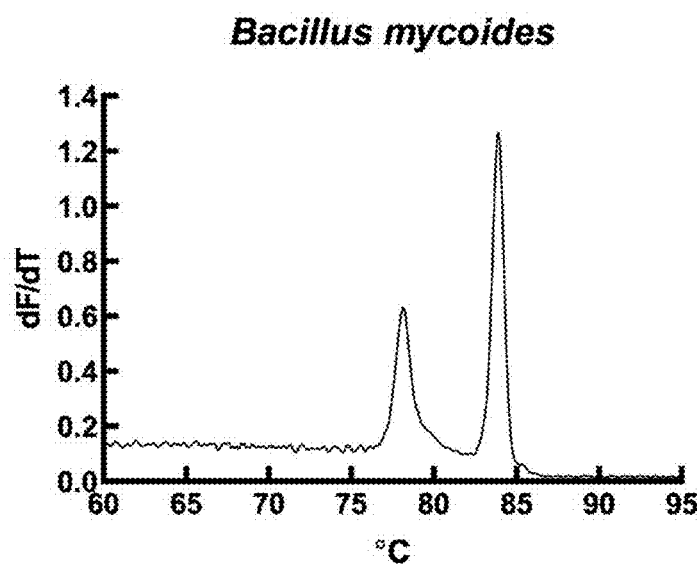
FIG. 15 shows an HRM curve for the ITS region of *Bacillus mycoides*.
Figure 16:
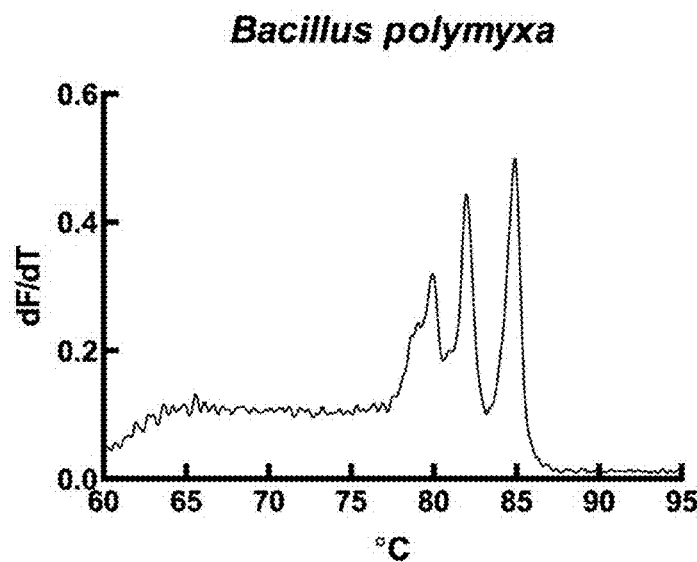
FIG. 16 shows an HRM curve for the ITS region of *Bacillus polymyxa*.
Figure 17:
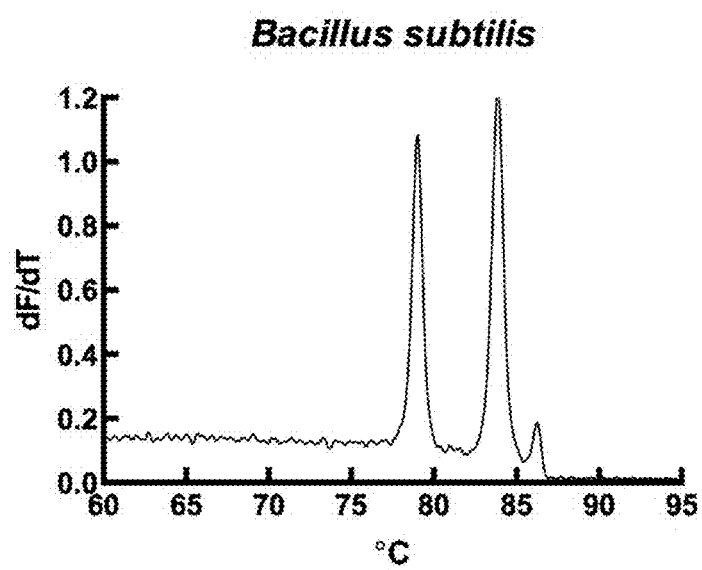
FIG. 17 shows an HRM curve for the ITS region of *Bacillus subtilis*.
Figure 18:
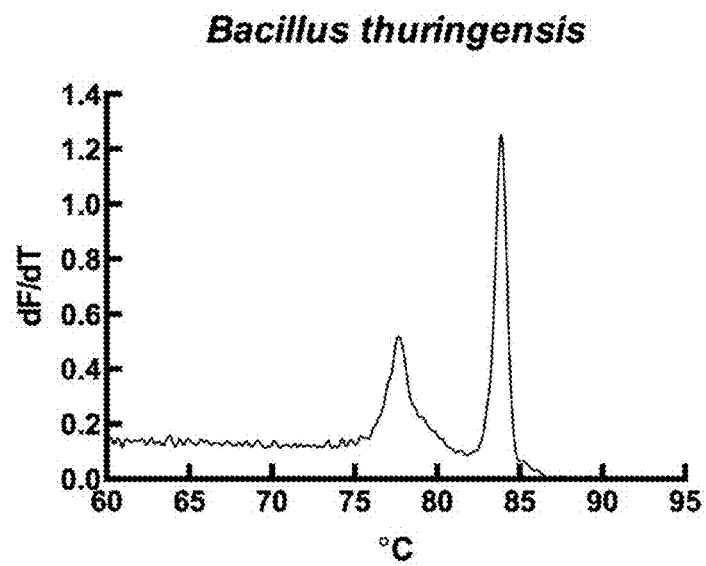
FIG. 18 shows an HRM curve for the ITS region of *Bacillus thuringensis*.
Figure 19:
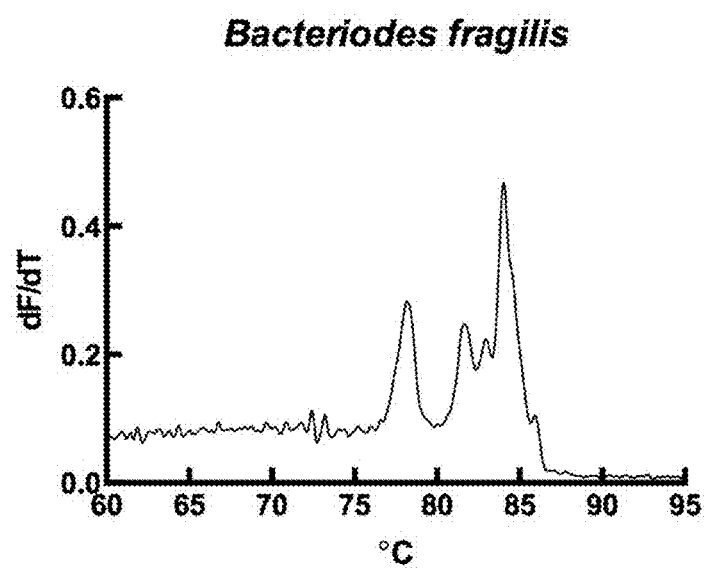
FIG. 19 shows an HRM curve for the ITS region of *Bacteroides fragilis*.
Figure 20:
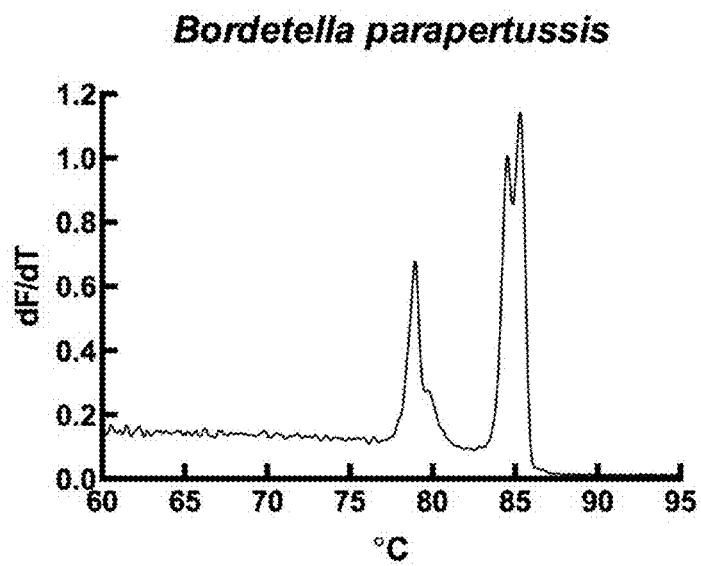
FIG. 20 shows an HRM curve for the ITS region of *Bordetella parapertussis*.
Figure 21:
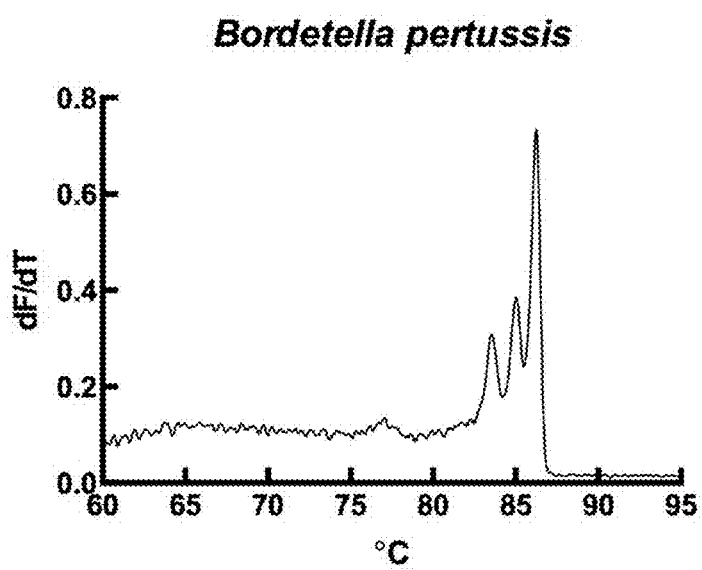
FIG. 21 shows an HRM curve for the ITS region of *Bordetella pertussis*.
Figure 22:
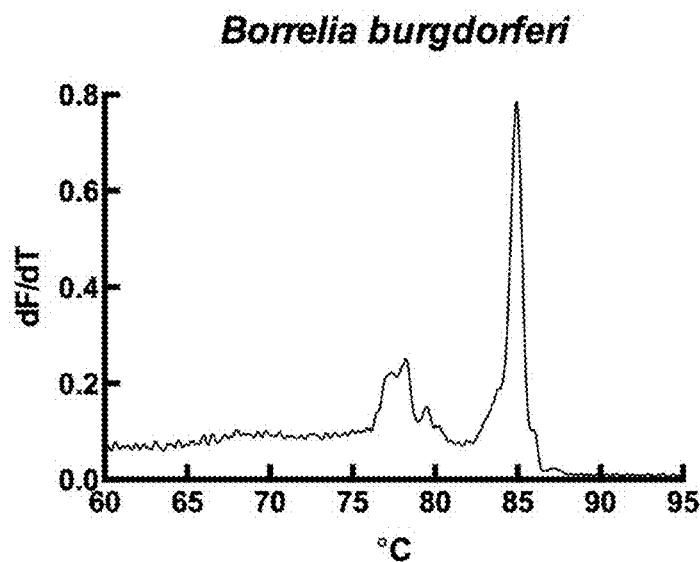
FIG. 22 shows an HRM curve for the ITS region of *Borrelia burgdorferi*.
Figure 23:
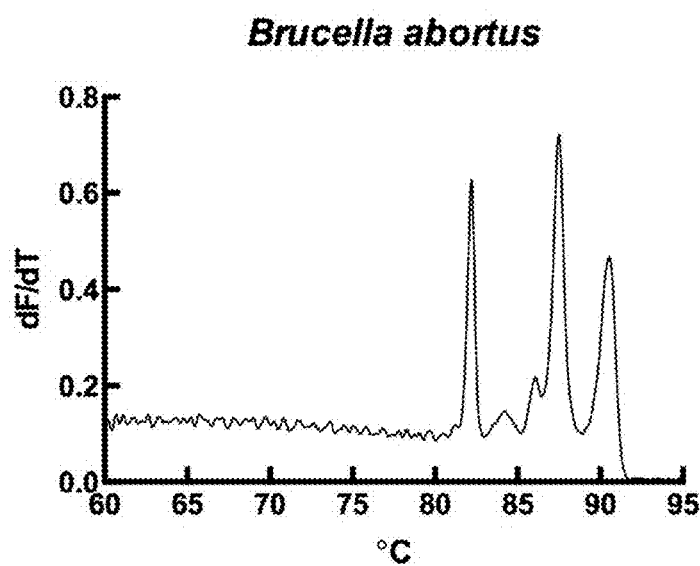
FIG. 23 shows an HRM curve for the ITS region of *Brucella abortus*.
Figure 28:
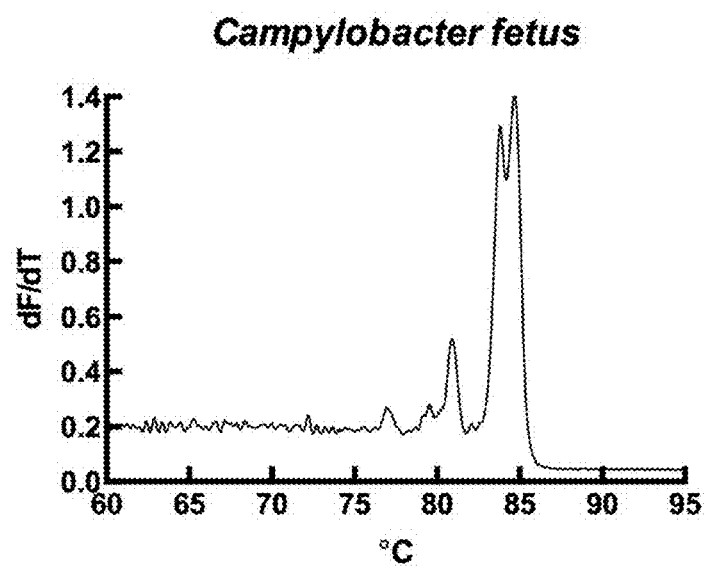
FIG. 28 shows an HRM curve for the ITS region of *Campylobacter fetus*.
Figure 29:
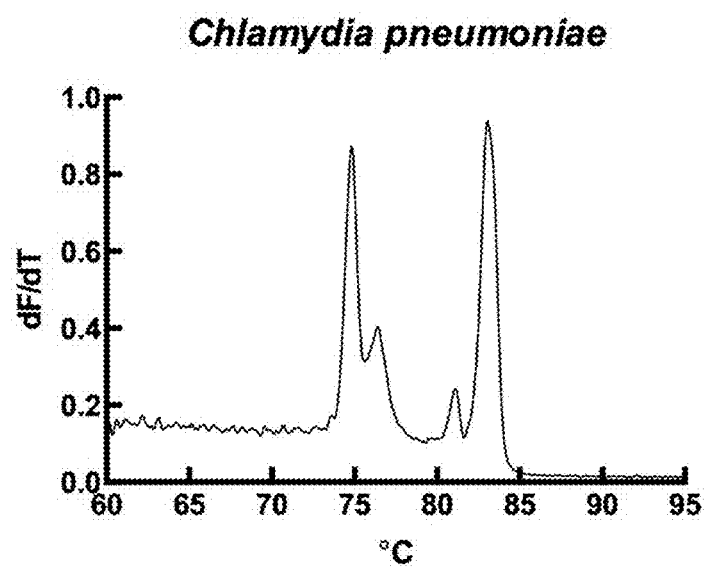
FIG. 29 shows an HRM curve for the ITS region of *Chlamydia pneumoniae*.
Figure 30:
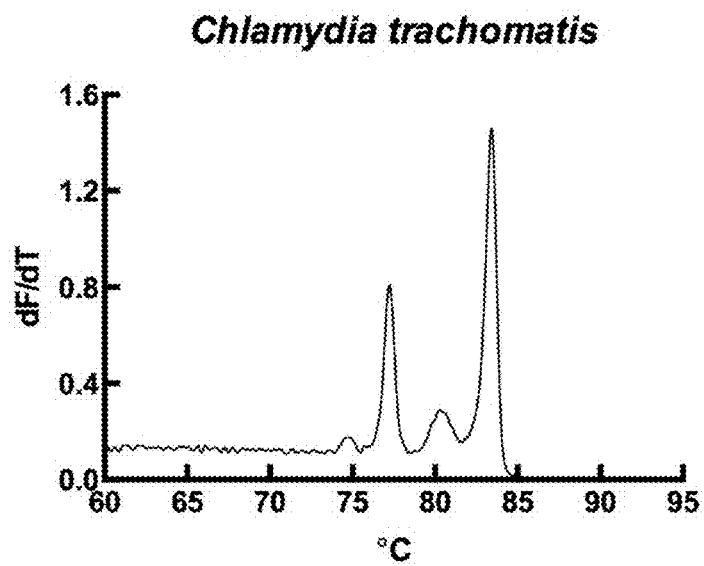
FIG. 30 shows an HRM curve for the ITS region of *Chlamydia trachomatis*.
Figure 31:
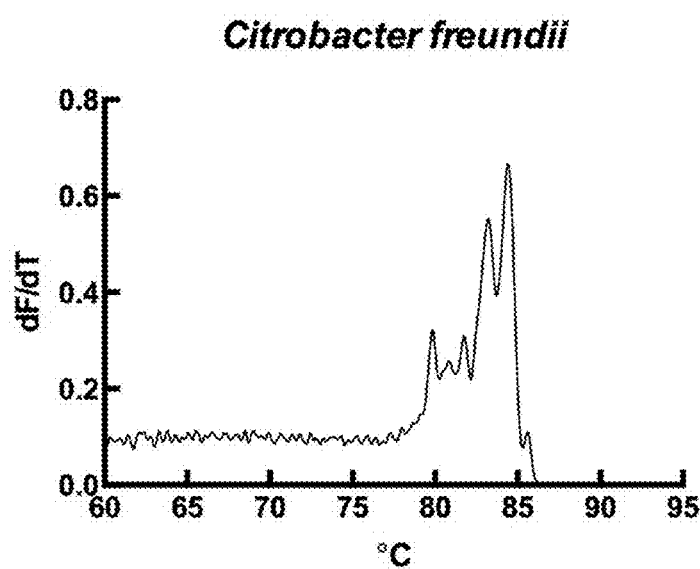
FIG. 31 shows an HRM curve for the ITS region of *Citrobacter freundii*.
Figure 32:
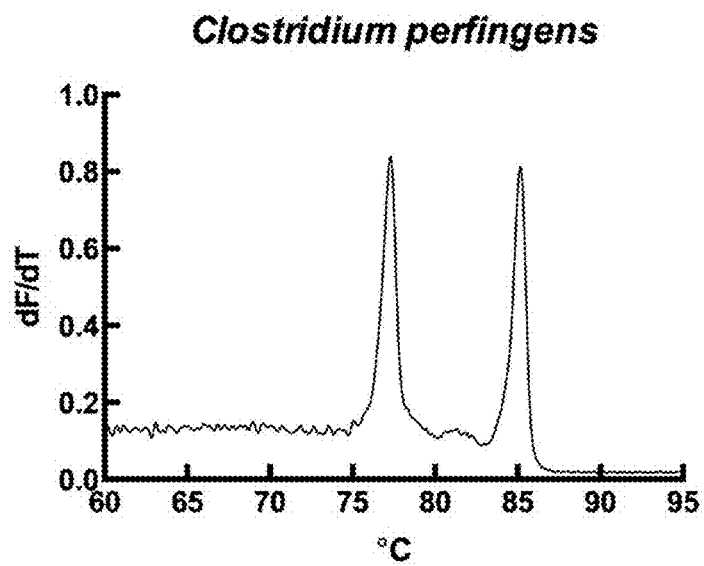
FIG. 32 shows an HRM curve for the ITS region of *Clostridium perfingens*.
Figure 33:
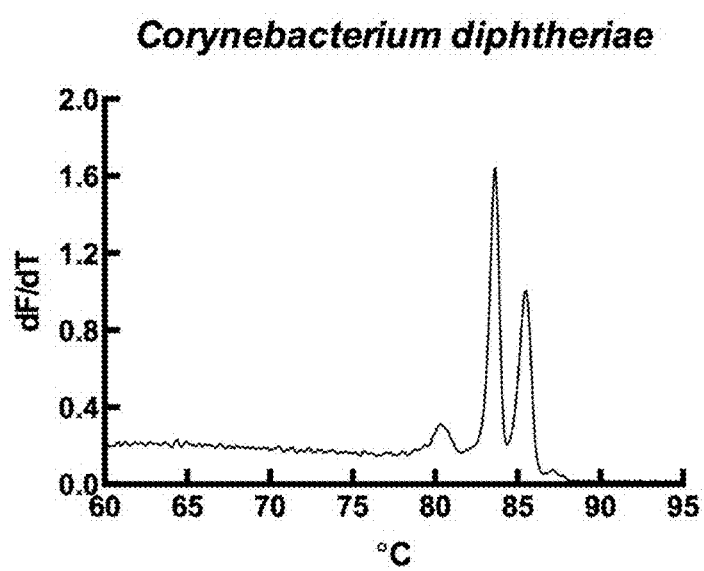
FIG. 33 shows an HRM curve for the ITS region of *Corynebacterium diphtherias*.
Figure 34:
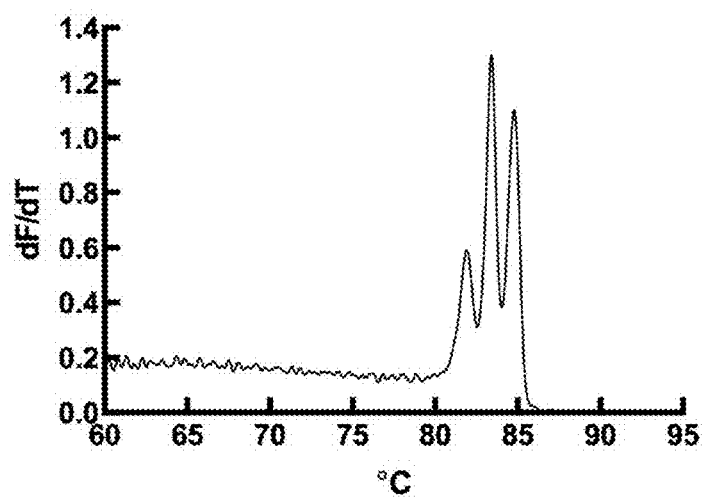
FIG. 34 shows an HRM curve for the ITS region of *Corynebacterium jeikeium*.
Figure 35:
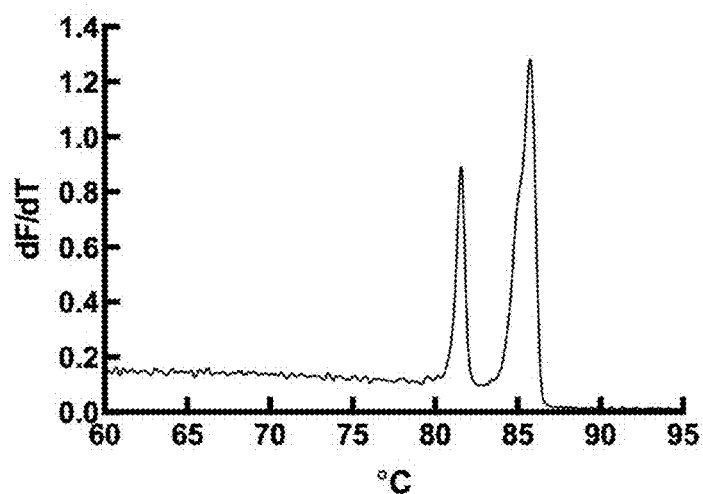
FIG. 35 shows an HRM curve for the ITS region of *Eikenella corrodens*.
Figure 36:
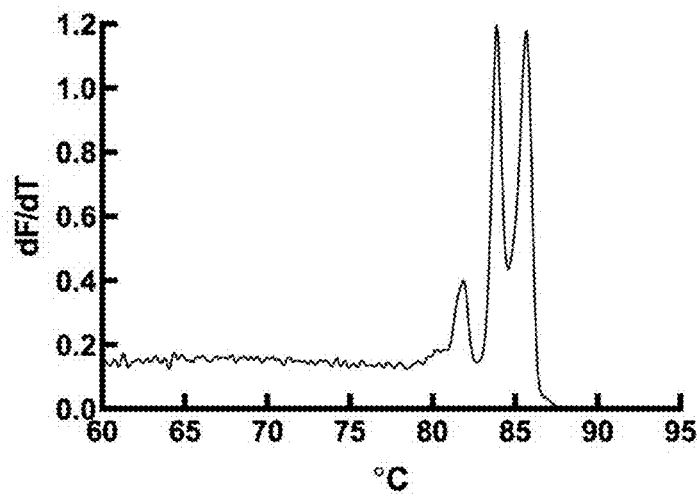
FIG. 36 shows an HRM curve for the ITS region of *Enterobacter agglomerans*.
Figure 37:
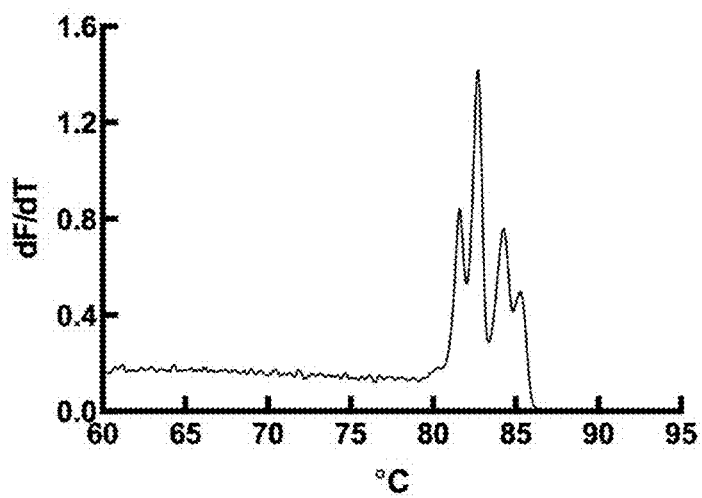
FIG. 37 shows an HRM curve for the ITS region of *Enterobacter cloacae*.
Figure 38:
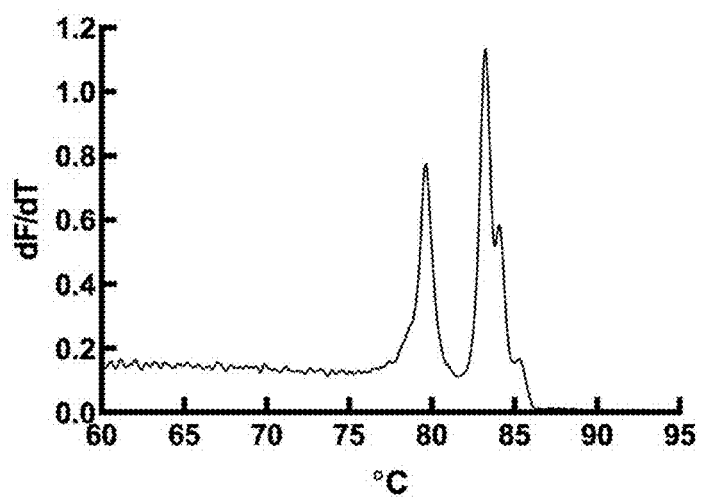
FIG. 38 shows an HRM curve for the ITS region of *Enterococcus casseliflavus*.
Figure 39:
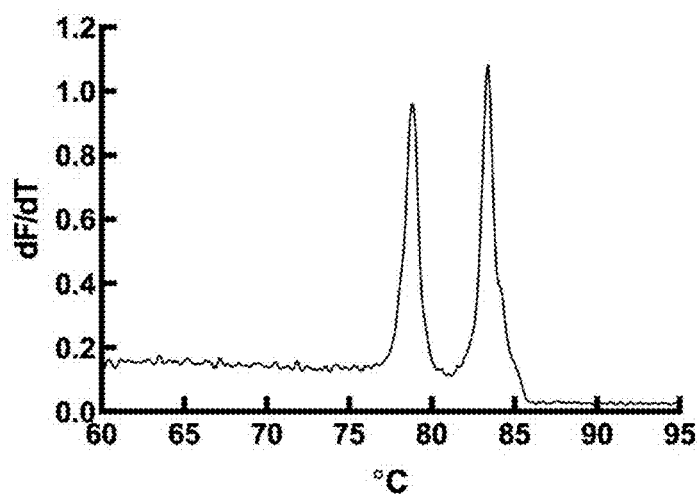
FIG. 39 shows an HRM curve for the ITS region of *Enterococcus durans*.
Figure 40:
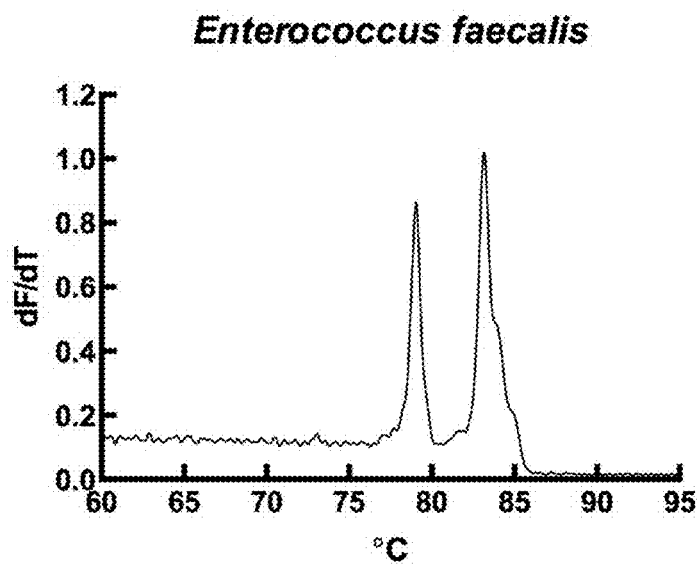
FIG. 40 shows an HRM curve for the ITS region of *Enterococcus faecalis*.
Figure 41:
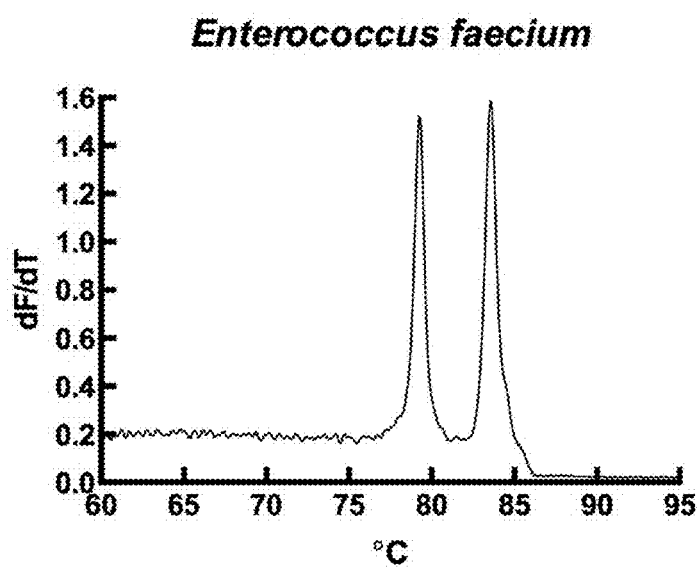
FIG. 41 shows an HRM curve for the ITS region of *Enterococcus faecium*.
Figure 42:
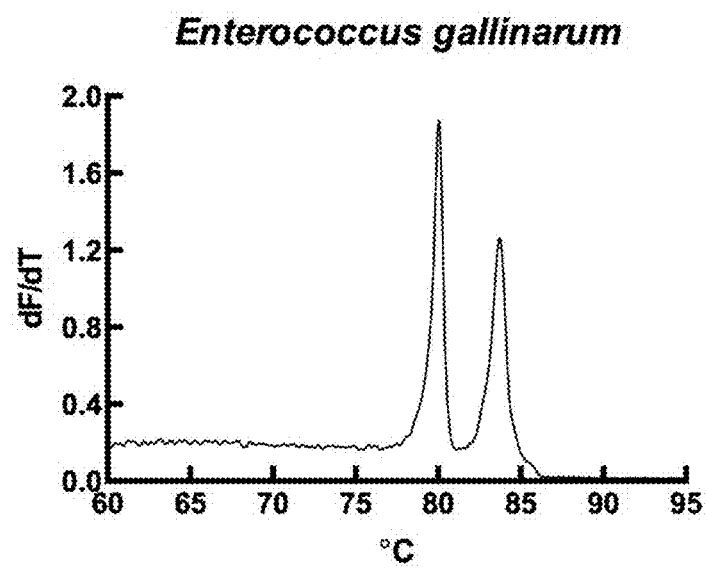
FIG. 42 shows an HRM curve for the ITS region of *Enterococcus gallinarum*.
Figure 43:
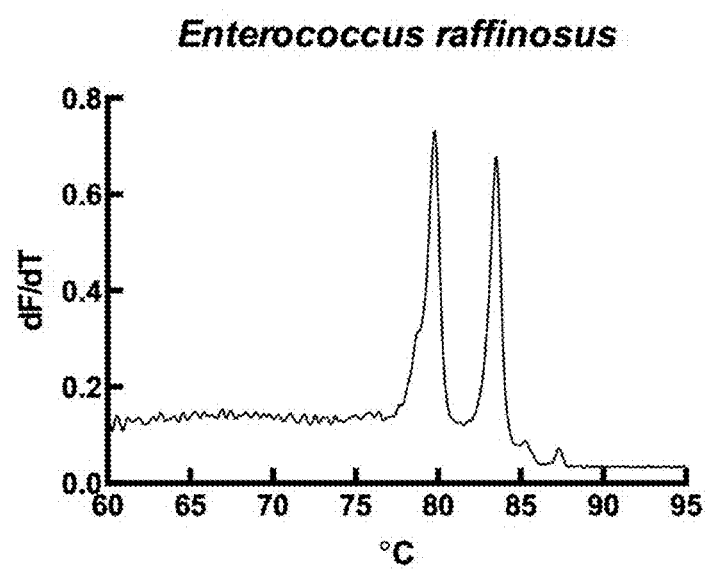
FIG. 43 shows an HRM curve for the ITS region of *Enterococcus raffinosus*.
Figure 44:
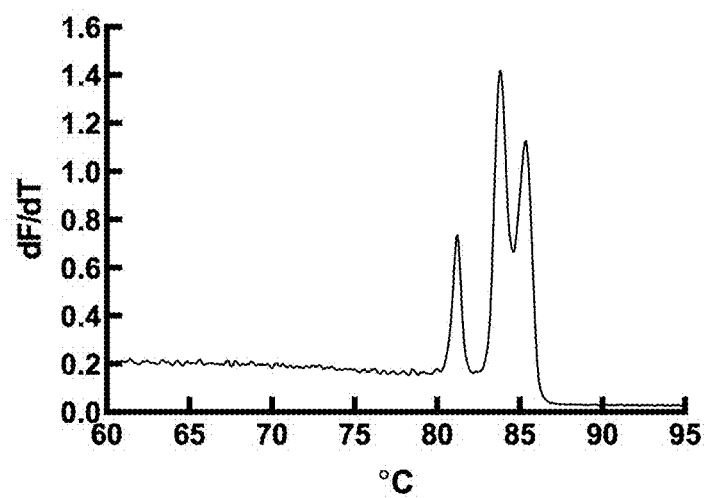
FIG. 44 shows an HRM curve for the ITS region of *Escherichia coli*.
Figure 45:
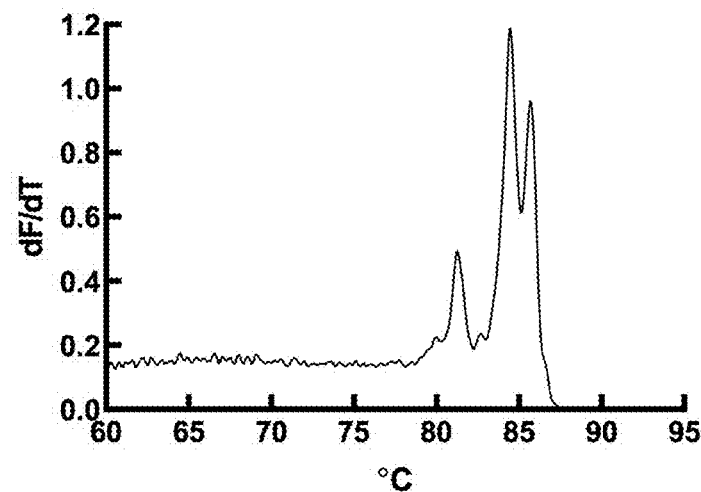
FIG. 45 shows an HRM curve for the ITS region of *Escherichia vulneris*.
Figure 46:
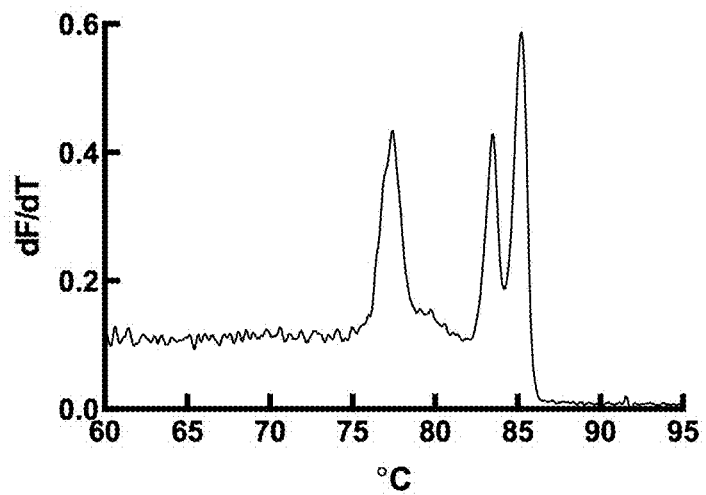
FIG. 46 shows an HRM curve for the ITS region of *Francisella philomiragia*.
Figure 47:
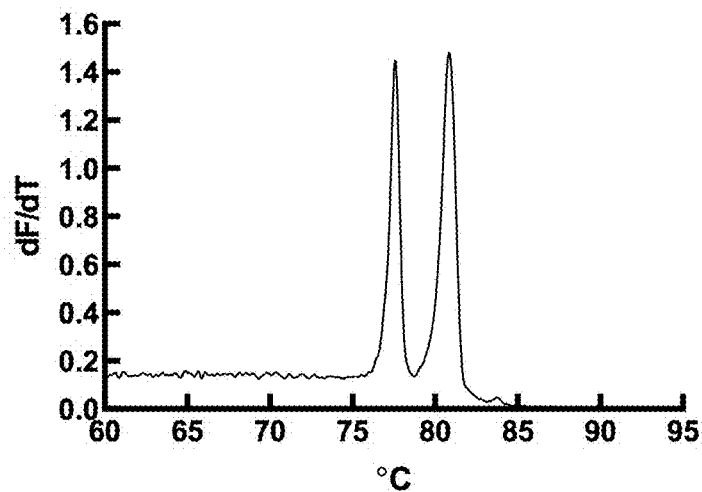
FIG. 47 shows an HRM curve for the ITS region of *Francisella tularensis*.
Figure 48:
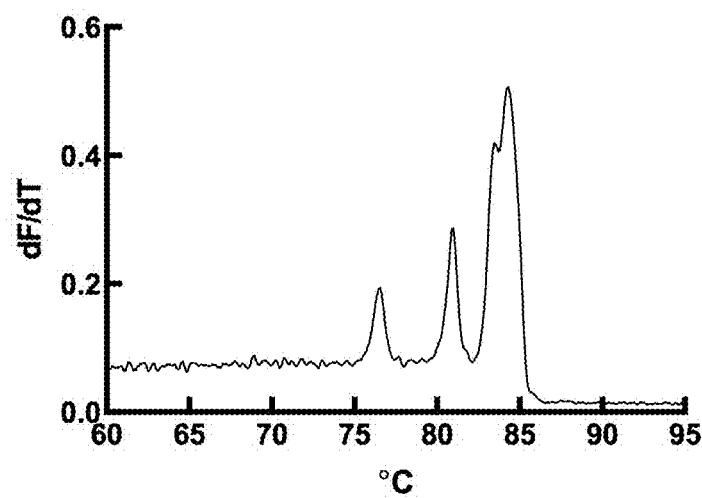
FIG. 48 shows an HRM curve for the ITS region of *Fusobacterium nucleatum*.
Figure 49:
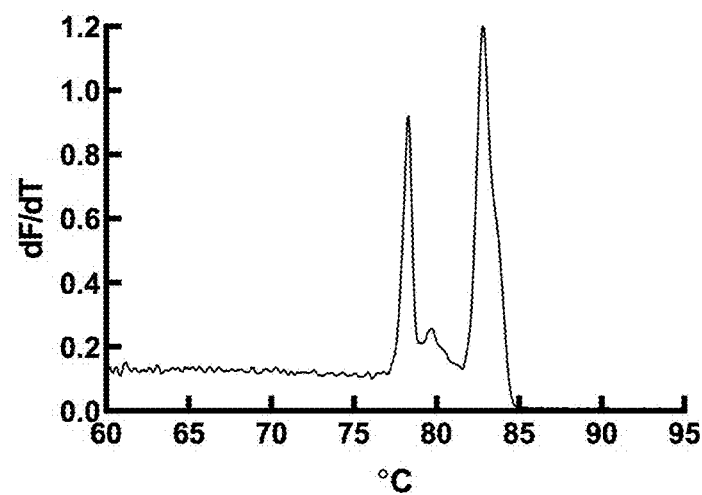
FIG. 49 shows an HRM curve for the ITS region of *Haemophilus influenzae*.
Figure 50:
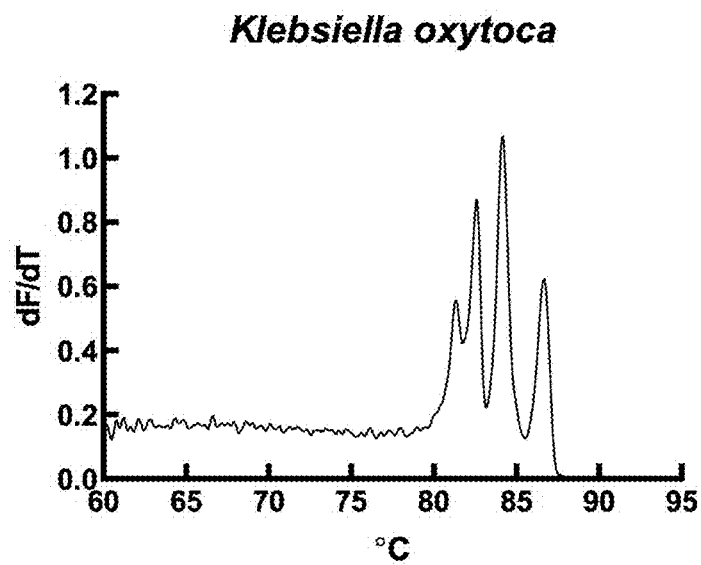
FIG. 50 shows an HRM curve for the ITS region of *Klebsiella ox
Figure 51:
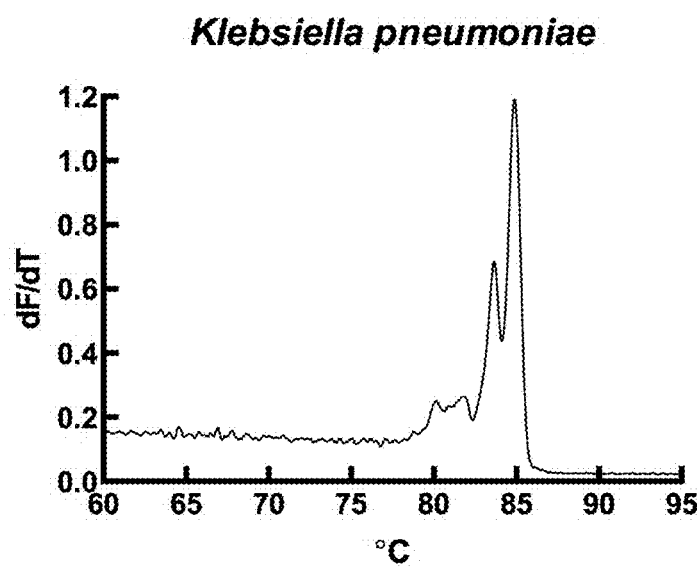
Figure 52:
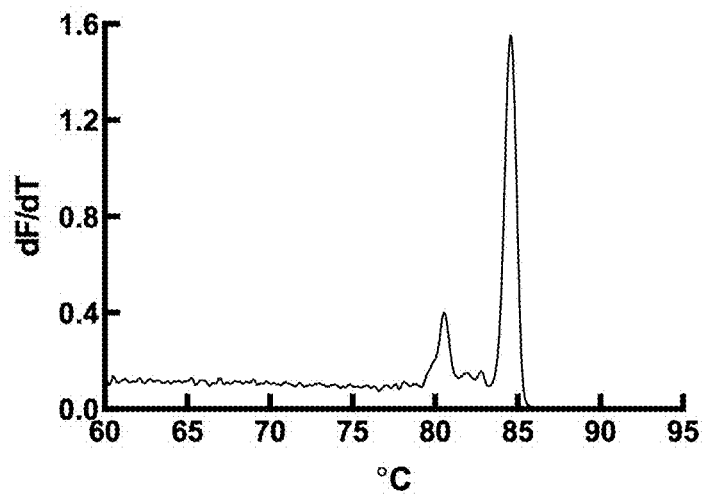
Figure 53:
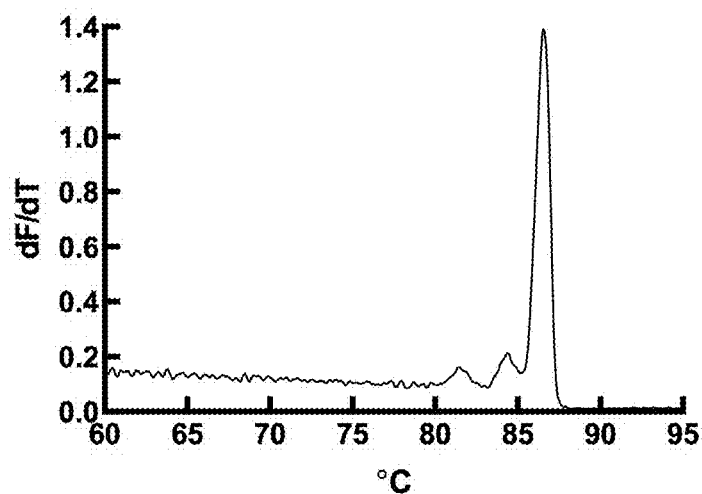
Figure 54:
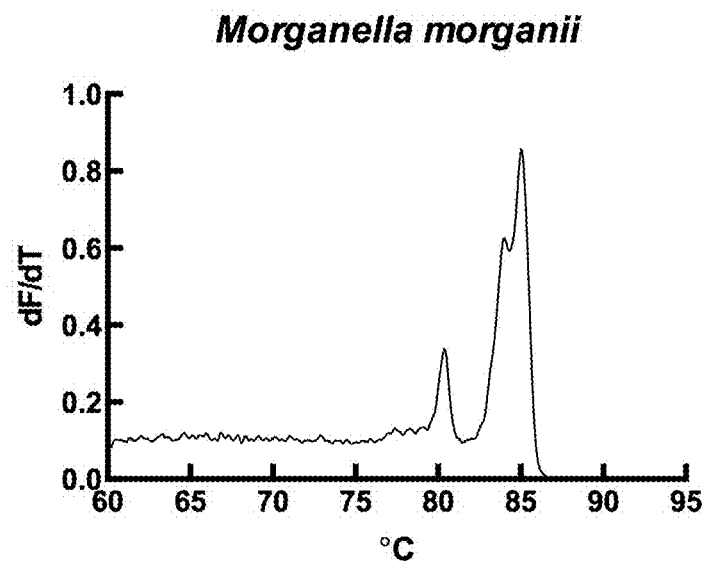
Figure 55:
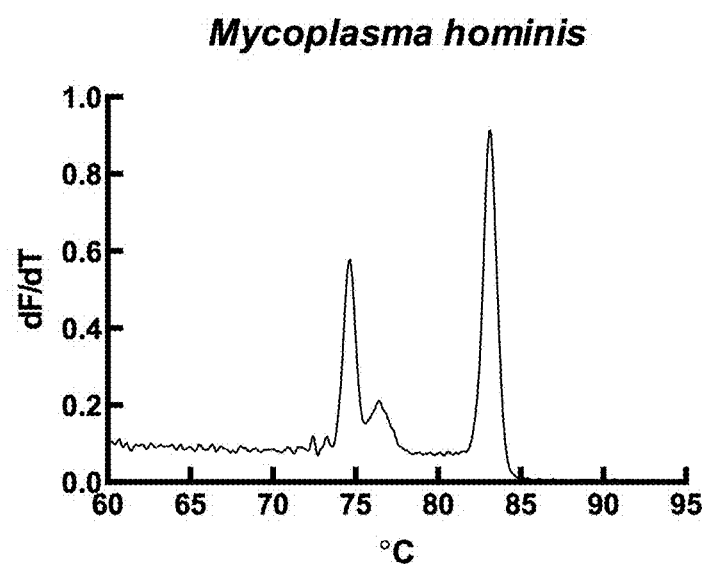
Figure 56:
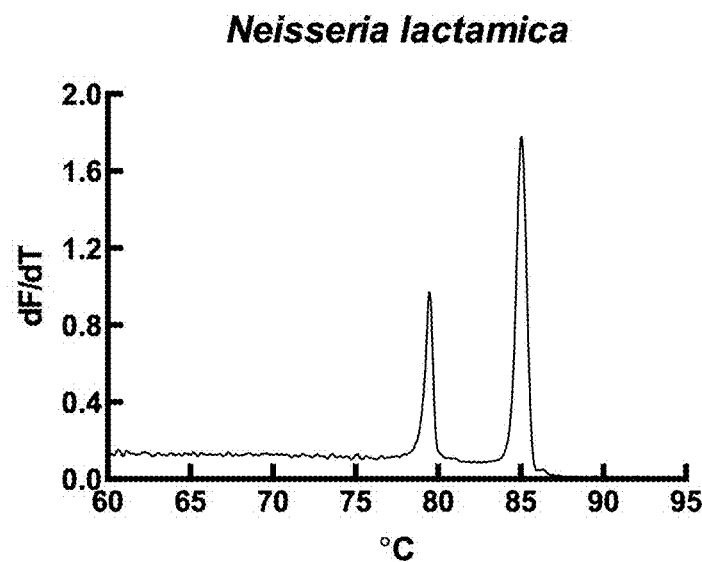
Figure 57:
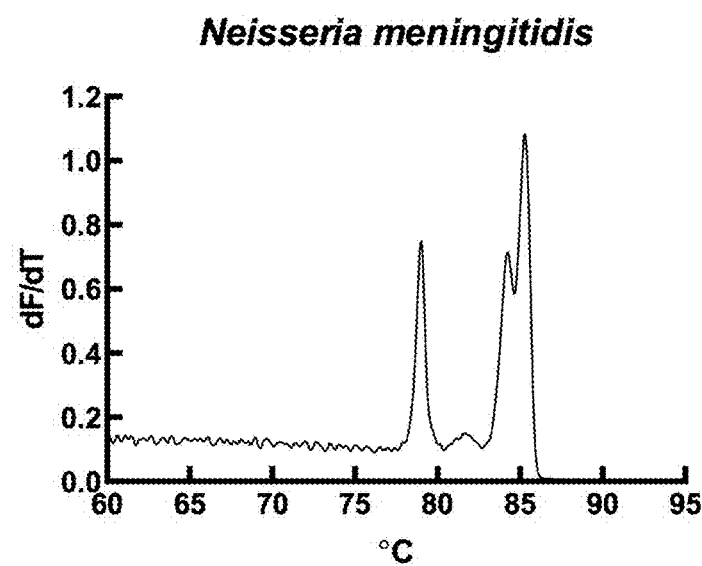
Figure 58:
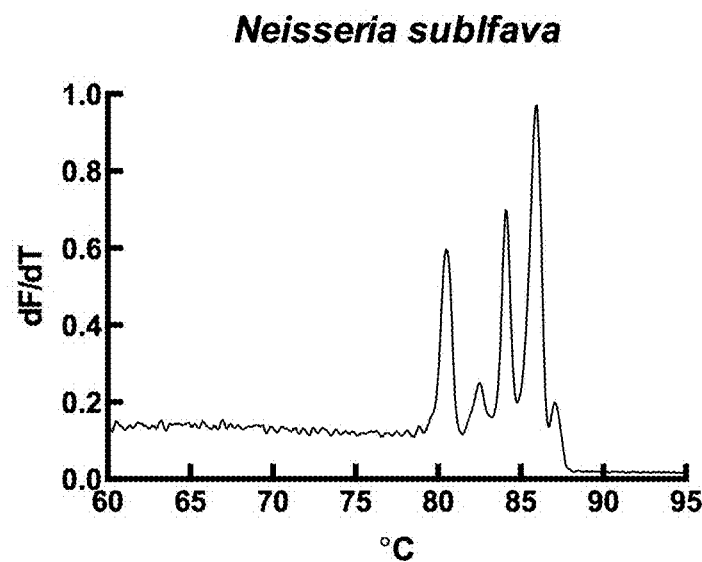
Figure 59:
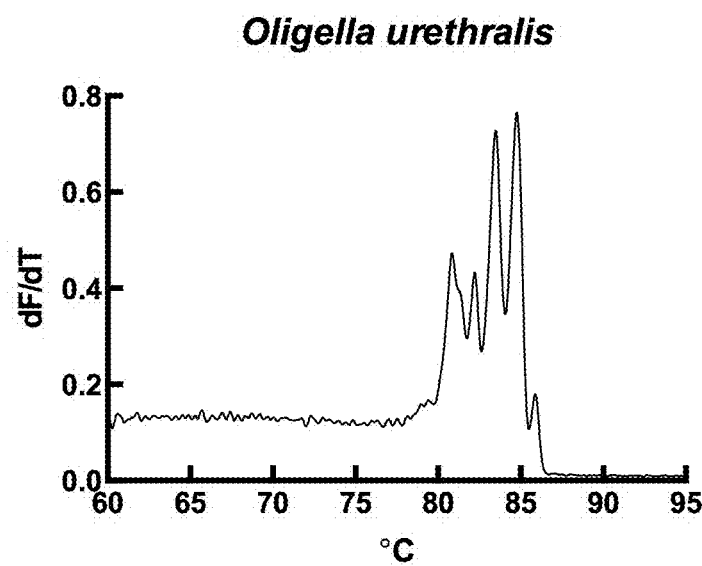
Figure 60:
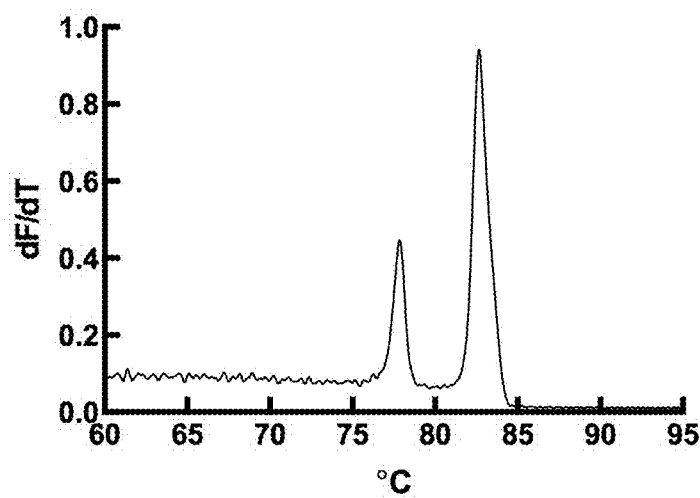
Figure 61:
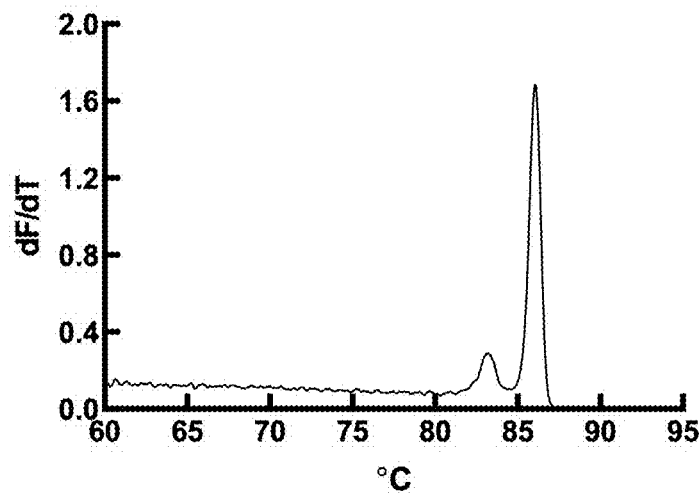
Figure 62:
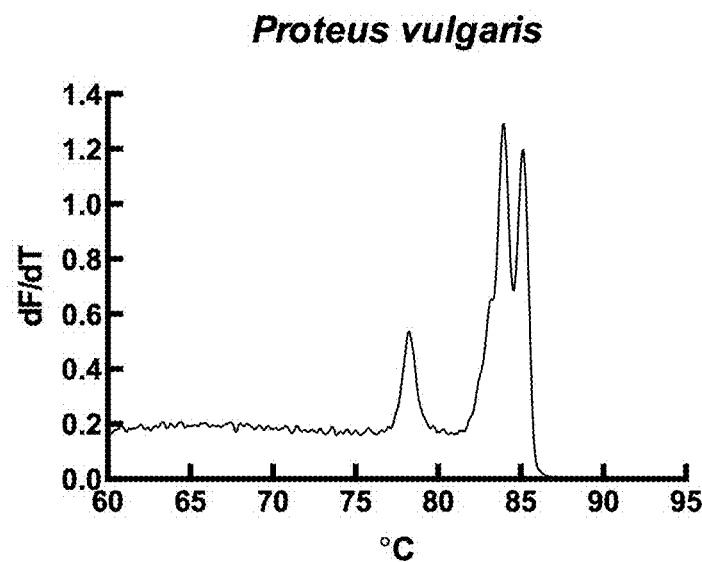
Figure 63:
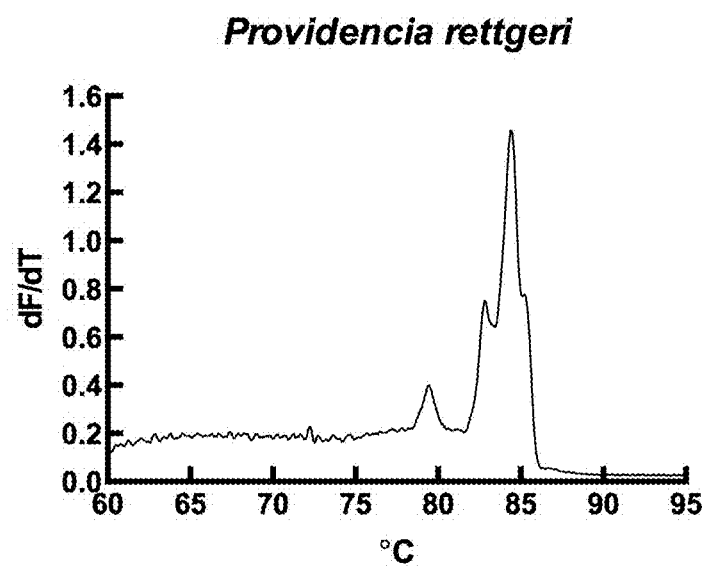
Figure 64:
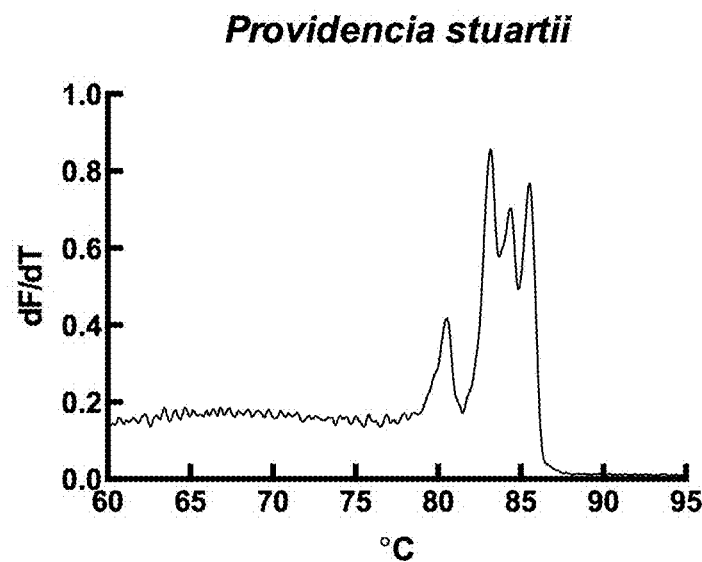
Figure 65:
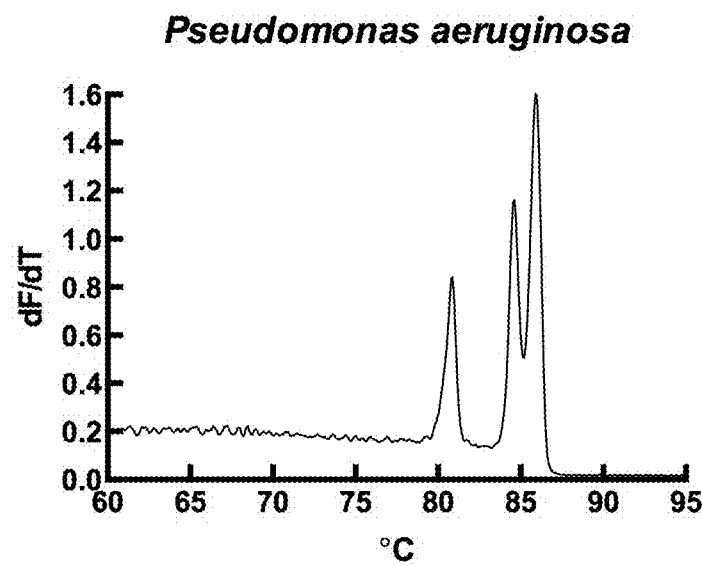
Figure 66:
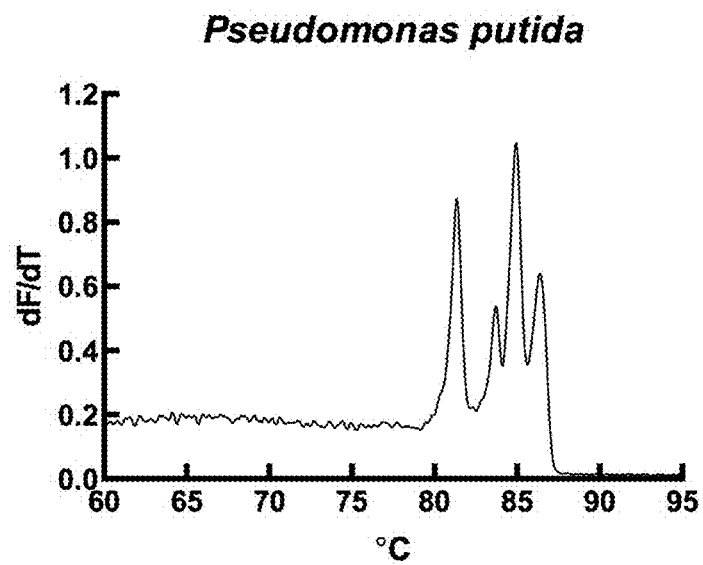
Figure 67:
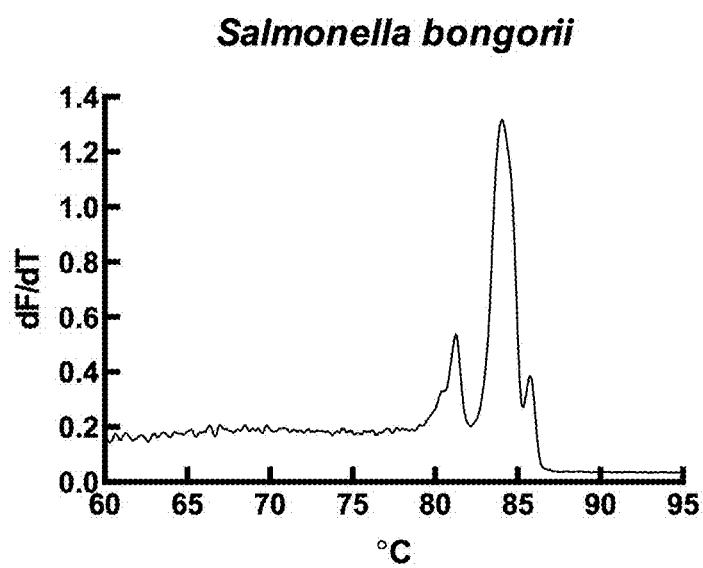
Figure 68:
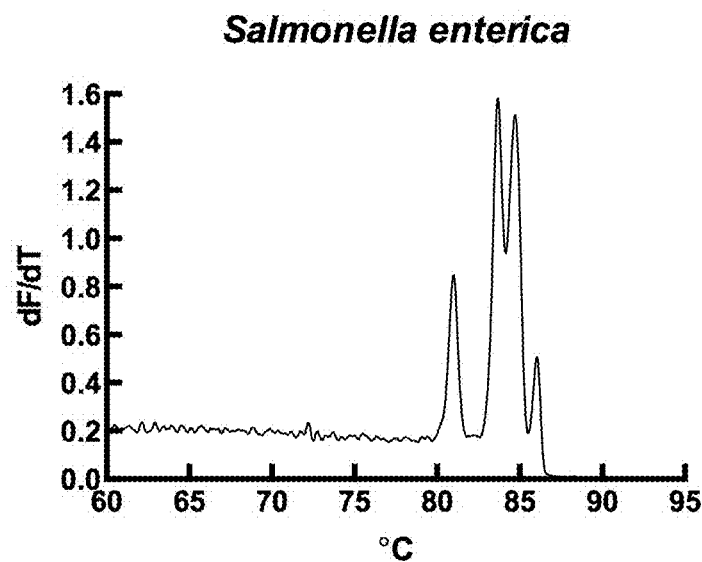
Figure 69:
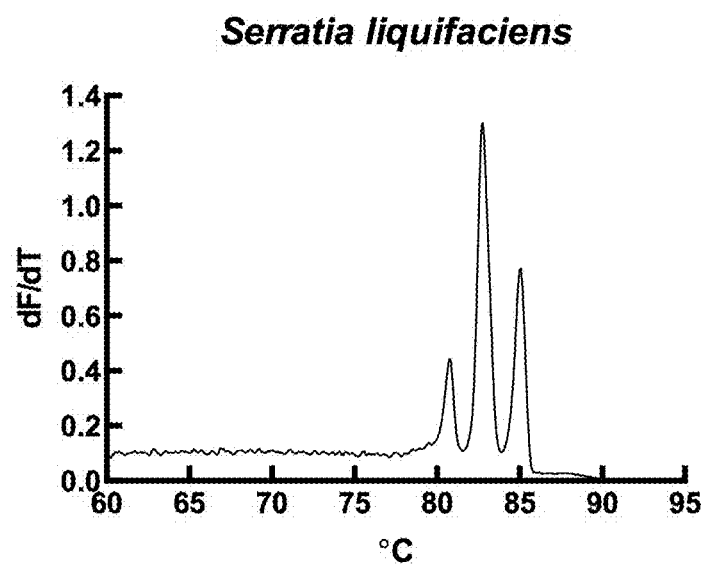
Figure 70:
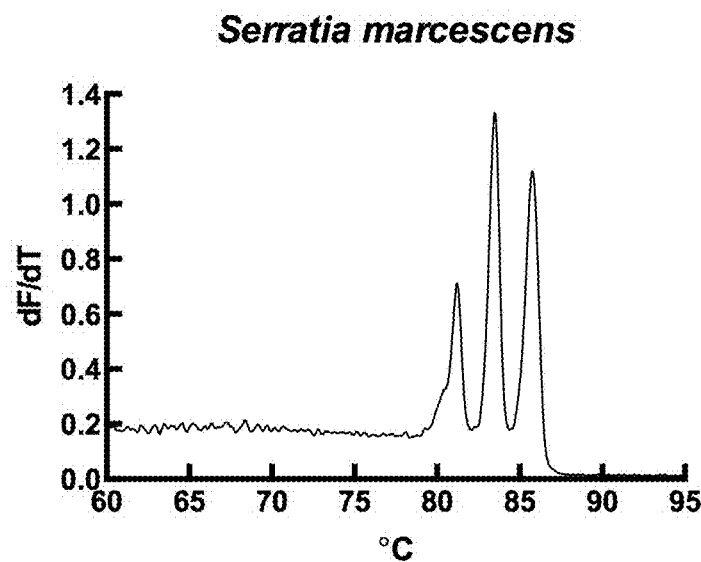
Figure 71:
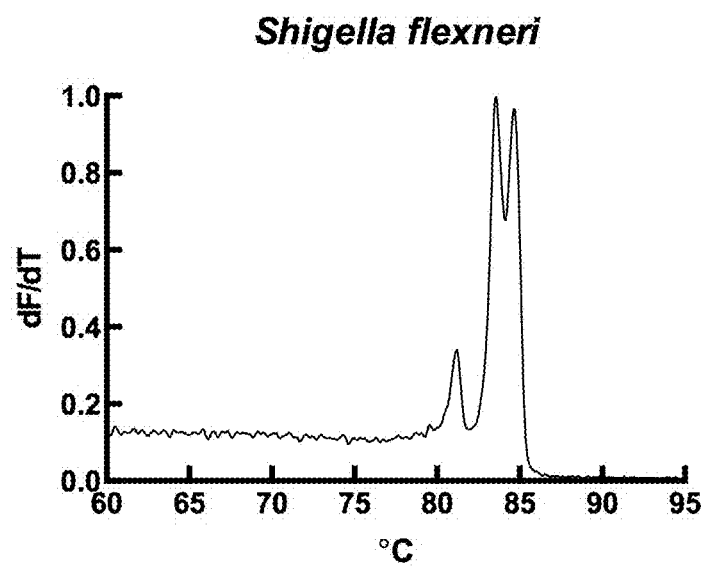
Figure 72:
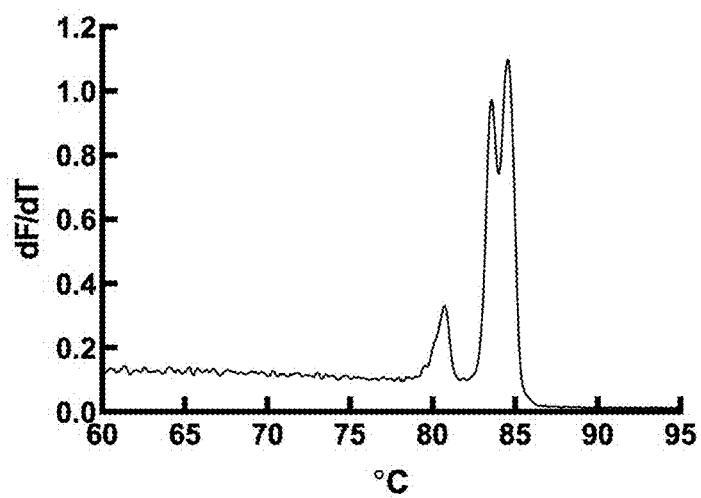
Figure 73:
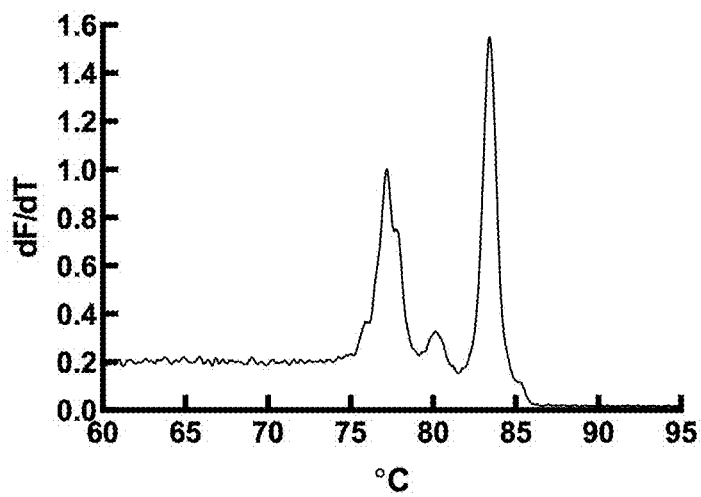
Figure 74:
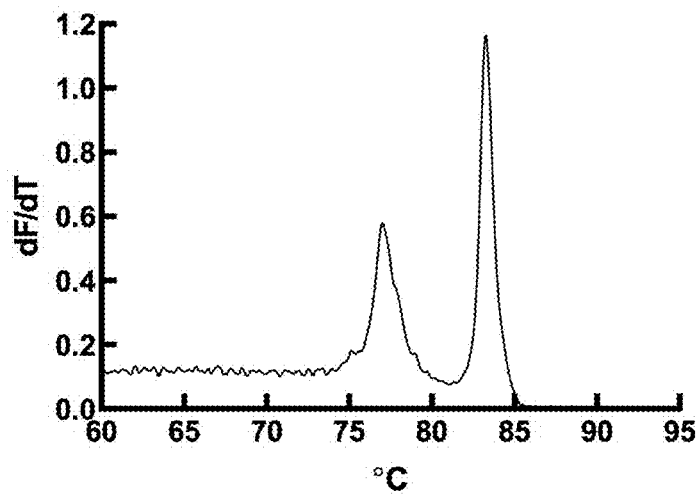
Figure 75:
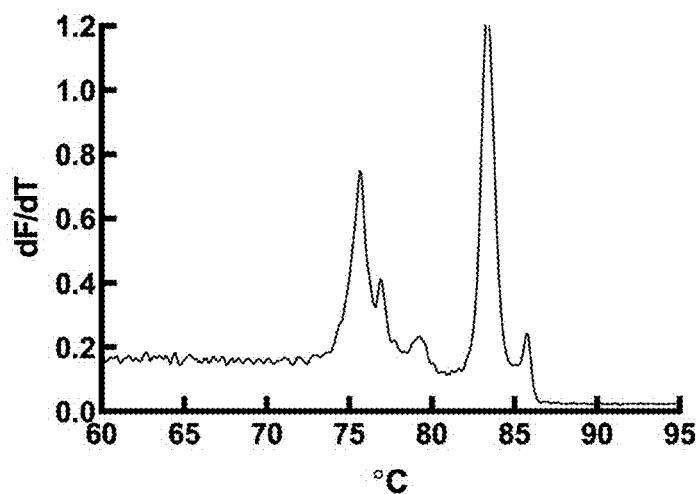
Figure 76:
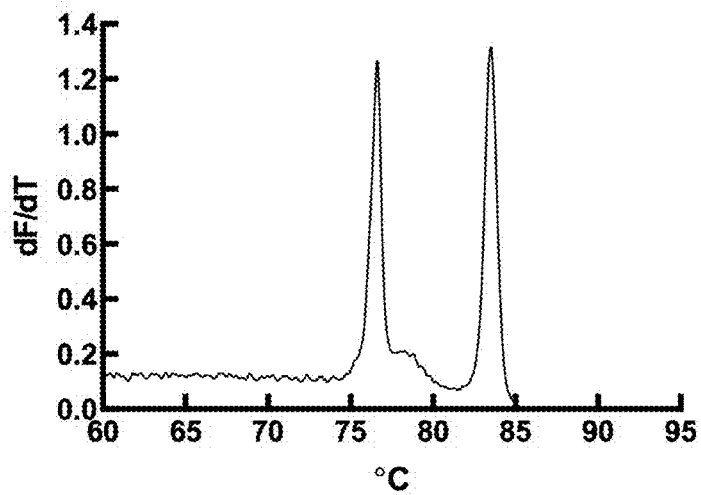
Figure 77:
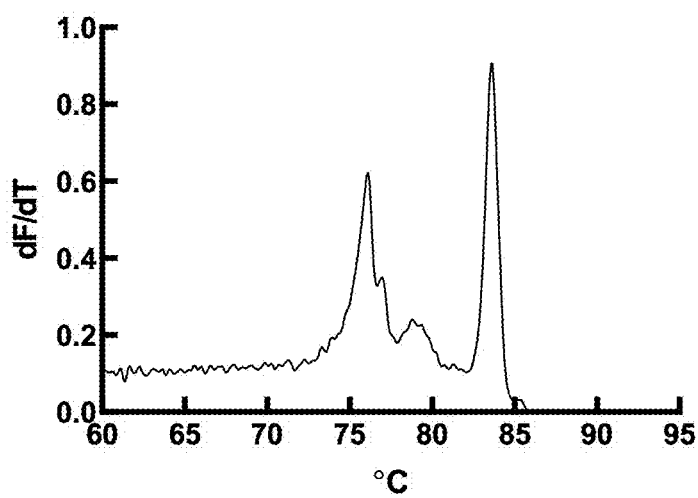
Figure 78:
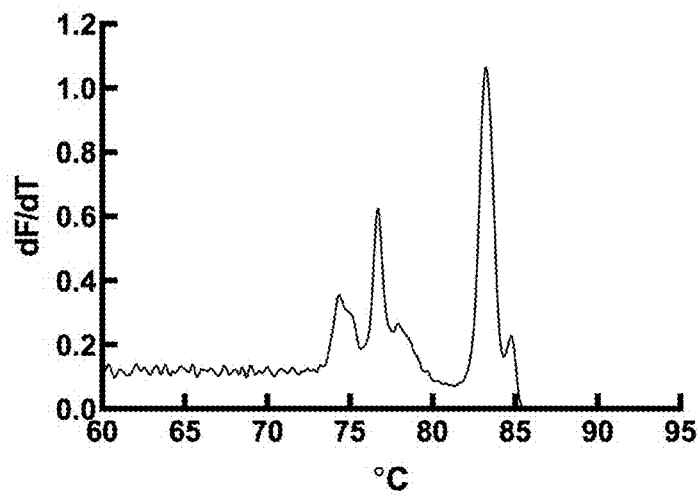
Figure 79:
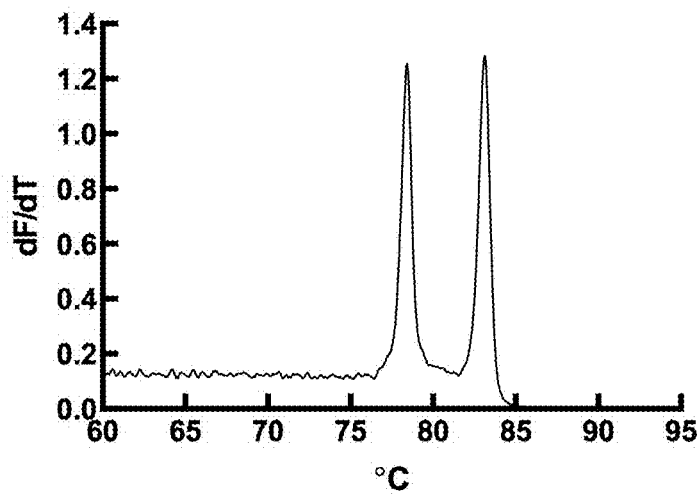
Figure 80:
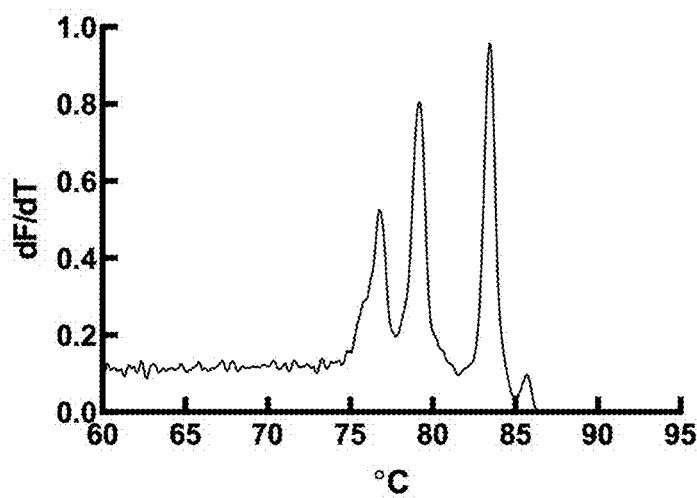
Figure 81:
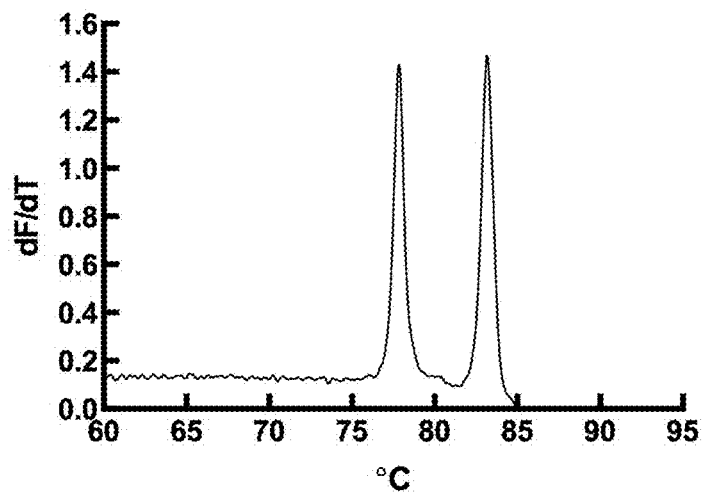
Figure 82:
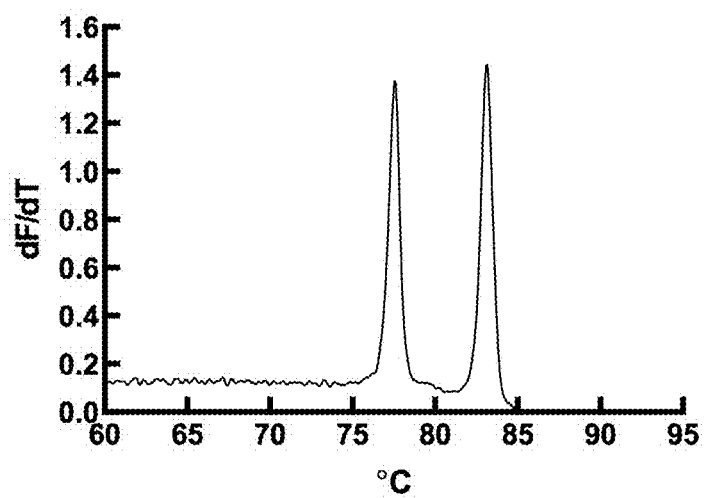
Figure 83:
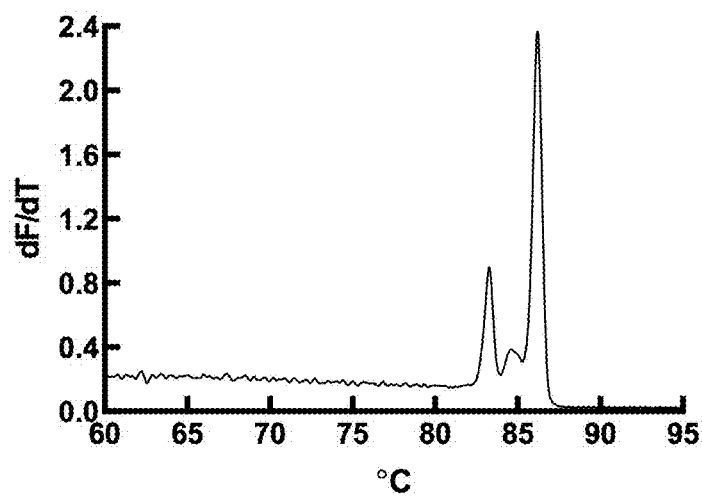
Figure 84:
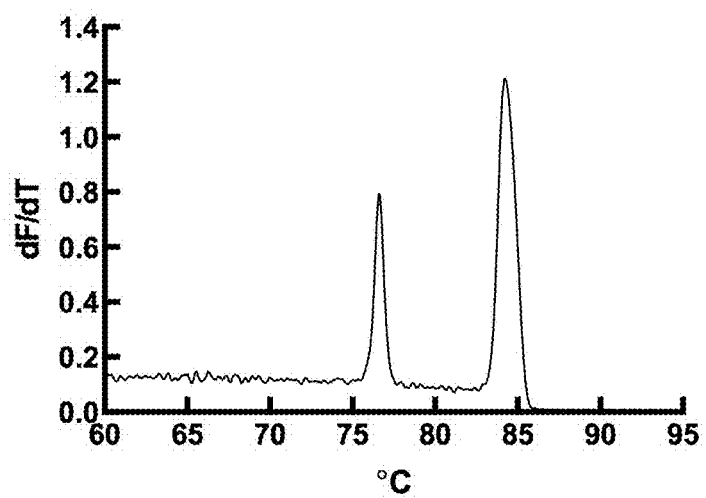
Figure 85:
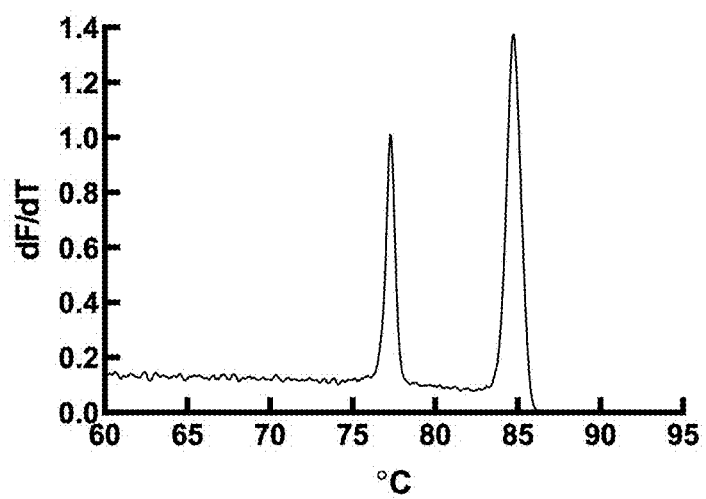
Figure 86:
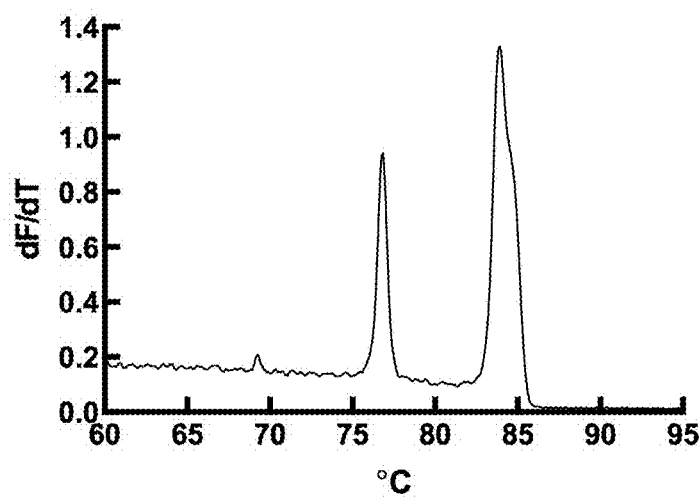
Figure 87:
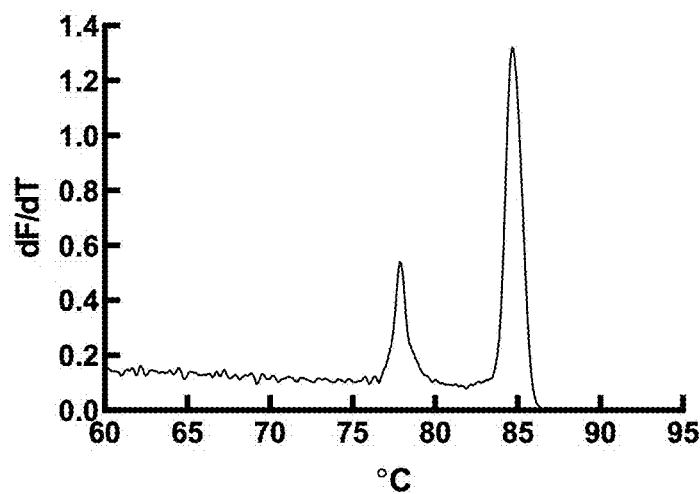
Figure 88:
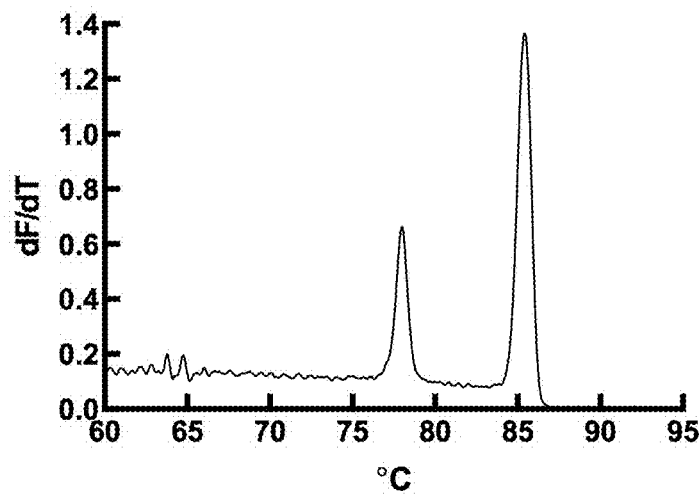
Figure 89:
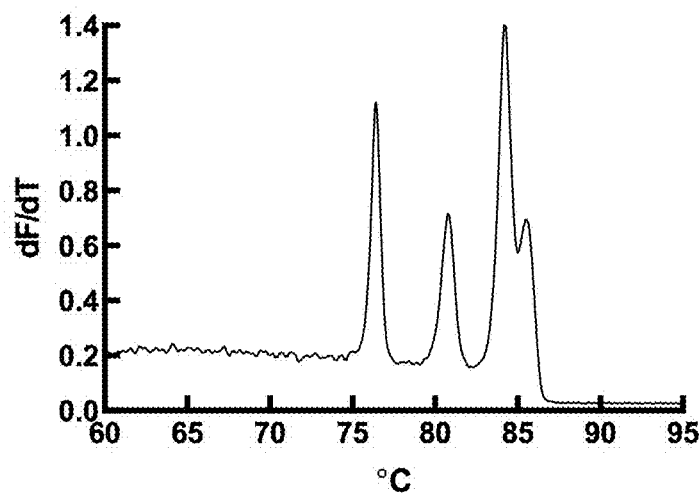
FIG. 89 shows an HRM curve for the ITS region of *Streptococcus pyogenes*.
Figure 90:
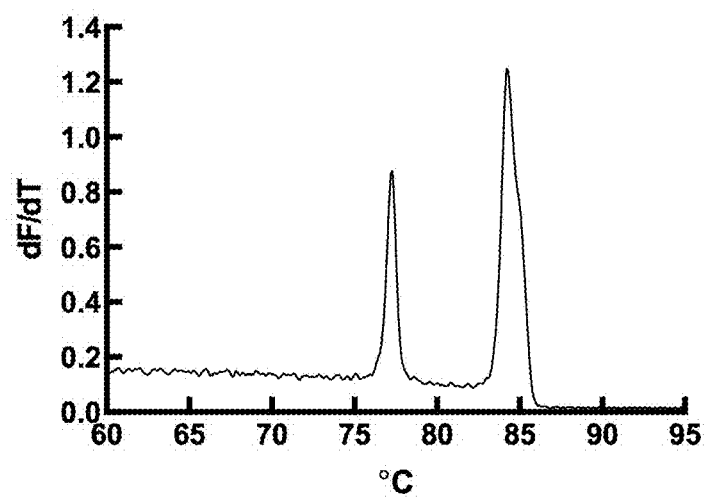
FIG. 90 shows an HRM curve for the ITS region of *Vibrio vulnificus*.
Figure 91:
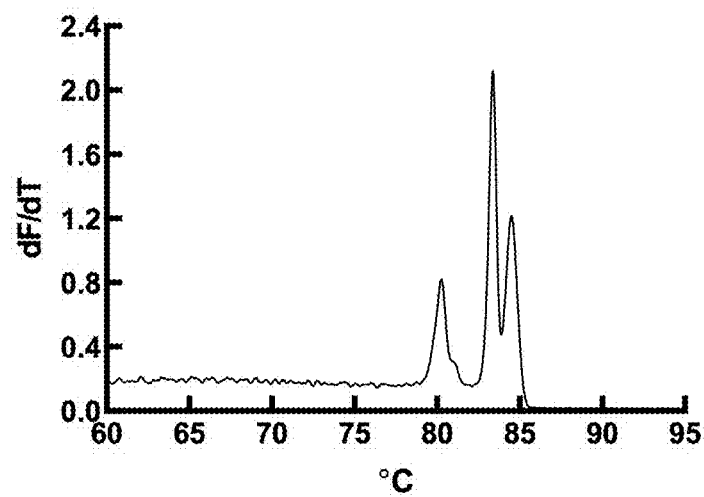
FIG. 91 shows an HRM curve for the ITS region of *Yersinia pestis*.
Figure 92:
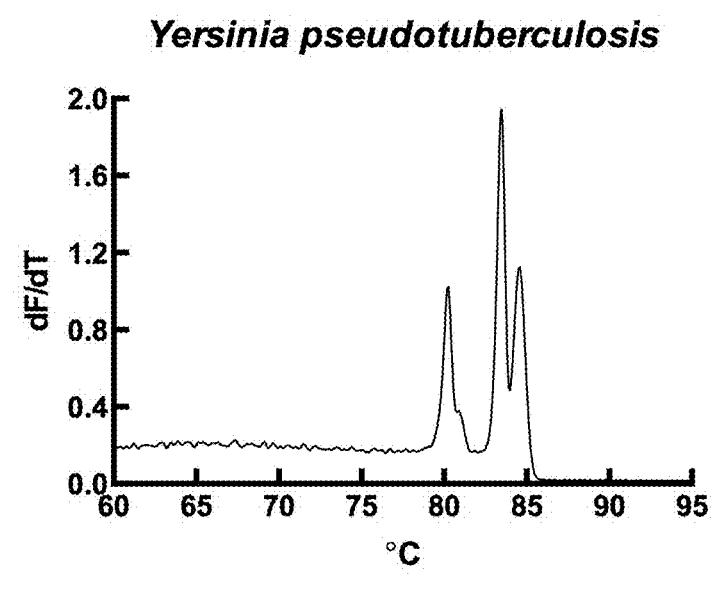

Examples of the categories may include pathogenic versus non-pathogenic bacteria, gram positive versus gram negative, bacterial genus classification, or bacterial morphology. For pathogenic bacteria, the HRM curves may be further subdivided by type of bacterial disease (e.g., respiratory infection, urinary tract infection, skin infection, food-borne illnesses, sepsis, pneumonia, meningitis, vaginosis, etc.). Exemplary HRM reference curves for known bacterial species are shown in FIGS. 4-92. In certain embodiments, the database comprises one or more HRM reference curves selected from FIGS. 4-92, or all of the HRM reference curves shown in FIGS. 4-92.

Once a bacterial species is identified, an HRM curve for the ITS DNA, produced as described herein, may be stored in a database comprising reference HRM curves for known bacterial species. Identifying a species of bacteria in a test sample may comprise using a database of reference HRM curves for genomic ITS DNA from known bacterial species, and finding a reference HRM curve from the database that matches the HRM curve for the bacteria from the test sample.

In some embodiments, identification of a bacterial species by HRM analysis is automated by use of a machine learning algorithm. The machine learning algorithm may comprise a supervised learning algorithm. Examples of supervised learning algorithms include Average One-Dependence Estimators (AODE), Artificial neural network (e.g., Backpropagation), Bayesian statistics (e.g., Naive Bayes classifier, Bayesian network, Bayesian knowledge base), Case-based reasoning, Decision trees, Inductive logic programming, Gaussian process regression, Group method of data handling (GMDH), Learning Automata, Learning Vector Quantization, Minimum message length (decision trees, decision graphs, etc.), Lazy learning, Instance-based learning Nearest Neighbor Algorithm, Analogical modeling, Probably approximately correct learning (PAC) learning, Ripple down rules, a knowledge acquisition methodology, Symbolic machine learning algorithms, Subsymbolic machine learning algorithms, Support vector machines, Random Forests, Ensembles of classifiers, Bootstrap aggregating (bagging), and Boosting. Supervised learning may comprise ordinal classification such as regression analysis and Information fuzzy networks (IFN). Alternatively, supervised learning methods may comprise statistical classification, such as AODE, Linear classifiers (e.g., Fisher's linear discriminant, Logistic regression, Naive Bayes classifier, Perceptron, and Support vector machine), quadratic classifiers, k-nearest neighbor, Boosting, Decision trees (e.g., C4.5, Random forests), Bayesian networks, and Hidden Markov models.

The machine learning algorithms may also comprise an unsupervised learning algorithm. Examples of unsupervised learning algorithms may include artificial neural network, Data clustering, Expectation-maximization algorithm, Self-organizing map, Radial basis function network, Vector Quantization, Generative topographic map, Information bottleneck method, and IBSEAD. Unsupervised learning may also comprise association rule learning algorithms such as Apriori algorithm, Eclat algorithm and FP-growth algorithm. Hierarchical clustering, such as Single-linkage clustering and Conceptual clustering, may also be used. Alternatively, unsupervised learning may comprise partitional clustering such as K-means algorithm and Fuzzy clustering.

In some instances, the machine learning algorithms comprise a reinforcement learning algorithm. Examples of reinforcement learning algorithms include, but are not limited to, temporal difference learning, Q-learning and Learning Automata. Alternatively, the machine learning algorithm may comprise Data Pre-processing.

In another aspect, the invention includes a high resolution melt (FIRM) system for identifying bacteria. An HRM system comprises a) at least one set of primers capable of specifically hybridizing to and amplifying at least a portion of an internal transcribed spacer (ITS) region of bacterial DNA; b) an intercalating dye suitable for performing HRM analysis; c) a PCR chamber, wherein the PCR chamber is configured to perform PCR amplification of the bacterial DNA with the primers; and d) an HRM chamber, wherein the HRM chamber is configured to perform HRM analysis of the amplified bacterial DNA. In certain embodiments, the PCR chamber and the HRM chamber are contained within a microfluidic device. In one embodiment, the microfluidic device is equipped to perform ddPCR.

The HRM system may further comprise a computer containing a processor, a storage component (i.e., memory), a display component, and other components typically present in general purpose computers. The storage component stores information accessible by the processor, including instructions that may be executed by the processor and data that may be retrieved, manipulated or stored by the processor.

The storage component includes instructions for identifying bacteria by HRM analysis. The computer processor is coupled to the storage component and configured to execute the instructions stored in the storage component in order to receive HRM data and analyze HRM data according to one or more algorithms. The display component displays information regarding the identification of bacteria.

In certain embodiments, the storage component may include instructions for identifying a bacterial species by HRM analysis using a machine learning algorithm, as described herein, for automated melt curve classification (see Example 1). The storage component may also include a database comprising a number of HRM reference curves for known bacterial species. Exemplary HRM reference curves for known bacterial species are shown in FIGS. 4-92. In certain embodiments, the database comprises one or more HRM reference curves selected from FIGS. 4-92, or all of the HRM reference curves shown in FIGS. 4-92.

The storage component may be of any type capable of storing information accessible by the processor, such as a hard-drive, memory card, ROM, RAM, DVD, CD-ROM, USB Flash drive, write-capable, and read-only memories. The processor may be any well-known processor, such as processors from Intel Corporation. Alternatively, the processor may be a dedicated controller such as an ASIC.

The instructions may be any set of instructions to be executed directly (such as machine code) or indirectly (such as scripts) by the processor. In that regard, the terms "instructions," "steps" and "programs" may be used interchangeably herein. The instructions may be stored in object code form for direct processing by the processor, or in any other computer language including scripts or collections of independent source code modules that are interpreted on demand or compiled in advance.

Data may be retrieved, stored or modified by the processor in accordance with the instructions. For instance, although the diagnostic system is not limited by any particular data structure, the data may be stored in computer registers, in a relational database as a table having a plurality of different fields and records, XML documents, or flat files. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information which is used by a function to calculate the relevant data.

In certain embodiments, the processor and storage component may comprise multiple processors and storage components that may or may not be stored within the same physical housing. For example, some of the instructions and data may be stored on removable CD-ROM and others within a read-only computer chip. Some or all of the instructions and data may be stored in a location physically remote from, yet still accessible by, the processor. Similarly, the processor may actually comprise a collection of processors which may or may not operate in parallel.

In one aspect, computer is a server communicating with one or more client computers. Each client computer may be configured similarly to the server, with a processor, storage component and instructions. Each client computer may be a personal computer, intended for use by a person, having all the internal components normally found in a personal computer such as a central processing unit (CPU), display (for example, a monitor displaying information processed by the processor), CD-ROM, hard-drive, user input device (for example, a mouse, keyboard, touch-screen or microphone), speakers, modem and/or network interface device (telephone, cable or otherwise) and all of the components used for connecting these elements to one another and permitting them to communicate (directly or indirectly) with one another. Moreover, computers in accordance with the systems and methods described herein may comprise any device capable of processing instructions and transmitting data to and from humans and other computers including network computers lacking local storage capability.

Although the client computers may comprise a full-sized personal computer, many aspects of the system and method are particularly advantageous when used in connection with mobile devices capable of wirelessly exchanging data with a server over a network such as the Internet. For example, client computer may be a wireless-enabled PDA such as a Blackberry phone, Apple iPhone, Android phone, or other Internet-capable cellular phone. In such regard, the user may input information using a small keyboard, a keypad, a touch screen, or any other means of user input. The computer may have an antenna for receiving a wireless signal.

The server and client computers are capable of direct and indirect communication, such as over a network. Although one or only a few computers may be used, it should be appreciated that a typical system can include a large number of connected computers, with each different computer being at a different node of the network. The network, and intervening nodes, may comprise various combinations of devices and communication protocols including the Internet, World Wide Web, intranets, virtual private networks, wide area networks, local networks, cell phone networks, private networks using communication protocols proprietary to one or more companies, Ethernet, WiFi and HTTP. Such communication may be facilitated by any device capable of transmitting data to and from other computers, such as modems (e.g., dial-up or cable), networks and wireless interfaces. The server may be a web server.

Although certain advantages are obtained when information is transmitted or received as noted above, other aspects of the system and method are not limited to any particular manner of transmission of information. For example, in some aspects, information may be sent via a medium such as a disk, tape, flash drive, DVD, or CD-ROM. In other aspects, the information may be transmitted in a non-electronic format and manually entered into the system. Yet further, although some functions are indicated as taking place on a server and others on a client, various aspects of the system and method may be implemented by a single computer having a single processor.

3. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Microbial Typing by Machine Learned DNA Melt Signatures

Molecular approaches based on broad-range nucleic acid amplification of microbial-specific genetic targets are well suited for differential diagnosis of acute febrile illness. However, downstream amplicon analysis technologies (e.g. microarray, mass spectrometry, and sequencing) for microbial identification vary in information content, complexity, speed and cost, thereby limiting their practicality for routine use. High Resolution Melt (HRM), where an amplicon's sequence variants are interrogated by a process of heat denaturation in the presence of an intercalating dye, takes place as a single-step, closed-tube process performed directly on generic PCR platforms (Wittwer et al. (2003) Clinical Chemistry 49:853-860). Although not as information rich as sequencing, the simplicity, speed, cost, and accessibility of HRM suggest that microbiological analysis protocols that incorporate HRM for first-pass screening or diagnosis hold great promise for clinical adoption. Due to these advantages, our goal is to develop strategies for using HRM to accomplish reliable sequence fingerprinting for eubacterial species identification.

In HRM, the monitoring of amplicon's heat denaturation generates a sigmoidal melt curve, and the peak of its first derivative dictates the melting temperature (Tm), which is primarily determined by the sequence % GC content and length. Early HRM studies used short amplicons (<300 bp) and found that small (0.2° C.) shifts in Tm between samples generated reliable variant discrimination (Tong et al. (2012) J. Clin. Microbiol. 50:3418-3421). However, short amplicons tend to generate Tms within a narrow temperature ranges (~4° C. based on our prior work (Fraley et al. (2013) Nucleic Acids Res. 41:e175)) of the full melt spectrum, i.e., 60-95° C. If we need 0.2° C. to identify differences, a dynamic Tm range of 4° C. could only distinguish up to 20 variants. This represents a major challenge if HRM is to be expanded for large-scale fingerprinting of potentially hundreds of sequences. To overcome this limitation, we and others have designed HRM assays using multiple separate amplification reactions and primer sets to interrogate short hypervariable sequence stretches within the 16S rRNA gene (Fraley et al., supra; Athamanolap et al. (2014) PloS one 9, e109094; Hardick et al. (2012) J. Clin. Microbiol. 50:2428-2432; Jeng et al. (2012) J. Clin. Microbiol. 50:1122-1124; Masek et al. (2014) J. Mol. Diagn. 16:261-266; Niimi et al. (2015) Scientific Reports 5:12543; Won et al. (2010) J. Clin.

Microbiol. 48:3410-3413; Yang et al. (2009) J. Clin. Microbiol. 47:2252-2255). Although this approach moderately improves the discriminatory power, multiplex profiling through multiple parallel reactions to ensure each generates a pure melt curve not only complicates assay format, but is impractical in samples with very dilute target analytes without nested amplification.

In addition to Tm based information, HRM also observes the exact melt curve shape as a function of the actual nucleic acid sequence and strand complementarity. Depending on the number of regions with different % GC content (melt domains), the melt curve can be multiphasic, which is beneficial in sequence fingerprinting (Lilliebridge et al. (2011) PloS One 6:e19749). We explored the use of a long amplicon (1000 bp) covering six hypervariable regions in the 16S genetic locus to harbor more melt domains and sequence diversity with the use of a single primer set (Fraley et al. (2016) Scientific Reports 6:19218). Although the long amplicons yielded more biphasic melt curves, the narrow Tm range still constrains the profiling breadth. The 16S also has limited sequence variability to enable species-level discrimination of organisms through HRM (only 65 to 83% of cases) (Janda et al. (2007) J. Clin. Microbiol. 45:2761-2764). Another contributor to curve shape is the formation of heteroduplexes when two strands from different amplicons with sufficient base complementarity anneal during cooling. Heteroduplex formation by artificially mixing reference DNA with unknown DNA in a 1:1 ratio followed by HRM has been exploited as a strategy for heterozygote and variant screening, and enhancing curve diversity (Palais et al. (2005) Anal. Biochem. 346:167-175). However, this multi-step approach adds to assay complexity. Herein, we explore the use of a bacterial internal transcribed spacer region (ITS) as an alternative target locus. We hypothesize that by strategically choosing this phylogenetically stable locus, yet with intragenomic sequence heterogeneity, highly complex melt curves can be generated to enable large-scale profiling with enhanced species-level specificity in a simple assay format (FIG. 1).

HRM sensitivity to subtle differences in experimental conditions such as inconsistencies in instrumental operation and pipetting often causes run-to-run variability in melt curves Tms and overall shape. The current HRM data analysis, performed with the accompanying instrument software or a commercially available one such as ScreenClust (Reja et al. (2010) Methods 50:S10-14), is not capable of compensating for these fluctuations and therefore diminish the HRM assay's discriminatory power. To address this issue, we have developed an adaptive Naïve Bayes algorithm, which has the capability to 1) enable automated melt curve classification with trained tolerance for variations in experimental conditions, 2) use a database of melt curves from reference bacterial organisms for subsequent curve-matching analysis of unknown samples, 3) discover unanticipated organism when no match is found in the melt curve database, and 4) provide statistical interpretation. These features will yield clinically relevant information through unbiased automated interrogation of our HRM assay results.

Results

Targeting ITS Generates High Complexity Melt Curves

The 16S-23S ribosomal DNA (rDNA) internal transcribed spacer region (ITS) of the ribosomal operon rrn was used as an alternative to traditional 16S rDNA ribotyping for phylogenetic classification. ITS is known to have substantially greater interspecies polymorphisms yet high intraspecies conservation (Gurtler et al. (1996) Microbiology 142 (Pt 1):3-16). It is approximately 60-1,500 bp in length with up to 15 copies per genome with intragenomic variations in terms of length and sequence. Since these features of ITS may affect melt curve conditions, we hypothesized that they make this region an ideal target for HRM analysis that will generate melt curves of complex shapes.

Figure 2A:
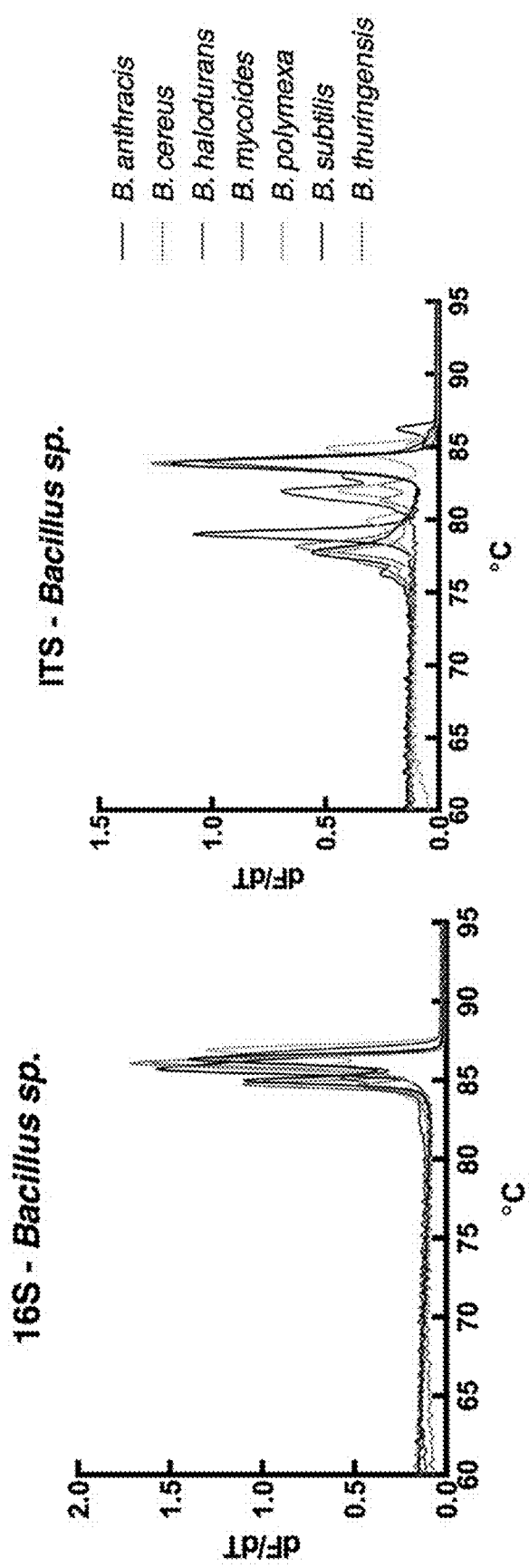
Figure 2B:
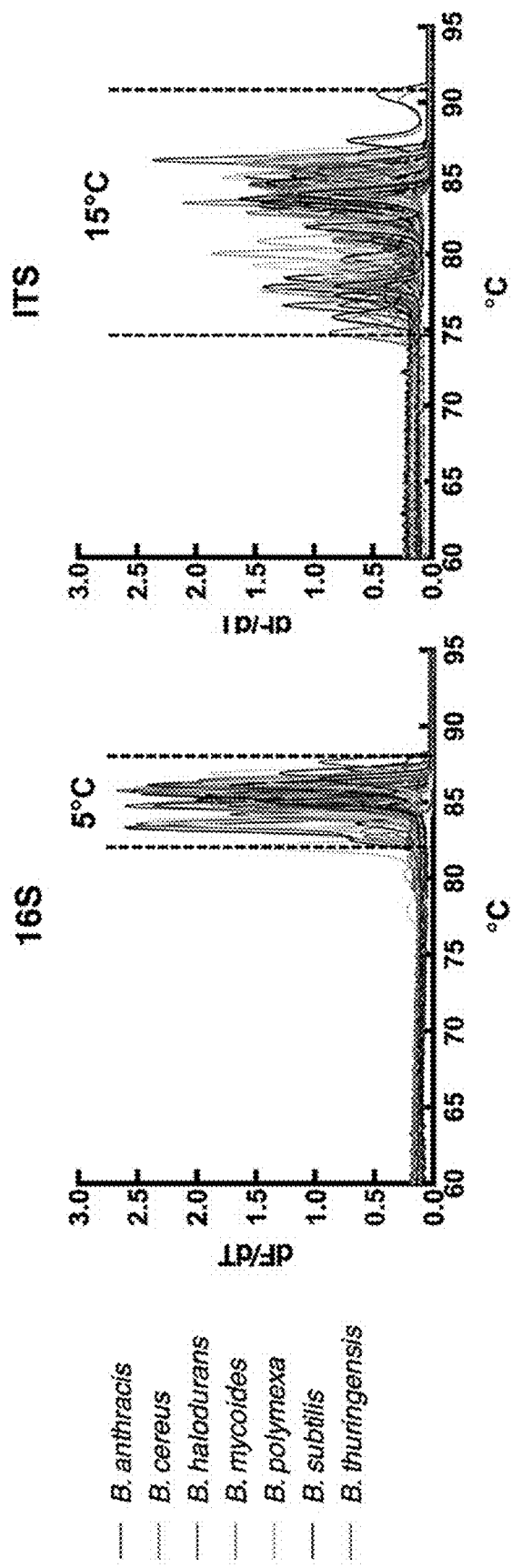
Figure 2C:
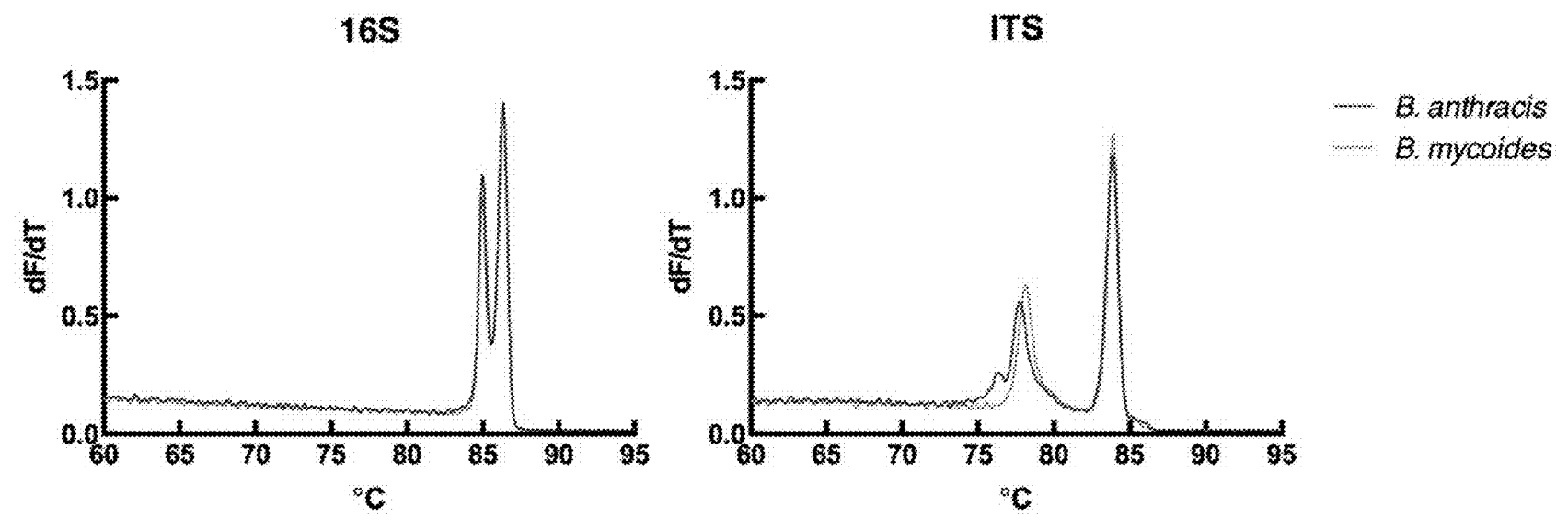
Figure 2D:
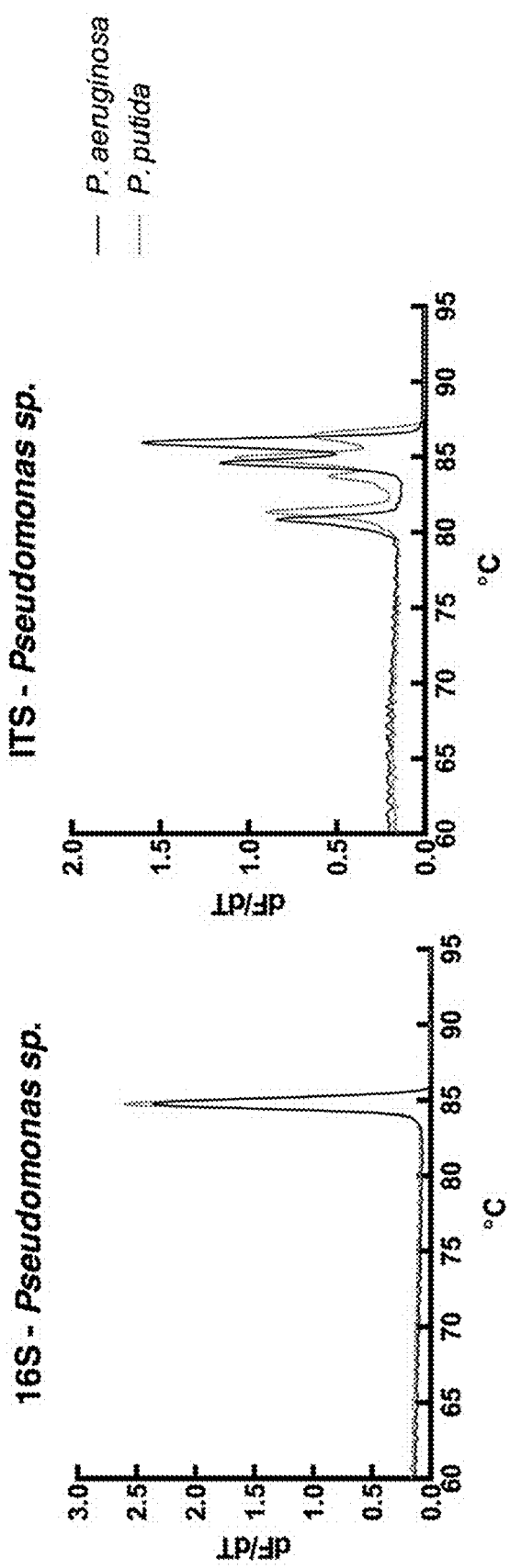
Figure 2E:
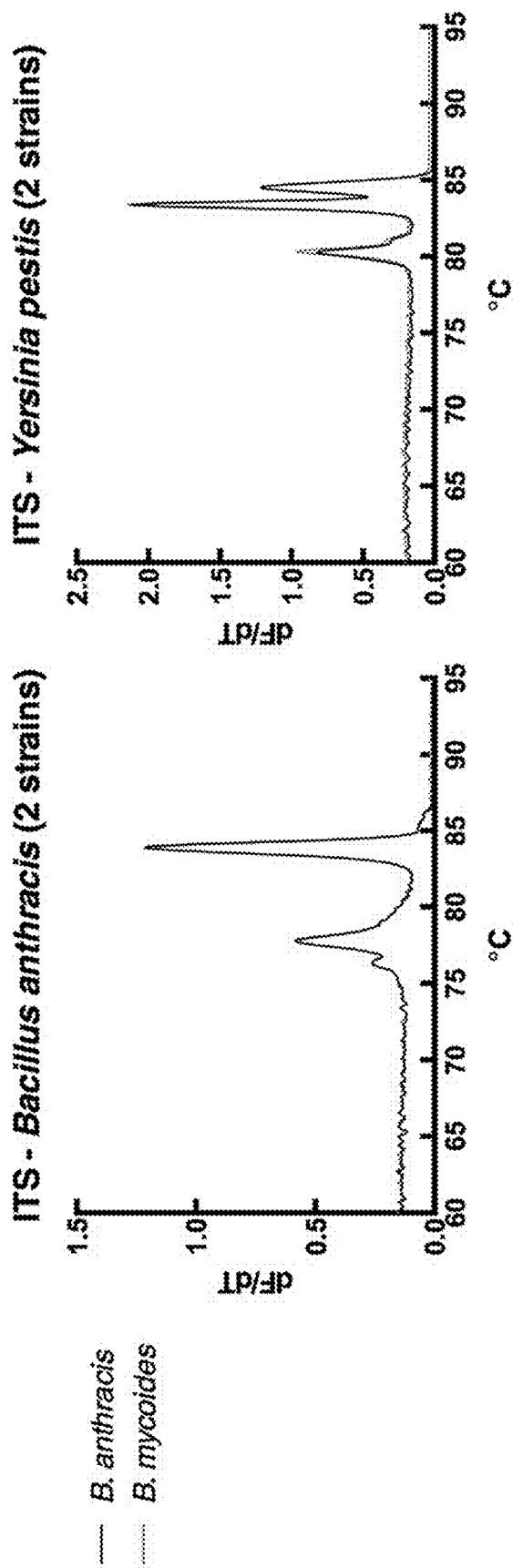
Figure 2F:
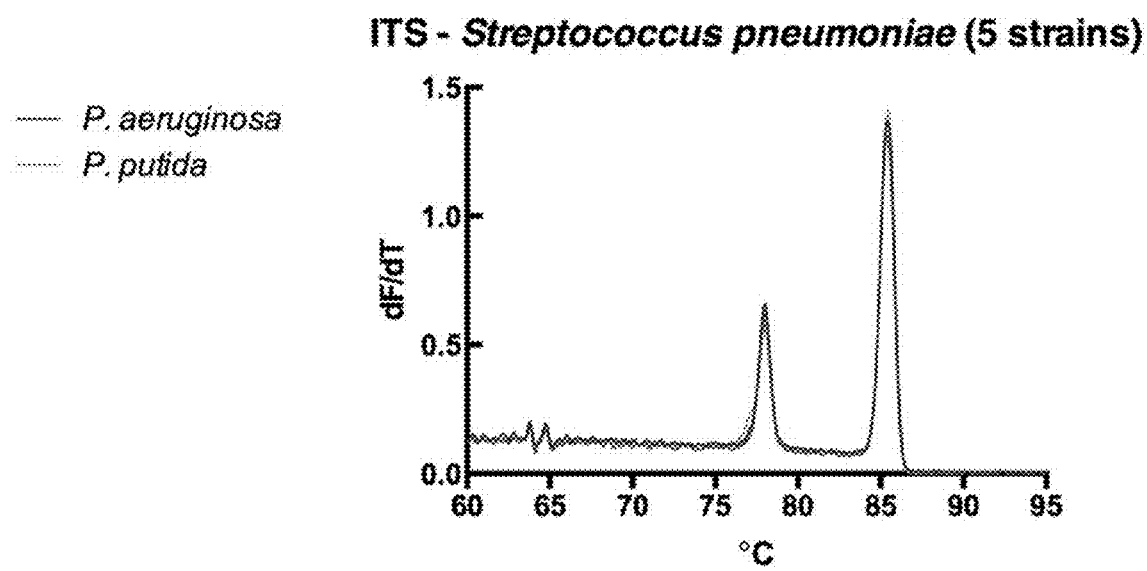

To evaluate this, we generated a library of both long 16S and ITS amplicons for 89 available and identified bacterial species (Table 3). These 89 species covered common pathogenic as well as commensal bacteria across multiple phylogenetic families and genera. Representative curves for each organism are available in FIGS. 4-92. The 89 species exhibit high diversity in curve shapes within a given genus (i.e. *Bacillus*) (FIG. 2A) as well as across all 89 species (FIG. 2B). Increased diversity of ITS curve shape as compared to 16S is clearly evident, with ITS curves showing multiple peaks, and a much wider Tm range (15° C. compared to 5° C. for 16S) (FIGS. 2A-2D). We also observed that close members of the same genus, indistinguishable by their 16S curves, are visually distinct based on ITS curves (FIG. 2C). Multiple strains of the same species included in our library generated identical melt curves, suggesting strain inclusivity for species-level identification (FIG. 2D). We also confirmed run-to-run and inter-operator reproducibility.

Heteroduplex Analysis

Figure 3B:
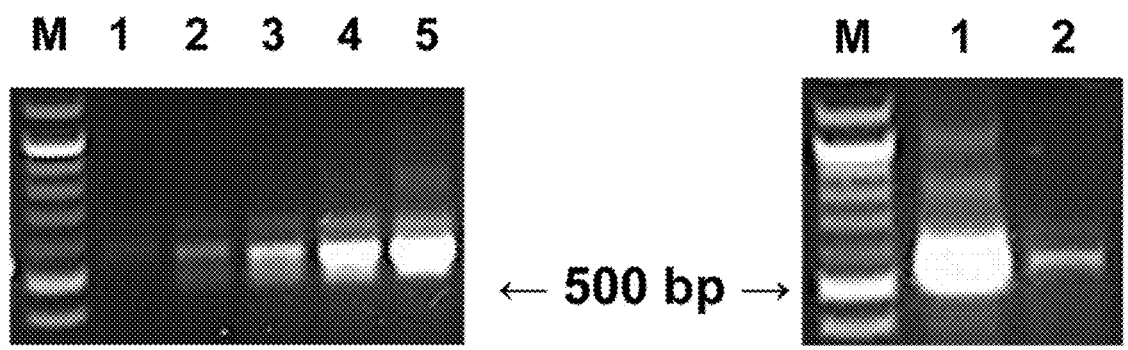
Figure 3C:
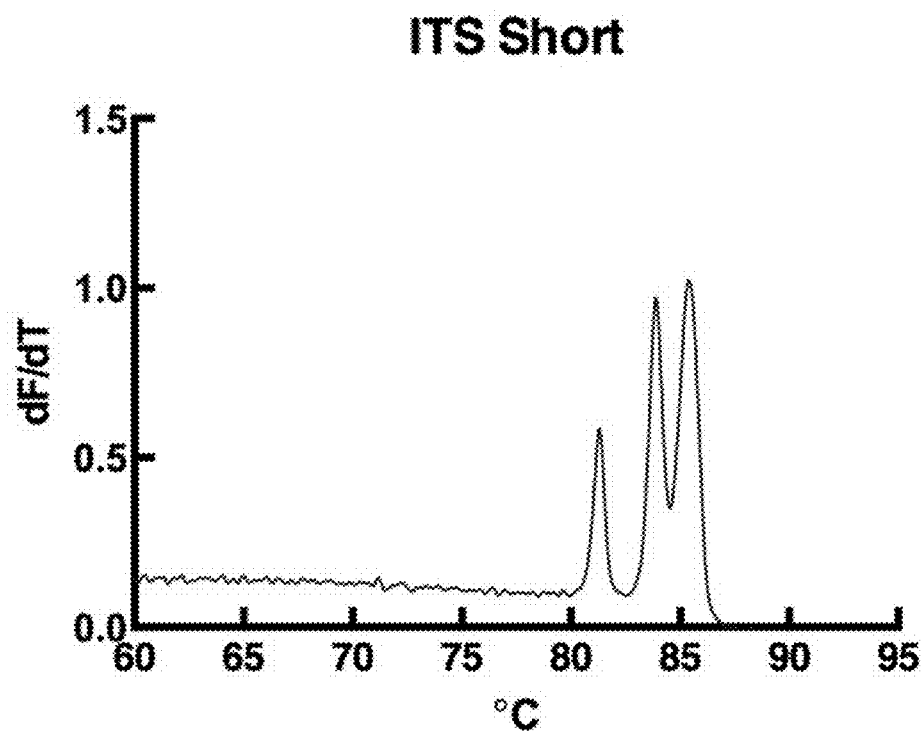

In order to elucidate the mechanism that produces the complex ITS melt curves, we first examined the entire genome of *E. coli* (strain ATCC 25922, GenBank Accession number CP009072), and found 7 ITS copies characterized by 6 copies containing the same shorter sequence (ITS short) and 1 copy containing a longer sequence (ITS long). Alignment of these two sequences using Clustal Omega (Sievers et al. (2014) Methods Mol. Biol. 1079:105-116) in silico revealed multiple regions of heterologous internal sequence (FIG. 3A). We then amplified the ITS region of *E. coli* ATCC 25922 with increasing cycle number. A slower migrating band observed on the gel electrophoresis beyond 25 cycles suggested increasing presence of heteroduplex structures (FIG. 3B). This was confirmed through subsequent treatment of ITS amplicons with mung bean nuclease, which cleaves unpaired DNA strands of heteroduplex products, resulting in loss of the larger band (FIG. 3C).

Figure 3D:
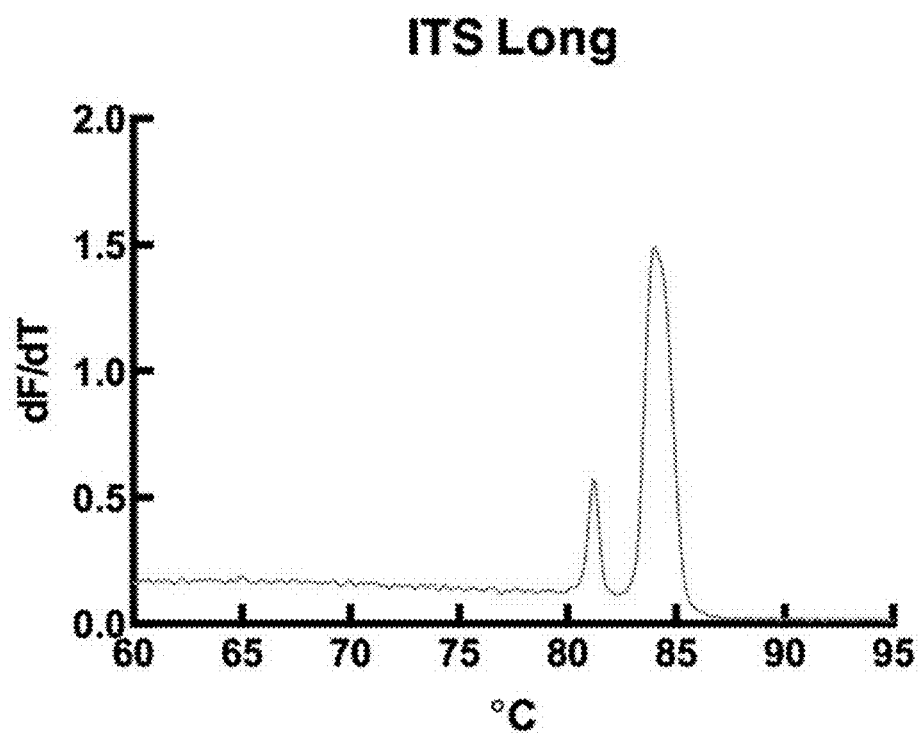
Figure 3E:
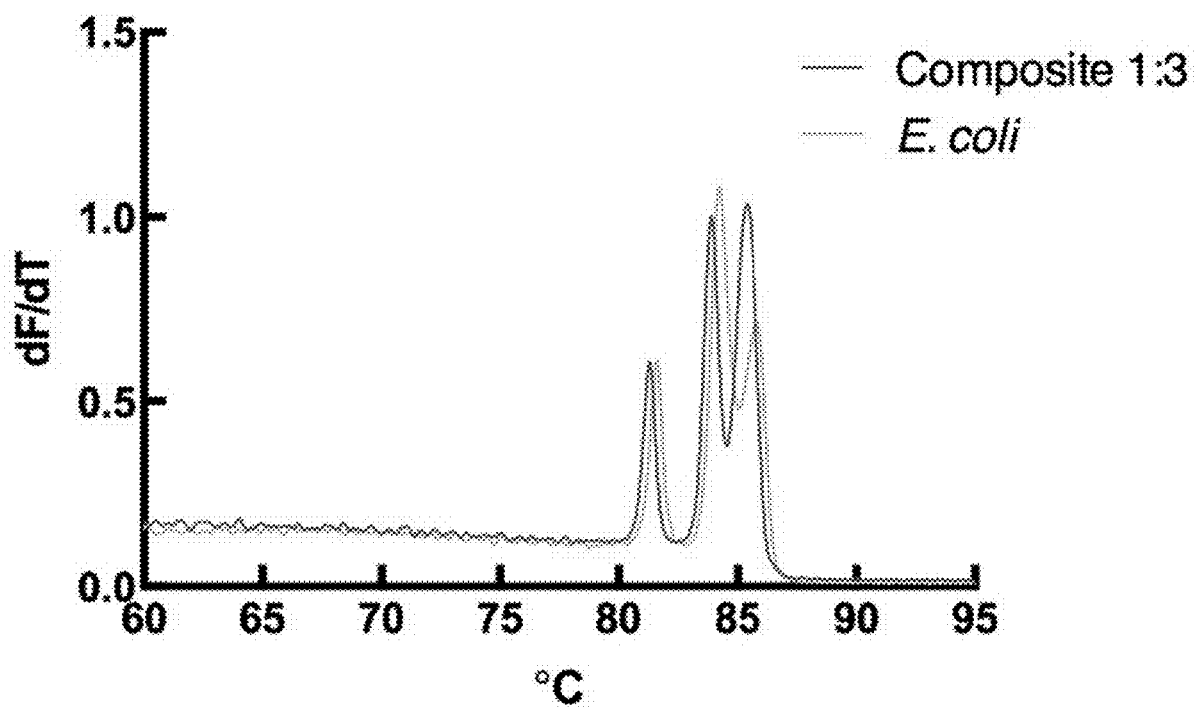

To confirm that multiple intragenomic ITS variants contributed to the curve complexity, we performed ITS HRM analysis on 20 *E. coli* ITS clones from which we observed two distinct melt curve profiles (FIG. 3D). Sequencing of the ITS inserts corresponding to these two different melt curve profiles matched to either ITS short or ITS long sequence. Based on the distribution of each group (15 and 5 colonies belong to group ITS short and ITS long respectively), we mixed one representative colony from each group in a 3:1 DNA concentration ratio and performed the ITS HRM assay. This resulted in a melt curve very similar to the original *E. coli* ITS melt curve (FIG. 3D).

Development of Classification Algorithm

Using our generated melt curve library, we performed a supervised classification analysis by training the proposed adaptive Naïve Bayes algorithm on a reference panel and testing the classifier on a separate panel of unknown samples. The goal is two-fold: 1) to predict whether the curve for the unknown sample is identifiable in the reference panel; and 2) to accurately identify the type of organism the unknown sample belongs to. Our algorithm adaptively introduces an auxiliary label indicating the possibility of the tested sample to be unrepresented in reference panel. This mechanism enables us to reliably identify novel samples, which have not been identified before. Our algorithm first calculates curve similarities based on both curve shapes and curve peak positions. Hilbert transform is used to enhance the similarity. With reliable similarity metric, our algorithm seeks nearest samples in the reference panel and constructs a probabilistic decision boundary based on the similarities to the test sample. Leave-One-Out Cross Validation (LOOCV) analysis on reference panel with this algorithm revealed that 95% of species curves were reliably identified.

ITS HRM Assay on Positive Blood Culture Samples

A convenience sample of 87 de-identified residual positive-blood-culture specimens were prospectively collected from the clinical microbiology laboratory for our ITS HRM assay (ITS PCR HRM analysis coupled with classification algorithm). Seventeen of 87 samples were omitted due to polybacterial or yeast culture results. We then performed 16S sequencing on 70 samples. The culture and sequencing results matched for 69 out of 70 samples. For our test samples, we omitted the sample with the discordant culture and 16S sequencing results. Additionally, 10 randomly selected samples that represented 10 different species that we had multiple samples of were assigned to train our classification algorithm, leaving us with 59 test samples, representing 21 different bacterial species of which 5 species were not in our database.

We performed the ITS HRM assay on these 59 samples in duplicate, and utilized the 16S sequencing results as the reference for correct melt curve classification. Our classification algorithm incorporated both duplicate melt curves of a sample for analysis and determined the top 2 curve matches accompanied by their respective confidence values. The algorithm correctly classified 53 samples as the top 1 match and misclassified 6 samples (i.e. sample was classified as the top 2 match, or was not in the top 2 match) calculated to 90% classification accuracy. When we include the top 2 matches, the algorithm was able to correctly classify 54 samples and misclassified 5 samples resulting in 92% classification accuracy (Table 1).

ITS HRM Assay on Cerebrospinal Fluid (CSF) Samples

In a case-control (~1:6) pilot study, a total of 43 clinical CSF samples were tested directly using our ITS HRM assay. Among these samples, 6 were monobacterial 16S sequence-confirmed culture-positive and 37 were culture-negative. Our ITS HRM assay and classification algorithm were able to detect and correctly identify all 6 culture-positive samples and identified 35 out of 37 culture-negative samples as negative, suggesting a 100% and 95% assay sensitivity and specificity, respectively (Tables 2A and 2B), albeit with a small sample size. Of the two false-positives, the 16S sequencing determined the two organisms as *Herminiimonas contaminans* and *Pseudomonas brenneri*. Our algorithm correctly classified *H. contaminans* as an unknown species in top 1 match, and misclassified *P. brenneri* in both top 1 and top 2 match with top 1 identifying it as *Pseudomonas aeruginosa*.

DISCUSSION

Our single-plex ITS HRM assay can be easily implemented to identify unknown bacterial species by observing their highly variable melt curve shapes with multiple peaks and wide Tm range (15° C.). In this study, we successfully differentiated and generated a training library of unique melt profiles for 89 different clinically relevant bacterial species, some from closely related species of the same genera. We also included melt curve data from some of the culture and sequence verified redundant clinical samples as additional training references to enhance the accuracy of our classification algorithm. Considering samples from 59 positive blood culture bottles and 6 culture-positive CSF samples, our ITS HRM analysis correctly identified a combined 65 positive samples with 5 discrepancies for a total combined accuracy of 97% at the genus-level and 92% at the species-level. This included correct classification of 5 unanticipated species not included in our database. Of note, in two of the discrepant blood-culture samples, our algorithm identified it as *Staphylococcus epidermis* and *Staphylococcus caprae*, whereas 16S sequencing identified them as *Staphylococcus hominis*, all members of coagulase-negative *Staphylococcus*, in which the clinical need to identify coagulase-negative *Staphylococcus* to species level remains controversial (Becker et al. (2014) Clin. Microbiol. Rev. 27:870-926). Two other discrepant samples were misclassified as unknowns, which in a clinical setting would have required additional analysis such as sequencing or awaiting culture for identification. We also demonstrated that our assay could directly test clinical CSF samples without prior culturing with high accuracy. The 2 false-positive CSF samples were determined by 16S sequencing as *H. contaminans* and *P. brenneri*, both known biopharmaceutical contaminants. Additional clinical data would help to determine their clinical significance. Our algorithm did misclassify the ITS HRM curve of *P. brenneri* as *P. aeruginosa*. Overall classification accuracy could likely be improved with further expansion of our training database.

The ITS sequence between the 16S-23 S rRNA is less evolutionarily constrained than its flanking genes for higher interspecies discrimination (Lee et al. (2009) *Nucleic Acids Res* 37:D489-493), making it well-suited as a single species-level phylogenetic locus to simplify assay format for routine clinical adoption. In addition, rRNA gene operons are known to exist in multiple copies (ranging from 1-15 for different species). To create highly diverse melt curves, we leveraged the unique heterogeneity of ITS copies harbored within a bacterial genome. By universally amplifying the multiple intragenomic allelic copies of ITS, each with length and sequence polymorphisms, heteroduplex products are formed due to partial sequence homology between different ITS copies. Our data confirmed intrinsic heteroduplex formation, as shown by others, without the need for external artificial manipulation. Heteroduplex formation is believed to increase in higher PCR amplification cycles when products accumulate and cross-hybridization occurs (Gtari et al. (2007) J. Appl. Microbiol. 103:1031-1040, Jensen et al. (1993) PCR Methods Appl. 3:186-194). However, heteroduplexes alone may not account for the diverse curve profiles. We believe it is the combination of the homoduplex sequence and length variations, large amplicon covering multiple melt domains, in addition to the heteroduplexes that produce the observed melt curve shapes.

Our current platform is most reliable for diagnosing monomicrobial infection. In the case of a polymicrobial sample, the contribution of individual bacterial populations to the ensemble melt curve is difficult to decouple and identify. We previously developed Universal digital High Resolution Melt (U-dHRM) to overcome this challenge by diluting the starting material such that each genotype is distributed into its own digital PCR reaction and generates a pure melt curve (Fraley et al. (2013) Nucleic Acids Res 41:e175). Targeting the 16S, this approach showed successful identification of a bacterial species at a single molecule level. The ability to quantitatively resolve the heterogeneity present in a sample may aid in identifying true infection versus colonization or contamination. However, the analysis was limited by the reliance on Tm reproducibility as the primary distinguishing attribute of the melt curve. For future assessment, replacing 16S rDNA with ITS as the target sequence will considerably increase the specificity of the U-dHRM analysis to resolve all species in a mixed sample. The simplicity of our single-plex assay also facilitates scaling to the single cell/molecule format with advanced microfluidic digital droplet platforms, making it highly sensitive to low level targets.

We have developed a new adaptive Naïve Bayes algorithm (described in detail in Supplementary Methods), which we demonstrate to be capable of differentiating between closely related species, a task previously challenging with 16S rRNA-based methods. Our algorithm consists of three steps, as described in Supplementary Methods. First, we align each curve according to a preset temperature to ensure improved accuracy in the subsequent curve similarity calculation. Second, our algorithm employs a Hilbert transformation of the melt curves, and constructs an enhanced similarity metric between curves. The resulting similarity metric is robust to noise in the curve measurements and contributes to the accuracy of the classifier. Finally, our algorithm performs Naïve Bayes-based classification and reports a final classification results by integrating posterior distributions for all melt curves from one species. Our algorithm is also extended with the function of identifying unseen samples outside the reference panel and reporting them as such. It is important to note that the classification capability of the proposed classifier depends heavily on the amount of training data, and should improve as more data become available. Based on previous results (Zimic et al. (2002) Trans. R Soc. Trop. Med. Hyg. 96 Suppl 1:S15-20), it is likely that generating more replicate melt training data should further improve accuracy of classification.

Overall, our results suggest that ITS HRM analysis system is a simple, rapid, and practical molecular approach for broad-scale microbial species identification. Our ITS HRM assay is the first to readily identify 89 bacterial species using a single-plex approach, without the need for microbial culture, hybridization probes, mass spectrometry, or sequencing. Our expandable reference database and trainable curve-matching algorithm with statistical interpretation enable discovery of unanticipated organisms updatable in our database after sequence verification. Similar use of ITS region may be extended to phylogenetic identification of other organism classes (Mandviwala et al. (2010) J. Mol. Diagn. 12:91-101, Somogyvari et al. (2012) In Vivo 26:979-983). Sequence fingerprinting of highly polymorphic genetic locus for other applications can also employ our analysis approach. Evaluation of clinical diagnostic performance for bloodstream infections directly from whole blood samples is currently underway. As a simple add-on to most commonplace qPCR with HRM capabilities or emerging molecular point-of-care platforms, our analysis system holds promise for clinical adoption as an early adjunctive test to traditional microbiological methods for etiologic diagnosis of acute febrile illnesses.

Methods

Bacterial Genomic DNA for Library Generation

Eighty-nine bacterial species were clinically isolated from clinical microbiology laboratory at Johns Hopkins Hospital or purchased from American Type Culture Collection (ATCC). Bacterial genomic DNA from these species were extracted as previously described (Won et al. (2010) J. Clin. Microbiol. 48:3410-3413).

PCR HRM Analysis

Real-time PCR amplification and HRM analysis of the ITS and 16S rRNA gene were performed on the Rotor-Gene Q thermal cycler (Qiagen, Venlo, Netherlands) with ITS primers pairs:

```
ITS1F
(5'-TTGTACACACCGCCCG-3', SEQ ID NO: 1)
and

ITS2R
(5'-YGCCAAGGCATCCACC-3', SEQ ID NO: 2)
and 16S primers pairs
V1F
(5'-GYGGCGNACGGGTGAGTAA-3', SEQ ID NO: 3)
and

V6R
(5'-AGCTGACGACANCCATGCA-3', SEQ ID NO: 4).
```

All standard measures to prevent sample contamination were taken including the use of a designated PCR workstation. PCR reactions were performed in a 20 µl volume using Type-It HRM kit (Qiagen, Venlo, Netherlands) with the addition of 200 nM low temperature calibrator (Fraley et al. (2013) Nucleic Acids Research 41:e175) and 2 µl genomic DNA. Before adding the low temperature calibrator and genomic DNA, each reaction was treated with 0.5 µL of dsDNase and 0.5 µL DTT (ArcticZymes PCR Decontamination Kit, ArcticZymes, Tromsø, Norway) followed by incubation at 37° C. for 20 minutes and 60° C. for 20 minutes to eliminate possible contaminating DNA. Reactions were covered with a 20 µl overlay of PCR grade mineral oil (Fisher Scientific), and cycling conditions were 95° C. for 5 minutes, followed by 40 amplification cycles of 95° C. for 15 seconds, 55° C. for 30 seconds, and 72° C. for 60 seconds for ITS or 90 seconds for 16S, 95° C. for 30 seconds and 28° C. for 30 seconds. HRM acquisition at every 0.1° C. immediately followed from 50° C. to 95° C. The entire run was completed within 3 hours. For determination of a sample being identified as PCR negative, the average of 20 CSF negative samples Ct values was calculated to be 28 with a standard deviation of 0.9. For our assay, any sample that had a Ct value below 26.2 (2 standard deviations from mean negative samples) and generated replicable melt curves was considered to be positive. HRM analysis was performed utilizing the RotorGene-Q software. Raw melt data files were exported and sent for further analysis utilizing the classification algorithm.

Heteroduplex Analysis

One µg of E. coli ATCC 25922 ITS PCR product was added to 25 µl final reaction volume containing 2.5 µl 10× reaction buffer and 1 µl of 10 U/µl mung bean nuclease. The reaction was incubated at 30° C. for 45 minutes. 25 µl of 0.02% SDS was added to stop the nuclease activity. The product was purified using MinElute Reaction Clean Up kit (Qiagen, Venlo, Netherlands) and eluted in 10 µl elution buffer. The purified nuclease treated samples were run in a 1% agarose gel, and imaged. For HRM analysis, ITS PCR reactions were performed as mentioned above and taken out after cycle number 20, 25, 30, 35, and 40. We put the reactions back into the thermal cycler and amplicons were melted from 65° C.-95° C. Melt profiles were evaluated utilizing the RotorGene-Q software.

For cloning of E. coli ITS, the ITS PCR product was purified using MinElute Reaction Clean Up kit (Qiagen, Venlo, Netherlands) and cloned using NEB PCR Cloning Kit (New England Biolabs, Ipswich, Mass.) following manufacturer's protocol. Twenty colonies were picked, screened for insert, and purified for plasmids. Each plasmid was subjected to ITS HRM analysis and the ITS PCR product of representative plasmids of ITS short and ITS long were sent for Sanger sequencing.

Blood Culture Sample Collection and Preparation

Eighty-seven waste positive blood culture bottles were consecutively collected between July and August 2015 in the clinical microbiology laboratory at Johns Hopkins Hospital (JHH) according to an approved IRB protocol. Briefly, blood was drawn from patients as part of routine clinical care for suspected bloodstream infections according the central hospital laboratory. The clinical blood culture bottles (BacT/Alert SN aerobic, FA aerobic, and SN anaerobic; bioMerieux Inc., Durham N.C.) used standard media and were processed using the BacT/Alert 3-D blood culture system (bioMérieux, Inc.). Further identification of bacterial isolates was performed using the Phoenix microbial identification system (Becton, Dickinson, Sparks, Md.). None of the bottles tested contained charcoal. After reference testing was complete, the remaining waste sample was deidentified for research purposes and stored at 4° C. Pathogens identified by standard microbiological testing were recorded. Explicit consent was not sought, since residual waste samples were retrospectively tested in a deidentified manner. Results from the PCR/HRMA test were compared to reference testing results, but not used to inform clinical treatment. Bacterial DNA was extracted from 500 µl aliquots of blood culture sample using a previously described protocol based on the Roche MagNA Pure extraction instrument (Roche Diagnostics) (Jeng et al. (2012) J. Clin. Microbiol. 50:3287-3292). All blood culture samples were initially stored at 4° C. Processing occurred as quickly as possible, with a maximum of 1 week of storage prior to batch DNA extraction.

CSF Samples Collection and DNA Extraction

A total of 415 waste clinical CSF samples, submitted to the clinical laboratory as part of routine care at Johns Hopkins Hospital, were consecutively collected between May 2012 to January of 2014 under a study protocol approved by the JHH IRB. All samples collected were deidentified after all relevant laboratory culture data has been recorded and stored in −80° C. prior to testing. For our case-control (~1:6) study, we randomly selected 6 culture-positive and 37 culture-negative CSF samples for testing. For sample preparation, 500 µl of CSF sample was centrifuged for 30 minutes at 13,000 rpm followed by DNA extraction protocol using Qiagen QIAamp DNA mini kit (Qiagen, Venlo, Netherlands). An additional 20 culture-negative samples were randomly selected for baseline negative Ct value determination.

16S Sequence Analysis

All blood culture and CSF samples were amplified for 16S using primers pairs V1F and V6R. The PCR product was purified for sequencing utilizing the Qiagen QIAquick PCR purification kit (Qiagen, Venlo, Netherlands) and sent for Sanger sequencing at MCLAB (San Francisco, Calif.). The sequencing results (typically 600-700 bp long) were used to choose the best matching database sequence in the NCBI database of 16S sequences using nucleotide BLAST.

Supervised Validation for Library Generation by Adaptive Naïve Bayes

We have utilized an Adaptive Naïve Bayes (ANB) algorithm in order to classify 89 species. The proposed adaptive naïve bayes (ANB) (See Supplementary Methods) is able to predict whether the unknown sample is among the reference panel and subsequently distinguish the species of the sample. We incorporated a low temperature calibrator DNA duplex to correct for tube-to-tube or run-to-run experimental variations for curve alignment and normalization.

TABLE 1

Identification results of 59 positive clinical blood culture samples.
Positive Clinical Blood Culture Samples

| | | | ITS HRM Result | | | |
|---|---|---|---|---|---|---|
| | Identification Results | | Top 1 Match | | Top 2 Match | |
| No. | Culture Result | Sequencing Result | Classified | Misclassified | Classified | Misclassified |
| 1 | *Escherichia coli* | *Escherichia coli* | ✓ | | ✓ | |
| 2 | *Citrobacter freundii* | *Citrobacter freundii* | ✓ | | ✓ | |
| 3 | *Pseudomonas aeruginosa* | *Pseudomonas aeruginosa* | ✓ | | ✓ | |
| 4 | *Serratia marcescens* | *Serratia marcescens* | ✓ | | ✓ | |
| 5 | *Staphylococcus* species, coagulase negative | *Staphylococcus epidermis* | ✓ | | ✓ | |
| 6 | *Escherichia coli* | *Escherichia coli* | ✓ | | ✓ | |
| 7 | *Staphylococcus* species, coagulase negative | *Staphylococcus epidermis* | ✓ | | ✓ | |
| 8 | *Staphylococcus aureus* | *Staphylococcus aureus* | ✓ | | ✓ | |
| 9 | *Streptococcus* group A | *Streptococcus pyogenes* | ✓ | | ✓ | |
| 10 | *Streptococcus* group C/G | *Streptococcus dysgalactidae* | ✓ | | ✓ | |
| 11 | *Staphylococcus aureus* | *Staphylococcus aureus* | ✓ | | ✓ | |
| 12 | *Staphylococcus aureus* | *Staphylococcus aureus* | ✓ | | ✓ | |
| 13 | *Escherichia coli* | *Escherichia coli* | ✓ | | ✓ | |
| 14 | *Staphylococcus aureus* | *Staphylococcus aureus* | ✓ | | ✓ | |
| 15 | *Staphylococcus aureus* | *Staphylococcus aureus* | ✓ | | ✓ | |
| 16 | *Staphylococcus aureus* | *Staphylococcus aureus* | ✓ | | ✓ | |
| 17 | *Escherichia coli* | *Escherichia coli* | ✓ | | ✓ | |
| 18 | *Staphylococcus aureus* | *Staphylococcus aureus* | ✓ | | ✓ | |
| 19 | *Staphylococcus* species, coagulase negative | *Staphylococcus epidermis* | ✓ | | ✓ | |
| 20 | *Escherichia coli* | *Escherichia coli* | ✓ | | ✓ | |
| 21 | *Staphylococcus* species, coagulase negative | *Staphylococcus epidermis* | ✓ | | ✓ | |

TABLE 1-continued

Identification results of 59 positive clinical blood culture samples.

Positive Clinical Blood Culture Samples

| | | | ITS HRM Result | | | |
|---|---|---|---|---|---|---|
| | Identification Results | | Top 1 Match | | Top 2 Match | |
| No. | Culture Result | Sequencing Result | Classified | Misclassified | Classified | Misclassified |
| 22 | *Enterobacter cloacae* | *Enterobacter cloacae* | ✓ | | ✓ | |
| 23 | *Klebsiella oxytoca* | *Klebsiella oxytoca* | ✓ | | ✓ | |
| 24 | *Streptococcus* group B | *Streptococcus agalactiae* | ✓ | | ✓ | |
| 25 | *Escherichia coli* | *Escherichia coli* | ✓ | | ✓ | |
| 26 | *Escherichia coli* | *Escherichia coli* | ✓ | | ✓ | |
| 27 | *Acinetobacter baumannii/calcoaceticus* complex | *Acinetobacter baumannii* | ✓ | | ✓ | |
| 28 | *Staphylococcus* species, coagulase negative | *Staphylococcus epidermis* | ✓ | | ✓ | |
| 29 | *Staphylococcus aureus* | *Staphylococcus aureus* | ✓ | | ✓ | |
| 30 | *Staphylococcus aureus* | *Staphylococcus aureus* | ✓ | | ✓ | |
| 31 | *Staphylococcus* species, coagulase negative | *Staphylococcus hominis* | ✓ | | ✓ | |
| 32 | *Staphylococcus* species, coagulase negative | *Staphylococcus epidermis* | ✓ | | ✓ | |
| 33 | *Serratia marcescens* | *Serratia marcescens* | ✓ | | ✓ | |
| 34 | *Staphylococcus* species, coagulase negative | *Staphylococcus epidermis* | ✓ | | ✓ | |
| 35 | *Staphylococcus aureus* | *Staphylococcus aureus* | ✓ | | ✓ | |
| 36 | *Klebsiella pneumoniae* | *Klebsiella pneumoniae* | ✓ | | ✓ | |
| 37 | *Enterococcus faecalis* | *Enterococcus faecalis* | ✓ | | ✓ | |
| 38 | *Enterococcus faecalis* | *Enterococcus faecalis* | ✓ | | ✓ | |
| 39 | *Micrococcus luteus* | *Micrococcus luteus* | ✓ | | ✓ | |
| 40 | *Klebsiella pneumoniae* ss. *ozaenae* | *Klebsiella pneumoniae* | ✓ | | ✓ | |
| 41 | *Staphylococcus* species, coagulase negative | *Staphylococcus epidermis* | ✓ | | ✓ | |
| 42 | *Escherichia coli* | *Escherichia coli* | ✓ | | ✓ | |
| 43 | *Staphylococcus aureus* | *Staphylococcus aureus* | ✓ | | ✓ | |
| 44 | *Viridans streptococcus* group | *Streptococcus parasanguinis* | ✓ | | ✓ | |
| 45 | *Klebsiella pneumoniae* | *Klebsiella pneumoniae* | ✓ | | ✓ | |
| 46 | *Staphylococcus aureus* | *Staphylococcus aureus* | ✓ | | ✓ | |
| 47 | *Staphylococcus* species, coagulase negative | *Staphylococcus epidermis* | ✓ | | ✓ | |
| 48 | *Flavonifractor plautii* | *Flavonifractor plautii* | ✓ | | ✓ | |
| 49 | *Staphylococcus* species, coagulase negative | *Staphylococcus pettenkoferi* | U | | U | |
| 50 | *Corynebacterium amycolatum* | *Corynebacterium* sp. | U | | U | |
| 51 | *Fusobacterium necrophorum* | *Fusobacterium necrophorum* | U | | U | |
| 52 | *Moraxella osloensis* | *Moraxella osloensis* | U | | U | |
| 53 | *Bacteroides fragilis* group, not fragilis/thetaiotaomicron | *Bacteroides ovatus* | U | | U | |
| 54 | *Klebsiella pneumoniae* | *Klebsiella pneumoniae* | | *E. coli* | ✓ | |
| 55 | *Viridans streptococcus* group | *Streptococcus mitis* | | *S. agalactiae* | | *S. agalactiae* |
| 56 | *Staphylococcus* species, coagulase negative | *Staphylococcus hominis* | | *S. epidermis* | | *S. epidermis* |
| 57 | *Staphylococcus* species, coagulase negative | *Staphylococcus hominis* | | *S. caprae* | | *S. caprae* |
| 58 | *Serratia marcescens* | *Serratia marcescens* | U | | U | |
| 59 | *Klebsiella pneumoniae* | *Klebsiella pneumoniae* | U | | U | |

U: Unknown (sample identified as an organism that was not in the database).

TABLE 2A

Comparison of the ITS HRM assay and culture results from CSF samples.

| CSF Samples | | ITS HRM assay | | |
|---|---|---|---|---|
| | Detection | + | − | Total |
| Conventional Culture | + | 6[A] | 0 | 6 |
| | − | 2[B] | 35 | 37 |
| | Total | 8 | 35 | 43 |

[A]The ITS HRM assay results matched the culture (and sequencing) results.
[B]The ITS HRM assay was able to detect bacterial organisms in 2 culture negative CSF samples.

TABLE 2B

Identification results of 8 ITS-HRM positive clinical CSF samples.
Positive Clinical CSF Samples

| | Identification Results | | ITS HRM Result | |
|---|---|---|---|---|
| No. | Culture | 16S Sequencing | Classified | Misclassified |
| 1 | *Staphylococcus* species, coagulase negative | *Staphylococcus caprae* | ✓ | |
| 2 | *Staphylococcus* species, coagulase negative | *Staphylococcus caprae* | ✓ | |
| 3 | *Staphylococcus* species, coagulase negative | *Staphylococcus caprae* | ✓ | |
| 4 | *Streptococcus* group B | *Streptococcus agalactiae* | ✓ | |
| 5 | *Staphylococcus* species, coagulase negative | *Staphylococcus epidermis* | ✓ | |
| 6 | *Streptococcus* group B | *Streptococcus agalactiae* | ✓ | |
| 7 | Negative | *Herminiimonas contaminans* | U | |
| 8 | Negative | *Pseudomonas brenneri* | | *P. aeruginosa*[4] |

U: Unknown (sample identified as an organism that was not in the database).
[A]The algorithm misclassified this sample in both top 1 and top 2 matches.

Supplementary Methods

1. Naive Bayes

In this section, we present details about the proposed adaptive naive bayes algorithm. Given C species in the reference dataset, and for the i-th species $C_i$, we have $N_i$ number of training samples. For any new unknown test sample x, we aim to calculate the posteriori probability via Bayes' theorem:

$$p(C_k \mid x) = \frac{p(C_k)p(x \mid C_k)}{p(x)}$$

where $p(C_k)$ is the prior for the k-th species, and $p(x|C_k)$ is the likelihood function given all the training samples in the k-th species.

The prior or information is assumed to be homogeneous:

$$p(C_k) = \frac{1}{C}.$$

The likelihood function is calculated with a Gaussian distribution:

$$p(x \mid C_k) = \sum_{x'_j \in C_k} \frac{1}{\sqrt{2\pi\alpha}} \exp\left(-\frac{D(x, x'_j)}{2\alpha}\right).$$

The essence in the algorithm lies in the way we calculate the distance $D(x; x'j)$ This measures the similarity between curve shapes for the test sample and training reference.

Assume for a test species, denoted as $S_t = \{S_t^1, S_t^2, \ldots, S_t^m\}$ where m is the number of replicates in this species. We want to achieve a consensus prediction of whether this species falls into any species category from the reference panel. We assume each replicate is of same importance, so we just average the final posteriori probability of each replicate to obtain the prediction for the test species:

$$p(C_k \mid S_t) = \frac{1}{m} \sum_{j}^{m} p(C_k \mid S_t^j)$$

2. Curve Similarity Calculation

There are three steps in the calculation of curve similarity. First, we align each curve according to the temperature of 53°. This guarantees each curve is well-aligned and thus high accuracy in the following curve similarity calculation. Second, we apply Hilbert Transformation on the curves. Hilbert transformation is a convolution process on the curve:

$$H(f)(t) = \frac{1}{\pi} \int_{-\infty}^{\infty} \frac{f(\tau)}{t - \tau} d\tau$$

where f(t) denotes the curve we have. The output of Hilbert transformation is a complex function where the real part is the original input and the complex part denotes the transformed domain. We calculate the distance between two curves by combining the two parts as follows:

$$D(f, g) = \sum_{t} \|\text{real}(H(f)(t)) - \text{real}(H(g)(t))\|^2 + \sum_{t} \|\text{complex}(H(f)(t)) - \text{complex}(H(g)(t))\|^2$$

where f and g represent two curves.

3. Details in Predicting Out-of-Reference Samples

To distinguish whether the test target belongs to any species in the reference panel, we adapt the original naive bayes to accommodate the prediction of out-of-reference samples. Assume for a test species, denoted as $S_t = \{S_t^1, S_t^2, \ldots, S_t^m\}$ where m is the number of replicates in this species. First, for each replicate, we assign a prior probability to be out-of-reference sample by looking at the curve region between Temperature 52.5° to 53.5°. This would give us some knowledge about whether this replicate is an outlier because most of outlier curves will generate some unusual peak curves in this temperature region. Further, when we apply naive bayes, we assign the posteriori probability to be out-of-reference by adding a gated function that if the following quantile is below some threshold:

$$P(S_t \in C_0) = I\left\{\max_k p(S_t \mid C_k) < \theta\right\}.$$

we set θ=0:3 in our experiments.

TABLE 3

List of 89 reference bacterial species in the database.
Bacterial Species in Database Acinetobacter baumannii
Acinetobacter haemolyticus
Acinetobacter johnsonii
Acinetobacter lwoffii
Aerococcus sanguinicola
Aerococcus urinae
Aerococcus viridans
Aeromonas caviae
Bacillus anthracis (2 strains)
Bacillus cereus
Bacillus halodurans
Bacillus mycoides
Bacillus polymyxa
Bacillus subtilis
Bacillus thuringensis
Bacteriodes fragilis
Bordetella parapertussis
Bordetella pertussis
Borrelia burgdorferi
Brucella abortus
Brucella ovis
Burkholderia cepacia
Burkholderia mallei
Burkholderia pseudomallei
Campylobacter fetus
Chlamydia pneumoniae
Chlamydia trachomatis
Citrobacter freundii
Clostridium perfingens
Corynebacterium diphtheriae
Corynebacterium jeikeium
Eikenella corrodens
Enterobacter agglomerans
Enterobacter cloacae
Enterococcus casseliflavus
Enterococcus durans
Enterococcus faecalis
Enterococcus faecium
Enterococcus gallinarum
Enterococcus raffinosus
Escherichia coli
Escherichia vulneris TABLE 3-continued List of 89 reference bacterial species in the database.
Bacterial Species in Database Francisella philomiragia
Francisella tularensis
Fusobacterium nucleatum
Haemophilus influenzae
Klebsiella oxytoca
Klebsiella pneumoniae
Legionella pneumophila
Micrococcus luteus
Morganella morganii
Mycoplasma hominis
Neisseria lactamica
Neisseria meningitidis
Neisseria sublfava
Oligella urethralis
Pasteurella multicoda
Propionibacterium acnes
Proteus vulgaris
Providencia rettgeri
Providencia stuartii
Pseudomonas aeruginosa
Pseudomonas putida
Salmonella bongorii
Salmonella enterica Enteritidis
Serratia liquifaciens
Serratia marcescens
Shigella flexneri
Shigella sonnei
Staphylococcus aureus
Staphylococcus capitis (CoNS)
Staphylococcus caprae (CoNS)
Staphylococcus epidermidis (CoNS)
Staphylococcus haemolyticus (CoNS)
Staphylococcus hominis (CoNS)
Staphylococcus lentus (CoNS)
Staphylococcus lugdunensis (CoNS)
Staphylococcus saprophyticus (CoNS)
Staphylococcus xylosus (CoNS)
Stenotrophomonas maltophilia
Streptococcus agalactiae
Streptococcus dysgalactiae
Streptococcus parasanguinis
Streptococcus pneumoniae (5 strains)
Streptococcus pyogenes
Streptococcus anginosus
Vibrio fluvialis
Yersinia pestis (2 strains)
Yersinia pseudotuberculosis Although preferred embodiments of the subject invention have been described in some detail, it is understood that obvious variations can be made without departing from the spirit and the scope of the invention as defined herein.

What is claimed is:

1. A method for identifying bacteria in a biological sample from a subject, the method comprising:
   a) providing the biological sample from the subject;
   b) isolating bacterial DNA from the biological sample;
   c) amplifying at least a portion of an internal transcribed spacer (ITS) region of the bacterial DNA using at least one set of primers capable of specifically hybridizing to the ITS region, whereby an amplicon is produced;
   d) performing high resolution melt (HRM) analysis of the amplicon;
   e) aligning an HRM curve for the amplicon with a plurality of reference HRM curves for genomic ITS DNA from known bacterial species;
   f) applying a Hilbert transformation on the HRM curve for the amplicon and each reference HRM curve; and
   g) identifying the species of the bacteria by finding a Hilbert transformed reference HRM curve for genomic ITS DNA from a known bacterial species that matches the Hilbert transformed HRM curve for the amplicon, wherein the matching reference HRM curve is distinguished from other reference HRM curves among the plurality of reference HRM curves for genomic ITS DNA from known bacterial species based on HRM curve similarity in both curve shape and curve peak positions using a supervised machine learning algorithm for classification.

2. The method of claim 1, wherein said identifying the species further comprises comparing melting temperature ($T_m$) of the amplicon.

3. The method of claim 1, wherein said identifying the species further comprises distinguishing the bacteria in the biological sample from other known bacterial species with ITS regions having different lengths, copy number, or sequences based on comparing the HRM curve of the amplicon to reference HRM curves for genomic ITS DNA from the known bacterial species.

4. The method of claim 1, wherein the amplicon comprises the entire ITS region.

5. The method of claim 1, wherein said at least one set of primers is selected from the group consisting of:
   a) a forward primer comprising the nucleotide sequence of SEQ ID NO:1 and a reverse primer comprising the sequence of SEQ ID NO:2;
   b) a forward primer comprising at least 10 contiguous nucleotides of the nucleotide sequence of SEQ ID NO:1 and a reverse primer comprising at least 10 contiguous nucleotides of the nucleotide sequence of SEQ ID NO:2;
   c) a forward primer comprising a nucleotide sequence having at least 95% identity to the sequence of SEQ ID NO:1 and a reverse primer comprising a nucleotide sequence having at least 95% identity to the sequence of SEQ ID NO:2, wherein the primer is capable of hybridizing to and amplifying bacterial ITS DNA;
   d) a forward primer and a reverse primer comprising at least one nucleotide sequence that differs from the corresponding nucleotide sequence of the forward primer or reverse primer of the primer set of (a) in that the primer has up to three nucleotide changes compared to the corresponding sequence, wherein the primer is capable of hybridizing to and amplifying bacterial ITS DNA; and
   e) a forward primer and a reverse primer comprising nucleotide sequences that are full complements of the corresponding nucleotide sequences of the forward primer and reverse primer of a primer set selected from the group consisting of (a)-(d).

6. The method of claim 1, further comprising culturing the bacteria from the biological sample prior to amplification of the bacterial nucleic acids.

7. The method of claim 1, wherein amplifying comprises performing polymerase chain reaction (PCR) or isothermal amplification.

8. The method of claim 1, wherein the PCR is real-time PCR or droplet digital PCR (ddPCR).

9. The method of claim 1, wherein the amplification is performed on bacterial DNA from a single cell.

10. The method of claim 1, further comprising fractionating the biological sample prior to performing steps (b)-(e).

11. The method of claim 10, wherein said fractionating comprises partitioning the biological sample into separate picoliter-scale volumes.

12. The method of claim 1, wherein the biological sample is infected biological tissue or fluid.

13. The method of claim 12, wherein the biological sample is selected from the group consisting of blood, cerebrospinal fluid (CSF), saliva, mucus, lymph fluid, lavage fluid, skin, or soft tissue.

14. The method of claim 1, wherein the biological sample is infected with a single species of bacteria.

15. The method of claim 1, wherein the biological sample is infected with more than one species of bacteria.

16. The method of claim 15, further comprising isolating one species of bacteria from the biological sample by diluting the biological sample and removing a portion of the biological sample containing only one species of bacteria, and performing steps (b)-(e) on said portion of the biological sample.

17. The method of claim 15, further comprising separately amplifying bacterial DNA from each of the species by droplet digital PCR and performing steps (d) and (e) on the amplicons from each of the species separately.

18. The method of claim 1, further comprising contacting the amplicon with an intercalating dye prior to performing HRM analysis.

19. The method of claim 18, wherein the intercalating dye is a fluorescent dye.

20. The method of claim 1, wherein HRM analysis is performed in the temperature range from about 50° C. to about 95° C.

21. The method of claim 1, wherein the plurality of reference HRM curves for genomic ITS DNA from known bacterial species are from a database of reference HRM curves for genomic ITS DNA from known bacterial species.

22. The method of claim 21, wherein the database comprises one or more reference HRM curves selected from FIGS. 4-92 or all the reference HRM curves in FIGS. 4-92.

23. The method of claim 21, wherein said identifying the species of bacteria is automated by use of a computer model or algorithm that classifies bacteria based on the comparison to the database of reference HRM curves.

24. The method of claim 1, wherein the supervised machine learning algorithm for classification uses a Naive Bayes classifier.

25. The method of claim 1, further comprising performing HRM analysis of another phylogenetic locus in the bacterial DNA.

26. The method of claim 25, wherein the phylogenetic locus is a 16S rRNA locus, 23S rRNA locus, or an rpo locus.

27. The method of claim 1, wherein said HRM curve similarity is determined by calculating the distance between the HRM curve for the amplicon and the reference HRM curve for genomic ITS DNA from the known bacterial species using the formula:

$$D(f, g) = \sum_t \|\text{real}(H(f)(t)) - \text{real}(H(g)(t))\|^2 + \sum_t \|\text{complex}(H(f)(t)) - \text{complex}(H(g)(t))\|^2$$

where f and g represent two curves.

28. The method of claim 1, wherein the HRM curve for the amplicon and the plurality of reference HRM curves are melt curve first derivative plots.

29. The method of claim 7, wherein the PCR is singleplex PCR for amplifying only the ITS region of the bacterial DNA.

* * * * *

SEQUENCE LISTING

```
<160> NUMBER OF SEQ ID NOS: 6

<210> SEQ ID NO 1
<211> LENGTH: 16
<212> TYPE: DNA
<213> ORGANISM: Artificial Sequence
<220> FEATURE:
<223> OTHER INFORMATION: ITS1F primer
<220> FEATURE:
<221> NAME/KEY: source
<222> LOCATION: (1)..(16)
<223> OTHER INFORMATION: sequence is synthesized

<400> SEQUENCE: 1
ttgtacacac cgcccg                                                     16
```

```
<210> SEQ ID NO 2
<211> LENGTH: 16
<212> TYPE: DNA
<213> ORGANISM: Artificial Sequence
<220> FEATURE:
<223> OTHER INFORMATION: ITS2R primer
<220> FEATURE:
<221> NAME/KEY: source
<222> LOCATION: (1)..(16)
<223> OTHER INFORMATION: sequence is synthesized

<400> SEQUENCE: 2
ygccaaggca tccacc                                                   16

<210> SEQ ID NO 3
<211> LENGTH: 19
<212> TYPE: DNA
<213> ORGANISM: Artificial Sequence
<220> FEATURE:
<223> OTHER INFORMATION: V1F primer
<220> FEATURE:
<221> NAME/KEY: source
<222> LOCATION: (1)..(19)
<223> OTHER INFORMATION: sequence is synthesized
<220> FEATURE:
<221> NAME/KEY: misc_feature
<222> LOCATION: (7)..(7)
<223> OTHER INFORMATION: n is a, c, g, or t

<400> SEQUENCE: 3
gyggcgnacg ggtgagtaa                                                19

<210> SEQ ID NO 4
<211> LENGTH: 19
<212> TYPE: DNA
<213> ORGANISM: Artificial Sequence
<220> FEATURE:
<223> OTHER INFORMATION: V6R primer
<220> FEATURE:
<221> NAME/KEY: source
<222> LOCATION: (1)..(19)
<223> OTHER INFORMATION: sequence is synthesized
<220> FEATURE:
<221> NAME/KEY: misc_feature
<222> LOCATION: (12)..(12)
<223> OTHER INFORMATION: n is a, c, g, or t

<400> SEQUENCE: 4
agctgacgac anccatgca                                                19

<210> SEQ ID NO 5
<211> LENGTH: 361
<212> TYPE: DNA
<213> ORGANISM: Escherichia coli

<400> SEQUENCE: 5
ccttacctta aagaagcgta ctttgcagtg ctcacacaga ttgtctgata gaaagtgaaa    60
agcaaggcgt cttgcgaagc agactgacac gtcccttcg tctagaggcc caggacaccg    120 cccttcacg gcggtaacag gggttcgaat cccctagggg acgccacttg ctggtttgtg    180
agtgaaagtc acctgcctta atatctcaaa actcatcttc gggtgatgtt tgagatattt    240 gctcttaaa aatctggatc aagctgaaaa ttgaaacact gaacaacgag agttgttcgt    300
gagtctctca aattttcgca acacgatgat gaatcgcaag aaacatcttc gggttgtgag    360
g                                                                   361
```

```
<210> SEQ ID NO 6
<211> LENGTH: 453
<212> TYPE: DNA
<213> ORGANISM: Escherichia coli

<400> SEQUENCE: 6
ccttacctta aagaagcgta ctttgcagtg ctcacacaga ttgtctgatg aaaatgagca        60
gtaaaacctc tacaggcttg tagctcaggt ggttagagcg cacccctgat aagggtgagg       120
tcggtggttc aagtccactc aggcctacca aatttgcacc gcaaatttga agaggtttta       180
actacatgtt atggggctat agctcagctg ggagagcgcc tgctttgcac gcaggaggtc       240
tgcggttcga tcccgcatag ctccaccatc tctgtagtga ttaaataaaa aatacttcag       300
agtgtacctg caaaggttca ctgcgaagtt ttgctcttta aaaatctgga tcaagctgaa       360
aattgaaaca ctgaacaacg agagttgttc gtgagtctct caaattttcg caacacgatg       420
atgaatcgca agaaacatct tcgggttgtg agg                                   453
```